(12) United States Patent
Namiki et al.

(10) Patent No.: US 12,065,541 B2
(45) Date of Patent: Aug. 20, 2024

(54) THERMOPLASTIC RESIN, OPTICAL FILM MADE THEREFROM, DIOL COMPOUND, DIESTER COMPOUND

(71) Applicant: MITSUBISHI CHEMICAL CORPORATION, Tokyo (JP)

(72) Inventors: Shingo Namiki, Tokyo (JP); Yuuichi Hirami, Tokyo (JP); Koji Nakamura, Tokyo (JP); Hiroyuki Hayashi, Tokyo (JP); Tomoko Maeda, Tokyo (JP); Kenichi Satake, Tokyo (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 444 days.

(21) Appl. No.: 17/456,259

(22) Filed: Nov. 23, 2021

(65) Prior Publication Data

US 2022/0081510 A1  Mar. 17, 2022

Related U.S. Application Data

(63) Continuation of application No. PCT/JP2020/024490, filed on Jun. 23, 2020.

(30) Foreign Application Priority Data

Jun. 24, 2019  (JP) .................................. 2019-116226

(51) Int. Cl.
*C08G 63/672* (2006.01)
*C07D 215/14* (2006.01)
(Continued)

(52) U.S. Cl.
CPC ......... *C08G 63/672* (2013.01); *C07D 215/14* (2013.01); *C08G 63/81* (2013.01);
(Continued)

(58) Field of Classification Search
CPC .... C07D 215/14; C07D 221/18; C08G 63/64; C08G 63/672; C08G 63/6856;
(Continued)

(56) References Cited

U.S. PATENT DOCUMENTS 5,171,745 A   12/1992  De Noble et al.
6,531,569 B1*  3/2003  Tachiki .................. B01D 71/56
                                                528/289
(Continued)

FOREIGN PATENT DOCUMENTS

CN  104718237 A  6/2015
CN  107075099 A  8/2017
(Continued)

OTHER PUBLICATIONS

Park et al "Cross-Linked, Luminescent Spherical Colloidal and Hollow-Shell Particles", Langmuir 2001, 17,7670-7674. (Year: 2001).*
Yuning Li et al "Synthesis and Properties of Random and Alternating Fluorene/Carbazole Copolymers for Use in Blue Light-Emitting Devices", Chem. Mater. 2004, 16, 2165-2173 (Year: 2004).*
N. S. Prostakov et al "9-Carbethoxy (Carboxy) Alkyl-4-Azafluorenes", Khimiya Geterotsiklicheskikh Soedinenii, No. 8, pp. 1083-1085, Aug. 1992 (Year: 1992).*
Office Action issued Mar. 5, 2024, in Japanese Patent Application No. 2020-107502 (with English language machine translation).
International Preliminary Report on Patentability and Written Opinion issued Jan. 6, 2022 in PCT/JP2020/024490 (submitting English translation only), 6 pages.
Nakano et al., "Dibenzofulvene, a 1,1-Diphenylethylene Analogue, Gives a π-Stacked Polymer by Anionic, Free-Radical, and Cationic Catalysts" Journal of the American Chemical Society, No. 123, Aug. 25, 2001, pp. 9182-9183.
(Continued)

*Primary Examiner* — Frances Tischler
*Assistant Examiner* — Gennadiy Mesh
(74) *Attorney, Agent, or Firm* — Oblon, McClelland, Maier & Neustadt, L.L.P.

(57) ABSTRACT

A thermoplastic resin including a structural unit of formula (1):

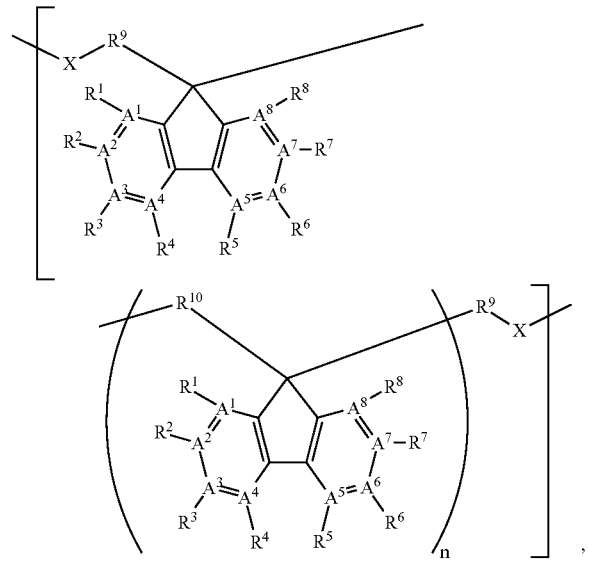

wherein $A^1$ to $A^8$ are each independently =CH— or =N—, and at least one of $A^1$ to $A^8$ is =N—. $R^1$ to $R^8$ are each independently a hydrogen atom, an alkyl group, an aryl group, a heteroaryl group, or the like. At least two adjacent groups out of $R^1$ to $R^8$ are optionally bonded to each other to form a ring. $R^9$ and $R^{10}$ are each independently a direct bond or an optionally substituted alkylene group having 1 to 20 carbon atoms. X is an oxygen atom, a carbonyl group, or an optionally substituted amino group, and n is an integer of 1 to 5. A retardation film, a circularly polarizing plate containing the thermoplastic resin are disclosed.

15 Claims, No Drawings

(51) Int. Cl.
  *C08G 63/81* (2006.01)
  *C08G 63/83* (2006.01)
  *C08J 5/18* (2006.01)
  *G02B 5/30* (2006.01)
(52) U.S. Cl.
  CPC .............. *C08G 63/83* (2013.01); *C08J 5/18* (2013.01); *G02B 5/3025* (2013.01); *C08J 2367/02* (2013.01)
(58) Field of Classification Search
  CPC ........ C08G 63/81; C08G 63/83; C08G 64/12; C08G 85/00; C08J 2367/02; C08J 2369/00; C08J 5/18; G02B 5/3025
  See application file for complete search history.

(56) References Cited

U.S. PATENT DOCUMENTS

| | | | |
|---|---|---|---|
| 6,565,974 | B1 | 5/2003 | Uchiyama et al. |
| 8,110,685 | B2 * | 2/2012 | Kosuge .............. H10K 85/6572 546/111 |
| 8,218,937 | B2 | 7/2012 | Iida et al. |
| 8,778,486 | B2 | 7/2014 | Tanaka et al. |
| 8,877,304 | B2 | 11/2014 | Motoyoshi et al. |
| 9,518,150 | B2 | 12/2016 | Uehara et al. |
| 10,081,707 | B2 | 9/2018 | Namiki et al. |
| 10,370,473 | B2 | 8/2019 | Nakayama et al. |
| 10,597,489 | B2 | 3/2020 | Uehira et al. |
| 10,670,773 | B2 * | 6/2020 | Namiki .................. H10K 50/86 |
| 10,711,015 | B2 | 7/2020 | Lee et al. |
| 10,766,910 | B2 | 9/2020 | Lee et al. |
| 10,899,882 | B2 | 1/2021 | Uehira et al. |
| 2008/0154040 | A1 * | 6/2008 | Kosuge ................ C07D 471/04 546/88 |
| 2010/0003490 | A1 | 1/2010 | Iida et al. |
| 2010/0104777 | A1 | 4/2010 | Motoyoshi et al. |
| 2011/0059948 | A1 * | 3/2011 | Chattopadhyaya ..... A61P 31/06 514/285 |
| 2012/0170118 | A1 | 7/2012 | Wang et al. |
| 2012/0308796 | A1 | 12/2012 | Tanaka et al. |
| 2014/0268334 | A1 | 9/2014 | Tanaka et al. |
| 2015/0247002 | A1 | 9/2015 | Uehara et al. |
| 2017/0204220 | A1 | 7/2017 | Namiki et al. |
| 2018/0040834 | A1 | 2/2018 | Choi et al. |
| 2018/0305486 | A1 | 10/2018 | Nakayama et al. |
| 2018/0362709 | A1 | 12/2018 | Uehira et al. |
| 2019/0225627 | A1 | 7/2019 | Lee et al. |
| 2020/0032138 | A1 | 1/2020 | Lee et al. |
| 2020/0131309 | A1 | 4/2020 | Uehira et al. |

FOREIGN PATENT DOCUMENTS

| | | |
|---|---|---|
| CN | 108473436 A | 8/2018 |
| CN | 109790185 A | 5/2019 |
| EP | 2 910 589 A1 | 8/2015 |
| JP | 05-027118 A | 2/1993 |
| JP | 10-068816 A | 3/1998 |
| JP | 2000-137116 A | 5/2000 |
| JP | 3325560 B2 | 9/2002 |
| JP | 2008-112124 A | 5/2008 |
| JP | 2008-222965 A | 9/2008 |
| JP | 5119250 B2 | 1/2013 |
| JP | 5204200 B2 | 6/2013 |
| JP | 2015-025111 A | 2/2015 |
| JP | 2018-077523 A | 5/2018 |
| JP | 2020-105101 A | 7/2020 |
| KR | 10-2011-0087278 A | 8/2011 |
| TW | 201434960 A | 9/2014 |
| WO | WO 2014/061677 A1 | 4/2014 |
| WO | WO 2017/115649 A1 | 7/2017 |
| WO | WO 2017/146022 A1 | 8/2017 |
| WO | WO 2019/004279 A1 | 1/2019 |

OTHER PUBLICATIONS

Marquise et al., "Deproto-metallation using mixed lithium-zinc and lithium-copper bases and computed CH acidity of 2-substituted quinolones", RSC Advances, No. 4, Apr. 16, 2014, pp. 19602-19612.

Lassagne et al., "A Combined Experimental and Theoretical Study of the Ammonium Bifluoride Catalyzed Regioselective Synthesis of Quinoxalines and Pyrido[2,3-b]pyrazines", Synthesis, No. 47, May 19, 2015, pp. 2680-2689.

Royer et al., "Asymmetric Synthesis. 2. Practical Method for the Asymmetric Synthesis of Indolizidine Alkaloids: Total Synthesis of (-)-Monomorine I", The Journal of Organic Chemistry, vol. 50, No. 5, 1985 pp. 670-673.

International Search issued Sep. 15, 2020 in PCT/JP2020/024490 filed on Jun. 23, 2020, citing documents BA, BE, BG & BO-BS therein, 2 pages.

Saikia et al., "Facile C—H Alkylation in Water: Enabling Defect-Free Materials for Optoelectronic Devices" The Journal of Organic Chemistry, No. 75, Mar. 18, 2010, pp. 2714-2717.

Extended European Search Report issued Jul. 26, 2022, in European Patent Application No. 20832139.8, citing document No. 15 therein, 5 pages.

Combined Chinese Office Action and Search Report issued Mar. 29, 2023 in Patent Application No. 202080039520.7 (with English machine translation and English translation of Category of Cited Documents), citing documents 7 and 15-19 therein, 9 pages.

Combined Taiwanese Office Action and Search Report issued Jan. 22, 2024 in Taiwanese Patent Application No. 109121638 (with unedited computer generated English translation), citing document 15 therein, 17 pages.

* cited by examiner

THERMOPLASTIC RESIN, OPTICAL FILM MADE THEREFROM, DIOL COMPOUND, DIESTER COMPOUND

CROSS-REFERENCE

This application is a Continuation of International Application No. PCT/JP2020/024490 filed on Jun. 23, 2020, which claims priority to Japanese Patent Application No. 2019-116226 filed on Jun. 24, 2019. The entire contents of which are incorporated herein by reference.

TECHNICAL FIELD

The present disclosure relates to a resin excellent in various properties such as optical property, heat resistance, and moldability; an optical film obtained by using the same; and a diol compound and a diester compound used for producing a resin.

BACKGROUND ART

Recently, demands for optical transparent resins for use in optical systems such as optical lenses, optical films, and optical recording media have increased. Among them, various optical films have been developed and used for the purpose of improving contrast or tinting or enhancing display quality such as increase in viewing angle and prevention of external light reflection because thin flat panel displays (FPDs) typified by liquid crystal displays and organic EL displays have particularly remarkably become popular.

Organic EL displays use ¼ wavelength plates for preventing external light reflection. In order to prevent tinting and achieve clear black display, retardation films used for ¼ wavelength plates are required to have broadband wavelength dispersion properties (reverse wavelength dispersion property) that make it possible to obtain ideal retardation properties at each wavelength in the visible region.

As such a retardation film, a broadband retardation film is disclosed which is obtained by, for example, laminating two kinds of retardation films different in wavelength dispersion of birefringence so that their respective slow axes are orthogonal to each other (Patent Literature 1). Further, another method for obtaining such a broadband retardation film is also disclosed in which a ½ wavelength plate and a ¼ wavelength plate are laminated so that their respective slow axes are arranged in a specific manner (Patent Literature 2). Further, a broadband retardation film is disclosed which is made of cellulose acetate having a specific degree of acetylation (Patent Literature 3), and a retardation film is disclosed which is made of a polycarbonate copolymer containing a bisphenol structure having a fluorene ring in its side chain and exhibits a reverse wavelength dispersion property such that the retardation decreases as the wavelength becomes shorter (Patent Literature 4).

Recently, a large number of such resins having a fluorene ring in their side chains have been reported and proposed as a material useful for optical applications due to their characteristics derived from the fluorene ring, such as optical properties and heat resistance. These resins often use monomers that are relatively easily available, such as 9,9-bis[4-(2-hydroxyethoxy)phenyl]fluorene and 9,9-bis(4-hydroxy-3-methylphenyl)fluorene (for example, Patent Literatures 5 and 6).

Further, resins having new structures have also been developed. Patent Literature 7 discloses a diamine compound having a fluorene ring in its side chain, and also discloses a stretched film of a polyimide resin using such a compound. Patent Literature 8 discloses a polycarbonate resin using a fluorene compound containing no aromatic ring on its main chain. Patent Literature 9 discloses a dihydroxy compound or diester compound having two fluorene rings in the same molecule, and also discloses a stretched film of a polycarbonate resin or polyester resin using such a compound.

CITATIONS LIST

Patent Literatures

Patent Literature 1: JP 5-27118 A
Patent Literature 2: JP 10-68816 A
Patent Literature 3: JP 2000-137116 A
Patent Literature 4: Japanese Patent No. 3325560
Patent Literature 5: Japanese Patent No. 5119250
Patent Literature 6: Japanese Patent No. 5204200
Patent Literature 7: JP 2008-112124 A
Patent Literature 8: JP 2008-222965 A
Patent Literature 9: JP 2015-25111 A

SUMMARY OF INVENTION

The field of FPDs has remarkably been growing, and therefore retardation films are further required to have improved optical performance and reduced thicknesses. Further, there have also been demands for reducing material costs and improving the productivity of each process such as film formation, stretching, or lamination. Because of that, retardation films are required to combine various properties. For example, materials for use in retardation films are required not only to have a required wavelength dispersion property but also to combine various properties such as low photoelastic coefficient, high heat resistance, melt processability, and mechanical strength, and are further required to achieve a large intrinsic birefringence, excellent flexibility and stretchability, and a high degree of molecular orientation obtained by stretching.

However, the method disclosed in Patent Literature 1 or Patent Literature 2 in which retardation films are laminated results in a thick polarizing plate. Further, there is also a problem that the productivity or yield of the polarizing plate is reduced because the retardation films must be laminated so that their slow axes are arranged in a specific manner. The retardation film disclosed in Patent Literature 3 or Patent Literature 4 has a reverse wavelength dispersion property, and broadband retardation properties can be achieved by only one sheet of the film. However, the cellulose acetate disclosed in Patent Literature 3 is poor in heat resistance, and has a problem that image spots are generated by size distortion caused by moisture absorption.

The retardation film made of a polycarbonate resin having a fluorene ring disclosed in Patent Literatures 4 to 6 is known to be useful as a retardation film exhibiting a reverse wavelength dispersion property or a circularly polarizing plate for preventing external light reflection of an image display device. However, the present inventors have found from studies that a film made of a resin using 9,9-bis(4-hydroxy-3-methylphenyl)fluorene is brittle and is therefore difficult to stretch to the extent that a high degree of orientation is achieved, and a resin using 9,9-bis[4-(2-hydroxyethoxy)phenyl]fluorene is relatively excellent in stretchability, but has a slightly high photoelastic coefficient and is poor in reliability under high temperature.

Various properties may be improved by changing a copolymerization component or adjusting the ratio. However, although 9,9-bis(4-hydroxy-3-methylphenyl)fluorene has very high heat resistance, it also has the property of making the resin brittle. For this reason, it is difficult to improve the flexibility of the resin while maintaining appropriate heat resistance. Further, in the case of 9,9-bis[4-(2-hydroxyethoxy)phenyl]fluorene, the monomer component needs to be contained in an amount of about 50 to 70 wt % in order to develop a desired reverse wavelength dispersion property, and therefore the freedom of molecular design based on copolymerization is low. For this reason, it is difficult to achieve both properties such as heat resistance and mechanical strength and optical properties.

Further, the resin disclosed in Patent Literature 8 is insufficient in properties such as reverse wavelength dispersion property, photoelastic coefficient, and heat resistance. The resin disclosed in Patent Literature 9 has a low photoelastic coefficient and a high orientation property. However, a higher orientation property is recently required to be developed to reduce the thickness of a member.

It is an object of the present disclosure to solve the above problems and to provide a resin excellent in various properties such as optical property, heat resistance and moldability, particularly a resin having a reverse wavelength dispersion property and developing a high orientation property; an optical film obtained by using such a resin; and a diol compound and a diester compound for use in producing a resin.

In order to achieve the above object, the present inventors have intensively studied, and as a result have found that a resin containing a specific structural unit exhibits excellent properties. This finding has led to the completion of the present disclosure. Specifically, the gist of the present disclosure is as follows.

[1] A thermoplastic resin having a structural unit represented by the following formula (1).

[Formula 1]

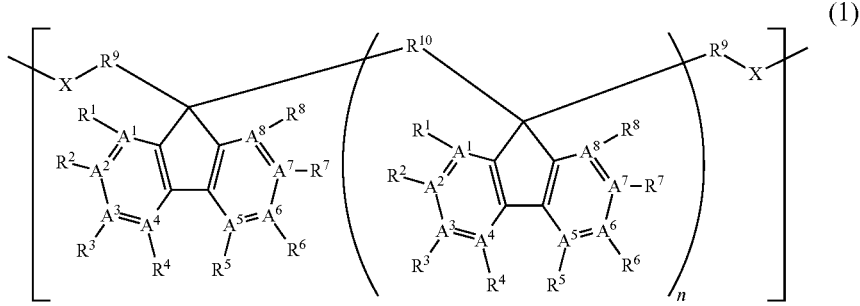

(1)

In the formula (1), $A^1$ to $A^8$ are each independently =CH— or =N—, and at least one of $A^1$ to $A^8$ is =N—. $R^1$ to $R^8$ are each independently a hydrogen atom, an optionally substituted alkyl group having 1 to 10 carbon atoms, an optionally substituted aryl group having 6 to 11 carbon atoms, an optionally substituted heteroaryl group having 3 to 10 carbon atoms, an optionally substituted acyl group having 1 to 10 carbon atoms, an optionally substituted alkoxy group having 1 to 10 carbon atoms, an optionally substituted aryloxy group having 6 to 11 carbon atoms, an optionally substituted amino group, an optionally substituted vinyl group or ethynyl group having 2 to 10 carbon atoms, a silicon atom having a substituent, a sulfur atom having a substituent, a halogen atom, a nitro group, or a cyano group, and at least two adjacent groups out of $R^1$ to $R^8$ may be bonded to each other to form a ring. $R^9$ and $R^{10}$ are each independently a direct bond or an optionally substituted alkylene group having 1 to 20 carbon atoms.

X is an oxygen atom, a carbonyl group, or an optionally substituted amino group. And n is an integer of 0 to 5.

[2] The thermoplastic resin according to [1], preferably containing the structural unit represented by the formula (1) in an amount of 1 wt % or more and 70 wt % or less.

[3] The thermoplastic resin according to [1] or [2], preferably having an absolute value of a photoelastic coefficient of $20 \times 10^{-12}$ $Pa^{-1}$ or less.

[4] The thermoplastic resin according to any one of [1] to [3], preferably having a glass transition temperature of 110° C. or more and 160° C. or less.

[5] The thermoplastic resin according to any one of [1] to [4], being preferably at least one selected from the group consisting of a polycarbonate, a polyester, and a polyester carbonate.

[6] The thermoplastic resin according to any one of [1] to [5], preferably further containing at least one of a structural unit represented by the following formula (10) and a structural unit represented by the following formula (11).

[Formula 2]

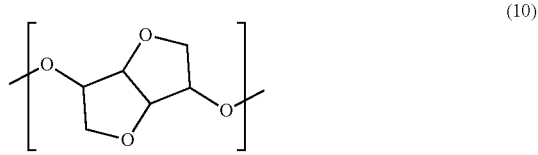

(10)

-continued

[Formula 3]

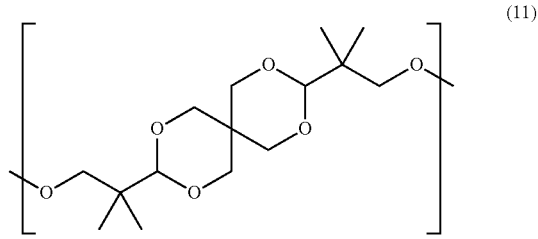

(11)

[7] The thermoplastic resin according to any one of [1] to [6], wherein the structural unit represented by the formula (1) is preferably at least one selected from the group consisting of the following formula (V-1), the following formula (V-2), and the following formula (V-3).

[Formula 4]

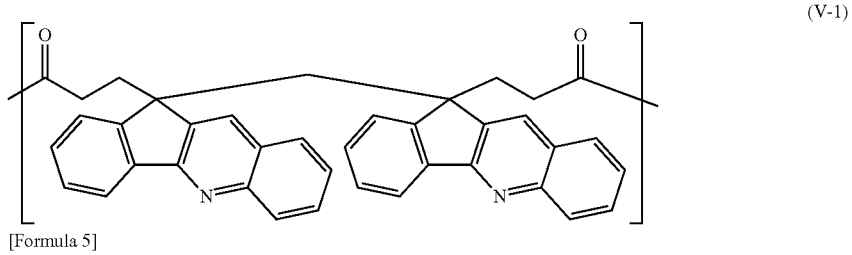

(V-1)

[Formula 5]

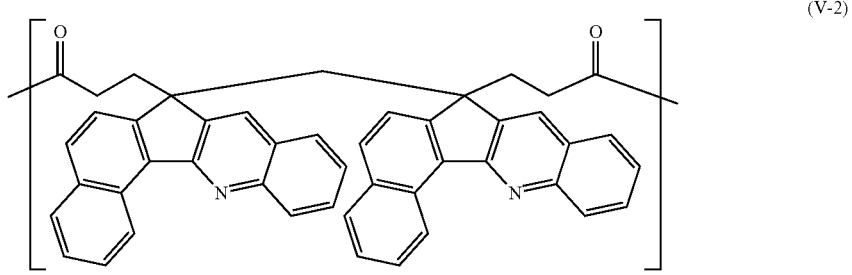

(V-2)

[Formula 6]

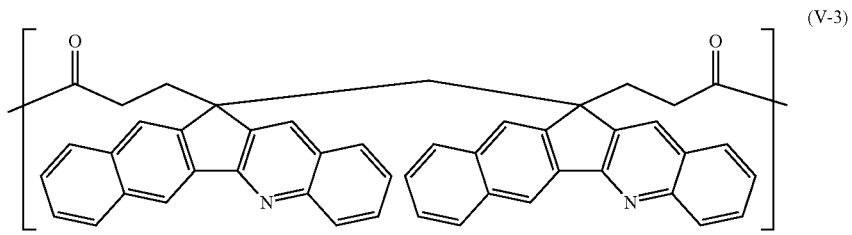

(V-3)

[8] A transparent film containing the resin according to any one of {1] to [7].

[9] A retardation film having the transparent film according to [8] stretched in at least one direction.

[10] The retardation film according to [9], wherein a ratio between a retardation at a wavelength of 450 nm (R450) and a retardation at a wavelength of 550 nm (R550) (R450/R550) preferably satisfies the following formula (I).

$$0.50 \leq R450/R550 \leq 1.02 \quad (I)$$

[11] A circularly polarizing plate including the retardation film according to [9] or [10].

[12] A diol compound represented by the following general formula (7).

[Formula 7]

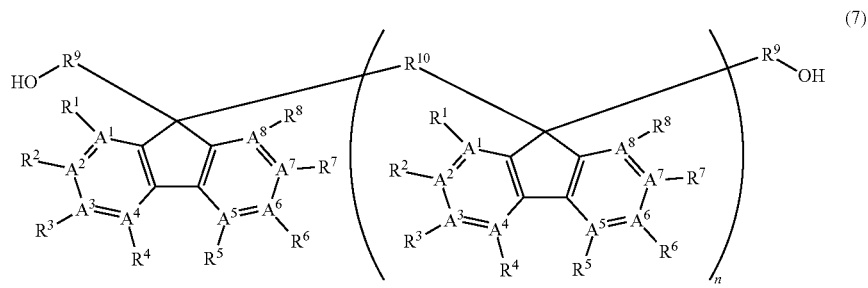

(7)

In the formula (7), $A^1$ to $A^8$ are each independently =CH— or =N—, and at least one of $A^1$ to $A^8$ is =N—. $R^1$ to $R^8$ are each independently a hydrogen atom, an optionally substituted alkyl group having 1 to 10 carbon atoms, an optionally substituted aryl group having 6 to 11 carbon atoms, an optionally substituted heteroaryl group having 3 to 10 carbon atoms, an optionally substituted acyl group having 1 to 10 carbon atoms, an optionally substituted alkoxy group having 1 to 10 carbon atoms, an optionally substituted aryloxy group having 6 to 11 carbon atoms, an optionally substituted amino group, an optionally substituted vinyl group or ethynyl group having 2 to 10 carbon atoms, a silicon atom having a substituent, a sulfur atom having a substituent, a halogen atom, a nitro group, or a cyano group, and at least two adjacent groups out of $R^1$ to $R^8$ may be bonded to each other to form a ring. $R^9$ and $R^{10}$ are each independently a direct bond or an optionally substituted alkylene group having 1 to 20 carbon atoms. And n is an integer of 0 to 5.

[13] The diol compound according to [12], wherein the formula (7) is preferably at least one of the following formula (W-1) and the following formula (W-2).

[Formula 8]

(W-1)

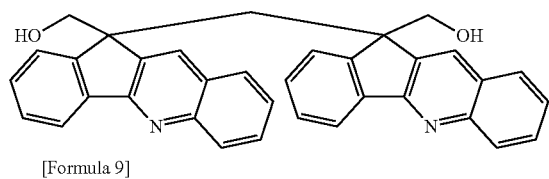

[Formula 9]

(W-2)

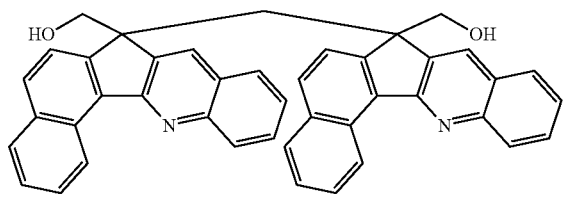

[14] A diester compound represented by the following general formula (8).

[Formula 10]

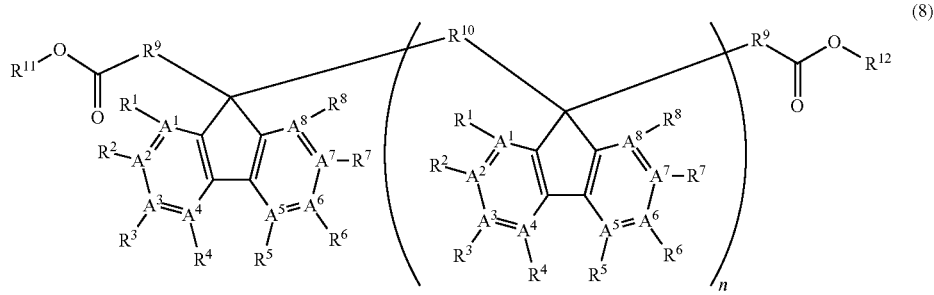

(8)

In the formula (8), $A^1$ to $A^8$ are each independently =CH— or =N—, and at least one of $A^1$ to $A^8$ is =N—. $R^1$ to $R^8$ are each independently a hydrogen atom, an optionally substituted alkyl group having 1 to 10 carbon atoms, an optionally substituted aryl group having 6 to 11 carbon atoms, an optionally substituted heteroaryl group having 3 to 10 carbon atoms, an optionally substituted acyl group having 1 to 10 carbon atoms, an optionally substituted alkoxy group having 1 to 10 carbon atoms, an optionally substituted aryloxy group having 6 to 11 carbon atoms, an optionally substituted amino group, an optionally substituted vinyl group or ethynyl group having 2 to 10 carbon atoms, a silicon atom having a substituent, a sulfur atom having a substituent, a halogen atom, a nitro group, or a cyano group, and at least two adjacent groups out of $R^1$ to $R^8$ may be bonded to each other to form a ring. $R^9$ and $R^{10}$ are each independently a direct bond or an optionally substituted alkylene group having 1 to 20 carbon atoms. $R^{11}$ and $R^{12}$ are each a hydrogen atom, an optionally substituted aryl group having 6 to 11 carbon atoms, an optionally substituted heteroaryl group having 3 to 10 carbon atoms, or an optionally substituted alkyl group having 1 to 10 carbon atoms, $R^{11}$ and $R^{12}$ may be the same or different from each other. And n is an integer of 0 to 5.

[15] The diester compound according to [14], wherein the formula (8) is preferably at least one of the following formula (X-1) and the following formula (X-2).

[Formula 11]

(X-1)

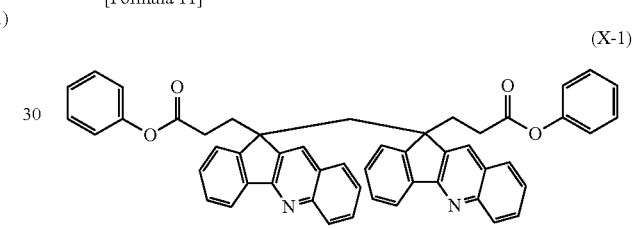

[Formula 12]

(X-2)

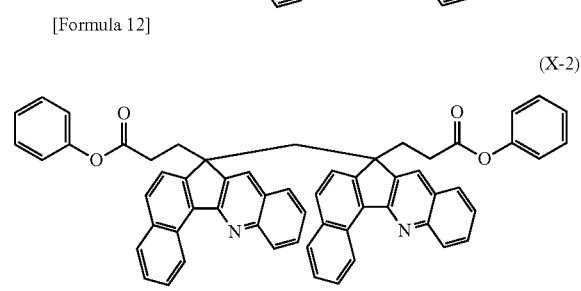

The resin according to the present disclosure has an excellent balance among various properties such as optical property, heat resistance and moldability. Therefore, the resin according to the present disclosure can suitably be used for optical films such as retardation films. The resin according to the present disclosure can particularly suitably be used for ¼ wavelength plates and ½ wavelength plates required to have broadband performance. Further, the resin according to the present disclosure is excellent in orientation property, which makes it possible to further reduce the thickness of an optical film.

DESCRIPTION OF EMBODIMENTS

Embodiments of the present disclosure will be described in detail below, but the following description of components is an example (representative example) of the embodiment of the present disclosure, and the present disclosure is not limited to the following contents as long as it does not go beyond the gist thereof. It is to be noted that in the present disclosure, the "structural unit" refers to a partial structure sandwiched between adjacent linking groups in a polymer as well as a partial structure sandwiched between a polymerization reactive group present in the end of a polymer and a linking group adjacent to the polymerization reactive group. Further, in the present disclosure, the "repeating structural unit" refers to a structural unit including the structural unit described above and a linking group adjacent thereto.

The resin according to the present disclosure is a thermoplastic resin having a structural unit represented by the following formula (1). It is to be noted that in this description, the structural unit represented by the formula (1) is sometimes referred to as a "structural unit (a)".

[Structural Unit (a)]

The structural unit (a) includes an azafluorene ring in which $A^1$ to $A^8$ are each independently =CH— or =N—, and at least one of $A^1$ to $A^8$ is =N—. The number of nitrogen atoms contained in $A^1$ to $A^8$ is preferably 2 or less, more preferably 1. When $A^1$ to $A^8$ contain a nitrogen atom, it is possible, particularly when the resin according to the present disclosure is used as a reverse wavelength dispersive retardation film, to develop a high intrinsic birefringence and a high orientation property (birefringence) obtained by stretching. On the other hand, if the number of nitrogen atoms is too large, the water absorption rate of the resin according to the present disclosure containing the structural unit (a) increases so that the dimensional stability of a molded article may deteriorate.

The position of =N— in $A^1$ to $A^8$ is not particularly limited, but it is preferred that at least one selected from the group consisting of $A^1$, $A^4$, $A^5$, and $A^8$ is =N—, and it is more preferred that at least one of $A^4$ and $A^5$ is =N—. In this case, it is possible, particularly when the resin according to the present disclosure is used as a reverse wavelength dispersive retardation film, to develop a higher intrinsic birefringence.

In the structural unit (a), $R^1$ to $R^8$ are each independently a hydrogen atom, an optionally substituted alkyl group having 1 to 10 carbon atoms, an optionally substituted aryl group having 6 to 11 carbon atoms, an optionally substituted heteroaryl group having 3 to 10 carbon atoms, an optionally

[Formula 13]

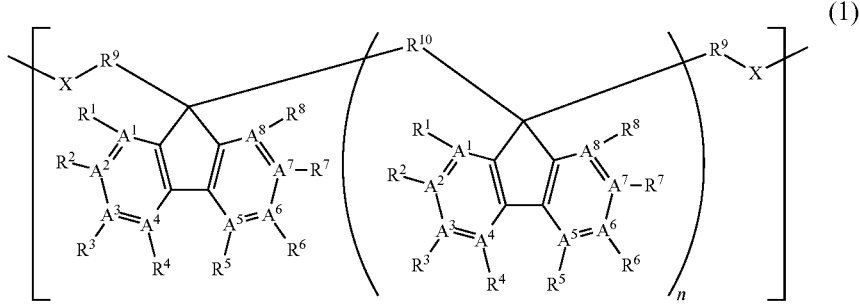

(1)

In the formula (1), $A^1$ to $A^8$ are each independently =CH— or =N—, and at least one of $A^1$ to $A^8$ is =N—. $R^1$ to $R^8$ are each independently a hydrogen atom, an optionally substituted alkyl group having 1 to 10 carbon atoms, an optionally substituted aryl group having 6 to 11 carbon atoms, an optionally substituted heteroaryl group having 3 to 10 carbon atoms, an optionally substituted acyl group having 1 to 10 carbon atoms, an optionally substituted alkoxy group having 1 to 10 carbon atoms, an optionally substituted aryloxy group having 6 to 11 carbon atoms, an optionally substituted amino group, an optionally substituted vinyl group having 2 to 10 carbon atoms, an optionally substituted ethynyl group having 2 to 10 carbon atoms, a silicon atom having a substituent, a sulfur atom having a substituent, a halogen atom, a nitro group, or a cyano group, and at least two adjacent groups out of $R^1$ to $R^8$ may be bonded to each other to form a ring. $R^9$ and $R^{10}$ are each independently a direct bond or an optionally substituted alkylene group having 1 to 20 carbon atoms.

X is an oxygen atom, a carbonyl group, or an optionally substituted amino group. And n is an integer of 0 to 5.

substituted acyl group having 1 to 10 carbon atoms, an optionally substituted alkoxy group having 1 to 10 carbon atoms, an optionally substituted aryloxy group having 6 to 11 carbon atoms, an optionally substituted amino group, an optionally substituted vinyl group having 2 to 10 carbon atoms, an optionally substituted ethynyl group having 2 to 10 carbon atoms, a silicon atom having a substituent, a sulfur atom having a substituent, a halogen atom, a nitro group, or a cyano group. At least two adjacent groups out of $R^1$ to $R^8$ may be bonded to each other to form a ring.

Specific examples of the structure of $R^1$ to $R^8$ include, but are not limited to, the following. Examples of the optionally substituted alkyl group having 1 to 10 carbon atoms include: linear alkyl groups such as a methyl group, an ethyl group, an n-propyl group, an n-butyl group, an n-pentyl group, an n-hexyl group, and an n-decyl group; alkyl groups having a branched chain, such as an isopropyl group, a 2-methylpropyl group, a 2,2-dimethylpropyl group, and a 2-ethylhexyl group; and cyclic alkyl groups such as a cyclopropyl group, a cyclopentyl group, a cyclohexyl group, and a cyclooctyl group. The number of carbon atoms in the optionally substituted alkyl group having 1 to 10 carbon atoms is preferably 4 or less, more preferably 2 or less. When the number of carbon atoms is within the above range, steric hindrance between azafluorene rings is less likely to occur, and therefore desired optical properties derived from the azafluorene ring tend to be achieved.

Examples of a substituent that the alkyl group may have include: halogen atoms (e.g., a fluorine atom, a chlorine atom, a bromine atom, an iodine atom); alkoxy groups having 1 to 10 carbon atoms (e.g., a methoxy group, an ethoxy group); acyl groups having 1 to 10 carbon atoms (e.g., an acetyl group, a benzoyl group); acylamino groups having 1 to 10 carbon atoms (e.g., an acetamide group, a benzoylamide group); a nitro group; a cyano group; and aryl groups having 6 to 11 carbon atoms (e.g., a phenyl group, a naphthyl group) that may have at least one substituent selected from the group consisting of halogen atoms (e.g., a fluorine atom, a chlorine atom, a bromine atom, an iodine atom), alkyl groups having 1 to 10 carbon atoms (e.g., a methyl group, an ethyl group, an isopropyl group), alkoxy groups having 1 to 10 carbon atoms (e.g., a methoxy group, an ethoxy group), acyl groups having 1 to 10 carbon atoms (e.g., an acetyl group, a benzoyl group), acylamino groups having 1 to 10 carbon atoms (e.g., an acetamide group, a benzoylamide group), a nitro group, and a cyano group. The number of the substituents is not particularly limited, but is preferably 1 to 3. When there are two or more substituents, the substituents may be the same or different from each other. From the viewpoint of enabling inexpensive industrial production, the alkyl group is preferably unsubstituted.

Examples of the optionally substituted aryl group having 6 to 11 carbon atoms include aryl groups such as a phenyl group, a 1-naphthyl group, and a 2-naphthyl group. The number of carbon atoms in the optionally substituted aryl group having 6 to 11 carbon atoms is preferably 8 or less, more preferably 7 or less. When the number of carbon atoms is within the above range, steric hindrance between azafluorene rings is less likely to occur, and therefore desired optical properties derived from the azafluorene ring tend to be achieved.

Examples of a substituent that the aryl group may have include: alkyl groups having 1 to 10 carbon atoms (e.g., a methyl group, an ethyl group, an isopropyl group); halogen atoms (e.g., a fluorine atom, a chlorine atom, a bromine atom, an iodine atom); alkoxy groups having 1 to 10 carbon atoms (e.g., a methoxy group, an ethoxy group); acyl groups having 1 to 10 carbon atoms (e.g., an acetyl group, a benzoyl group); acylamino groups having 1 to 10 carbon atoms (e.g., an acetamide group, a benzoylamide group); a nitro group; a cyano group; and aryl groups having 6 to 11 carbon atoms (e.g., a phenyl group, a naphthyl group) that may have at least one substituent selected from the group consisting of halogen atoms (e.g., a fluorine atom, a chlorine atom, a bromine atom, an iodine atom), alkyl groups having 1 to 10 carbon atoms (e.g., a methyl group, an ethyl group, an isopropyl group), alkoxy groups having 1 to 10 carbon atoms (e.g., a methoxy group, an ethoxy group), acyl groups having 1 to 10 carbon atoms (e.g., an acetyl group, a benzoyl group), acylamino groups having 1 to 10 carbon atoms (e.g., an acetamide group, a benzoylamide group), a nitro group, and a cyano group. The number of the substituents is not particularly limited, but is preferably 1 to 3. When there are two or more substituents, the substituents may be the same or different from each other. From the viewpoint of enabling inexpensive industrial production, the aryl group is preferably unsubstituted.

Examples of the optionally substituted heteroaryl group having 3 to 10 carbon atoms include heteroaryl groups such as an imidazoyl group, a 2-pyridyl group, a 2-thienyl group, and a 2-furyl group. The number of carbon atoms in the optionally substituted heteroaryl group having 3 to 10 carbon atoms is preferably 8 or less, more preferably 6 or less. When the number of carbon atoms is within the above range, steric hindrance between azafluorene rings is less likely to occur, and therefore desired optical properties derived from the azafluorene ring tend to be achieved.

Examples of a substituent that the heteroaryl group may have include: alkyl groups having 1 to 10 carbon atoms (e.g., a methyl group, an ethyl group, an isopropyl group); halogen atoms (e.g., a fluorine atom, a chlorine atom, a bromine atom, an iodine atom); alkoxy groups having 1 to 10 carbon atoms (e.g., a methoxy group, an ethoxy group); acyl groups having 1 to 10 carbon atoms (e.g., an acetyl group, a benzoyl group); acylamino groups having 1 to 10 carbon atoms (e.g., an acetamide group, a benzoylamide group); a nitro group; a cyano group; and aryl groups having 6 to 11 carbon atoms (e.g., a phenyl group, a naphthyl group) that may have at least one substituent selected from the group consisting of halogen atoms (e.g., a fluorine atom, a chlorine atom, a bromine atom, an iodine atom), alkyl groups having 1 to 10 carbon atoms (e.g., a methyl group, an ethyl group, an isopropyl group), alkoxy groups having 1 to 10 carbon atoms (e.g., a methoxy group, an ethoxy group), acyl groups having 1 to 10 carbon atoms (e.g., an acetyl group, a benzoyl group), acylamino groups having 1 to 10 carbon atoms (e.g., an acetamide group, a benzoylamide group), a nitro group, and a cyano group. The number of the substituents is not particularly limited, but is preferably 1 to 3. When there are two or more substituents, the substituents may be the same or different from each other. From the viewpoint of enabling inexpensive industrial production, the heteroaryl group is preferably unsubstituted.

Examples of the optionally substituted acyl group having 1 to 10 carbon atoms include: aliphatic acyl groups such as a formyl group, an acetyl group, a propionyl group, a 2-methylpropionyl group, a 2,2-dimethylpropionyl group, and a 2-ethylhexanoyl group; and aromatic acyl groups such as a benzoyl group, a 1-naphthylcarbonyl group, a 2-naphthylcarbonyl group, and a 2-furylcarbonyl group. The number of carbon atoms in the optionally substituted acyl group having 1 to 10 carbon atoms is preferably 4 or less, more preferably 2 or less. When the number of carbon atoms is within the above range, steric hindrance between azafluorene rings is less likely to occur, and therefore desired optical properties derived from the azafluorene ring tend to be achieved.

Examples of a substituent that the acyl group may have include: halogen atoms (e.g., a fluorine atom, a chlorine atom, a bromine atom, an iodine atom); alkyl groups having 1 to 10 carbon atoms (e.g., a methyl group, an ethyl group, an isopropyl group); alkoxy groups having 1 to 10 carbon atoms (e.g., a methoxy group, an ethoxy group); acylamino groups having 1 to 10 carbon atoms (e.g., an acetamide group, a benzoylamide group); a nitro group; a cyano group; and aryl groups having 6 to 11 carbon atoms (e.g., a phenyl group, a naphthyl group) that may have at least one substituent selected from the group consisting of halogen atoms (e.g., a fluorine atom, a chlorine atom, a bromine atom, an iodine atom), alkyl groups having 1 to 10 carbon atoms (e.g., a methyl group, an ethyl group, an isopropyl group), alkoxy groups having 1 to 10 carbon atoms (e.g., a methoxy group, an ethoxy group), acyl groups having 1 to 10 carbon atoms (e.g., an acetyl group, a benzoyl group), acylamino groups having 1 to 10 carbon atoms (e.g., an acetamide group, a benzoylamide group), a nitro group, and a cyano group. The number of the substituents is not particularly limited, but is preferably 1 to 3. When there are two or more substituents, the substituents may be the same or different from each other. From the viewpoint of enabling inexpensive industrial production, the acyl group is preferably unsubstituted.

Examples of the optionally substituted alkoxy group having 1 to 10 carbon atoms include: alkoxy groups such as a methoxy group, an ethoxy group, an isopropoxy group, and a t-butoxy group; and an acyloxy group such as an acetoxy group. The number of carbon atoms in the optionally substituted alkoxy group having 1 to 10 carbon atoms is preferably 4 or less, more preferably 2 or less. When the number of carbon atoms is within the above range, steric hinderance between azafluorene rings is less likely to occur, and therefore desired optical properties derived from the azafluorene ring tend to be achieved.

Examples of a substituent that the alkoxy group may have include: halogen atoms (e.g., a fluorine atom, a chlorine atom, a bromine atom, an iodine atom); alkoxy groups having 1 to 10 carbon atoms (e.g., a methoxy group, an ethoxy group); acyl groups having 1 to 10 carbon atoms (e.g., an acetyl group, a benzoyl group); acylamino groups having 1 to 10 carbon atoms (e.g., an acetamide group, a benzoylamide group); a nitro group; a cyano group; and aryl groups having 6 to 11 carbon atoms (e.g., a phenyl group, a naphthyl group) that may have at least one substituent selected from the group consisting of halogen atoms (e.g., a fluorine atom, a chlorine atom, a bromine atom, an iodine atom), alkyl groups having 1 to 10 carbon atoms (e.g., a methyl group, an ethyl group, an isopropyl group), alkoxy groups having 1 to 10 carbon atoms (e.g., a methoxy group, an ethoxy group), acyl groups having 1 to 10 carbon atoms (e.g., an acetyl group, a benzoyl group), acylamino groups having 1 to 10 carbon atoms (e.g., an acetamide group, a benzylamide group), a nitro group, and a cyano group. The number of the substituents is not particularly limited, but is preferably 1 to 3. When there are two or more substituents, the substituents may be the same or different from each other. From the viewpoint of enabling inexpensive industrial production, the alkoxy group is preferably unsubstituted.

Examples of the optionally substituted aryloxy group having 6 to 11 carbon atoms include a phenoxy group, a 1-naphthyloxy group, and a 2-naphthyloxy group. The number of carbon atoms in the optionally substituted aryloxy group having 6 to 11 carbon atoms is preferably 8 or less, more preferably 7 or less. When the number of carbon atoms is within the above range, steric hinderance between azafluorene rings is less likely to occur, and therefore desired optical properties derived from the azafluorene ring tend to be achieved.

Examples of a substituent that the aryloxy group may have include: alkyl groups having 1 to 10 carbon atoms (e.g., a methyl group, an ethyl group, an isopropyl group); halogen atoms (e.g., a fluorine atom, a chlorine atom, a bromine atom, an iodine atom); alkoxy groups having 1 to 10 carbon atoms (e.g., a methoxy group, an ethoxy group); acyl groups having 1 to 10 carbon atoms (e.g., an acetyl group, a benzoyl group); acylamino groups having 1 to 10 carbon atoms (e.g., an acetamide group, a benzoylamide group); a nitro group; a cyano group; and aryl groups having 6 to 11 carbon atoms (e.g., a phenyl group, a naphthyl group) that may have at least one substituent selected from the group consisting of halogen atoms (e.g., a fluorine atom, a chlorine atom, a bromine atom, an iodine atom), alkyl groups having 1 to 10 carbon atoms (e.g., a methyl group, an ethyl group, an isopropyl group), alkoxy groups having 1 to 10 carbon atoms (e.g., a methoxy group, an ethoxy group), acyl groups having 1 to 10 carbon atoms (e.g., an acetyl group, a benzoyl group), acylamino groups having 1 to 10 carbon atoms (e.g., an acetamide group, a benzoylamide group), a nitro group, and a cyano group. The number of the substituents is not particularly limited, but is preferably 1 to 3. When there are two or more substituents, the substituents may be the same or different from each other. From the viewpoint of enabling inexpensive industrial production, the aryloxy group is preferably unsubstituted.

Examples of the optionally substituted amino group include: an amino group; aliphatic amino groups such as an N-methylamino group, an N,N-dimethylamino group, an N-ethylamino group, an N,N-diethylamino group, an N,N-methylethylamino group, an N-propylamino group, an N,N-dipropylamino group, an N-isopropylamino group, and an N,N-diisopropylamino group; aromatic amino groups such as an N-phenylamino group and an N,N-diphenylamino group; acylamino groups such as a formamide group, an acetamide group, a decanoylamide group, a benzoylamide group, and a chloroacetamide group; and alkoxycarbonylamino groups such as a benzyloxycarbonylamino group and a tert-butyloxycarbonylamino group. Among them, an N,N-dimethylamino group, an N-ethylamino group, or an N,N-diethylamino group is preferred, and an N,N-dimethylamino group is more preferred because they have no proton having a high acidity, have a low molecular weight, and tend to allow the ratio of azafluorene rings in an optical material to increase.

Examples of a substituent that the amino group may have include: halogen atoms (e.g., a fluorine atom, a chlorine atom, a bromine atom, an iodine atom); alkoxy groups having 1 to 10 carbon atoms (e.g., a methoxy group, an ethoxy group); acyl groups having 1 to 10 carbon atoms (e.g., an acetyl group, a benzoyl group); acylamino groups having 1 to 10 carbon atoms (e.g., an acetamide group, a benzoylamide group); a nitro group; a cyano group; and aryl groups having 6 to 11 carbon atoms (e.g., a phenyl group, a naphthyl group) that may have at least one substituent selected from the group consisting of halogen atoms (e.g., a fluorine atom, a chlorine atom, a bromine atom, an iodine atom), alkyl groups having 1 to 10 carbon atoms (e.g., a methyl group, an ethyl group, an isopropyl group), alkoxy groups having 1 to 10 carbon atoms (e.g., a methoxy group, an ethoxy group), acyl groups having 1 to 10 carbon atoms (e.g., an acetyl group, a benzoyl group), acylamino groups having 1 to 10 carbon atoms (e.g., an acetamide group, a benzoylamide group), a nitro group, and a cyano group. The number of the substituents is not particularly limited, but is preferably 1 to 3. When there are two or more substituents, the substituents may be the same or different from each other.

Examples of the optionally substituted vinyl group having 2 to 10 carbon atoms and the optionally substituted ethynyl group having 2 to 10 carbon atoms include a vinyl group, a 2-methylvinyl group, a 2-ethylvinyl group, a 2-propylvinyl group, a 2,2-dimethylvinyl group, a 2-phenylvinyl group, a 2-acetylvinyl group, an ethynyl group, a methylethynyl group, a tert-butylethynyl group, a phenylethynyl group, an acetylethynyl group, and a trimethylsilylethynyl group. When there are two or more substituents, the substituents may be the same or different from each other. From the viewpoint of enabling inexpensive industrial production, the vinyl group and the ethynyl group are preferably unsubstituted. Among them, a vinyl group, a 2-methylvinyl group, an ethynyl group, or a 2-methylethynyl group is more preferred because they have a low molecular weight and tend to allow the ratio of azafluorene rings in an optical material to increase.

Examples of a substituent that the vinyl group and the ethynyl group may have include: halogen atoms (e.g., a fluorine atom, a chlorine atom, a bromine atom, an iodine atom); alkoxy groups having 1 to 10 carbon atoms (e.g., a methoxy group, an ethoxy group); acyl groups having 1 to 10 carbon atoms (e.g., an acetyl group, a benzoyl group); acylamino groups having 1 to 10 carbon atoms (e.g., an acetamide group, a benzoylamide group); a nitro group; a cyano group; and aryl groups having 6 to 11 carbon atoms (e.g., a phenyl group, a naphthyl group) that may have at least one substituent selected from the group consisting of halogen atoms (e.g., a fluorine atom, a chlorine atom, a bromine atom, an iodine atom), alkyl groups having 1 to 10 carbon atoms (e.g., a methyl group, an ethyl group, an isopropyl group), alkoxy groups having 1 to 10 carbon atoms (e.g., a methoxy group, an ethoxy group), acyl groups having 1 to 10 carbon atoms (e.g., an acetyl group, a benzoyl group); acylamino groups having 1 to 10 carbon atoms (e.g., an acetamide group, a benzoylamide group), a nitro group, and a cyano group. The number of the substituents is not particularly limited, but is preferably 1 to 3.

Examples of the silicon atom having a substituent include: trialkylsilyl groups such as a trimethylsilyl group and a triethylsilyl group; and trialkoxysilyl groups such as a trimethoxysilyl group and a triethoxysilyl group. Among them, trialkylsilyl groups are preferred because they can stably be handled.

Examples of the sulfur atom having a substituent include: a sulfo group; alkylsulfonyl groups such as a methylsulfonyl group, an ethylsulfonyl group, a propylsulfonyl group, and an isopropylsulfonyl group; arylsulfonyl groups such as a phenylsulfonyl group and a p-tolylsulfonyl group; alkylsulfinyl groups such as a methylsulfinyl group, an ethylsulfinyl group, a propylsulfinyl group, and an isopropylsulfinyl group; arylsulfinyl groups such as a phenylsulfinyl group and a p-tolylsulfinyl group; alkylthio groups such as a methylthio group and an ethylthio group; arylthio groups such as a phenylthio group and a p-tolylthio group; alkoxysulfonyl groups such as a methoxysulfonyl group and an ethoxysulfonyl group; an aryloxysulfonyl group such a phenoxysulfonyl group; an aminosulfonyl group; alkylsulfonyl groups such as an N-methylaminosulfonyl group, an N-ethylaminosulfonyl group, an N-tert-butylaminosulfonyl group, N,N-dimethylaminosulfonyl group, and N,N-diethylaminosulfonyl group; and arylaminosulfonyl groups such as an N-phenylaminosulfonyl group, an N,N-diphenylaminosulfonyl group. It is to be noted that the sulfo group may form a salt with lithium, sodium, potassium, magnesium, ammonium, or the like. Among them, a methylsulfinyl group, an ethylsulfinyl group, or a phenylsulfinyl group is preferred, and a methylsulfinyl group is more preferred because they have no proton having a high acidity, have a low molecular weight, and tend to allow the ratio of azafluorene rings in an optical material to increase.

Examples of the halogen atom include a fluorine atom, a chlorine atom, a bromine atom, and an iodine atom. Among them, a fluorine atom, a chlorine atom, or a bromine atom is preferred, and a chlorine atom or a bromine atom is more preferred because they can relatively easily be introduced and are electron attractive substituents, and therefore tend to increase the reactivity of methylene group of azafluorene.

It is preferred that at least two adjacent groups out of $R^1$ to $R^8$ are bonded to each other to form a ring. In this case, it is possible to further improve the optical properties of the resin. From the same viewpoint, the ring to be formed is more preferably an aromatic ring. That is, the azafluorene ring in the structural unit (a) more preferably has an aromatic ring as a condensed ring. When the structural unit (a) has an aromatic ring as a condensed ring, the π-conjugated system of the azafluorene ring can be expanded, and therefore the resin can have more excellent optical properties. From the same viewpoint, the ring to be formed more preferably contains one or more benzene ring or a six-membered aromatic ring having a hetero atom.

The azafluorene ring in the structural unit (a) preferably has only a nitrogen atom as a hetero atom (specifically, as an atom other than carbon) forming the ring. That is, the hetero atom forming the azafluorene ring is preferably a nitrogen atom. In this case, the water absorption rate of the resin can be reduced, and therefore the resin has a particularly excellent balance between optical properties and dimensional stability.

In the structural unit (a), $R^9$ and $R^{10}$ are each independently a direct bond or an optionally substituted alkylene group having 1 to 20 carbon atoms. Examples of specific structures of $R^9$ and $R^{10}$ include, but are not limited to: linear alkylene groups such as a methylene group, an ethylene group, an n-propylene group, an n-butylene group, an n-pentylene group, and n-hexylene; alkylene groups having a branched chain, such as a methylmethylene group, a dimethylmethylene group, an ethylmethylene group, a propylmethylene group, a butylmethylene group, a (1-methylethyl) methylene group, a 1-methylethylene group, a 2-methylethylene group, a 1-ethylethylene group, a 2-ethylethylene group, a 1-methylpropylene group, a 2-methylpropylene group, a 1,1-dimethylethylene group, a 2,2-dimethylpropylene group, and a 3-methylpropylene group (in $R^9$ and $R^{10}$, the position of the substituent is numbered from the carbon on the fluorene ring side); alicyclic alkylene groups having the chemical bond of a linear or branched alkylene group at any two positions in an alicyclic structure such as cyclopropane, cyclohexane, decahydronaphthalene, or adamantane; and heterocyclic alkylene groups having the chemical bond of a linear or branched alkylene group at any two positions in a heterocyclic structure such as tetrahydrofuran, tetrahydropyran, or 1,3-dioxane. It is to be noted that examples of specific structure of the chemical bond of the linear or branched alkylene group that the alicyclic structure or the heterocyclic structure has at any two positions include, but are not limited to: linear alkylene groups such as a methylene group, an ethylene group, an n-propylene group, an n-butylene group, an n-pentylene group, and n-hexylene; and alkylene groups having a branched chain, such as a 1-methylethylene group, a 2-methylethylene group, a 1-ethylethylene group, a 2-ethylethylene group, a 1-methylpropylene group, a 2-methylpropylene group, a 1,1-dimethylethylene group, a 2,2-dimethylpropylene group, a 3-methylpropylene group (here, the position of the substituent is numbered from the carbon bonded to the ring structure).

Examples of a substituent that the alkylene group may have include: halogen atoms (e.g., a fluorine atom, a chlorine atom, a bromine atom, an iodine atom); alkoxy groups having 1 to 10 carbon atoms (e.g., a methoxy group, an ethoxy group); acyl groups having 1 to 10 carbon atoms (e.g., an acetyl group, a benzoyl group); acylamino groups having 1 to 10 carbon atoms (e.g., an acetamide group, a benzoylamide group); a nitro group; a cyano group; and aryl groups having 6 to 11 carbon atoms (e.g., a phenyl group, a naphthyl group) that may have at least one substituent selected from the group consisting of halogen atoms (e.g., a fluorine atom, a chlorine atom, a bromine atom, an iodine atom), alkyl groups having 1 to 10 carbon atoms (e.g., a methyl group, an ethyl group, an isopropyl group), alkoxy groups having 1 to 10 carbon atoms (e.g., a methoxy group, an ethoxy group), acyl groups having 1 to 10 carbon atoms (e.g., an acetyl group, a benzoyl group), acylamino groups having 1 to 10 carbon atoms (e.g., an acetamide group, a benzoylamide group), a nitro group, and a cyano group. The number of the substituents is not particularly limited, but is preferably 1 to 3. When there are two or more substituents, the substituents may be the same or different from each other. From the viewpoint of enabling inexpensive industrial production, the alkylene group is preferably unsubstituted.

The selection of $R^9$ and $R^{10}$ has a particularly important effect on the development of a reverse wavelength dispersion property. The resin according to the present disclosure exhibits the strongest reverse wavelength dispersion property in a state where azafluorene rings are oriented perpendicularly to the main chain direction (e.g., stretching direction). In order to develop a strong reverse wavelength dispersion property by orienting azafluorene rings in a state close to the above-described state, $R^9$ and $R^{10}$ are preferably optionally substituted alkylene groups having 1 to 20 carbon atoms. The number of carbon atoms in the optionally substituted alkylene group having 1 to 20 carbon atoms is preferably 1 to 3. The number of carbon atoms in $R^9$ is more preferably 2 to 3, particularly preferably 2. The number of carbon atoms in $R^{10}$ is preferably 1 to 2, particularly preferably 1. If the number of carbon atoms is larger than the above range, azafluorene rings cannot be oriented in a preferred direction, and therefore there is a case where desired optical properties are not achieved. Also, if the number of carbon atoms is small, there is a case where desired optical properties are not achieved, and further, there is a fear that heat stability is impaired so that decomposition is caused by heat generated during a polymerization reaction or melt molding.

Further, when $R^9$ and $R^{10}$ are not alkylene groups but divalent aromatic groups such as arylene groups, the resin has a larger photoelastic coefficient and inferior optical properties as compared to when $R^9$ and $R^{10}$ are alkylene groups.

In the structural unit (a), X is an oxygen atom, a carbonyl group, or an optionally substituted amino group. That is, a monomer containing the structural unit (a) is any one of a dihydroxy compound, a dicarboxylic compound, a diester compound, and a diamine compound. In other words, examples of a monomer capable of forming the structural unit (a) include a dihydroxy compound, a dicarboxylic compound, a diester compound, and a diamine compound. X is preferably an oxygen atom or a carbonyl group, particularly preferably a carbonyl group. When X is a carbonyl group, the resin tends to be excellent in various properties such as heat stability, heat resistance, and reverse wavelength dispersion property.

In the structural unit (a), n is 0 to 5. n is more preferably 0 to 2, even more preferably 0 to 1, particularly preferably 1. When n is within the above range, a high-purity compound having a clear structure is easily obtained in monomer synthesis, and a resin using this compound can easily achieve heat resistance and optical properties, particularly a low photoelastic coefficient and a high development efficiency of reverse wavelength dispersion.

The azafluorene ring in the structural unit (a) preferably has, as a condensed ring, an aromatic ring formed by bonding at least two adjacent groups out of $R^1$ to $R^8$ to each other. It is more preferred that the aromatic ring is further condensed with the six-membered ring containing at least one nitrogen atom as $A^1$ to $A^8$. In this case, when there is a six-membered ring containing no nitrogen atom, the aromatic ring is particularly preferably condensed with the six-membered ring containing no nitrogen atom. The 2-conjugated system of the azafluorene ring can be expanded, and therefore the resin can have more excellent optical properties.

More specifically, it is preferred that at least one of $A^5$ and $A^8$ is =N—, $A^1$ to $A^4$, $A^6$, and $A^7$ are all =CH—, and $R^6$ and $R^7$ are bonded to each other to form an aromatic ring, and in this case, it is particularly preferred that the azafluorene ring further has, as a condensed ring, an aromatic ring formed by bonding at least two adjacent groups out of R to $R^4$ to each other. Also, it is preferred that at least one of $A^1$ and $A^4$ is =N—, $A^2$, $A^3$, and $A^5$ to $A^8$ are all =CH—, and $R^2$ and $R^3$ are bonded to each other to form an aromatic ring, and in this case, it is particularly preferred that the azafluorene ring further has, as a condensed ring, an aromatic ring formed by bonding at least two adjacent groups out of $R^5$ to $R^8$ to each other.

Specific examples of the structural unit (a) include structures shown below as group [A].

[Formula 14]

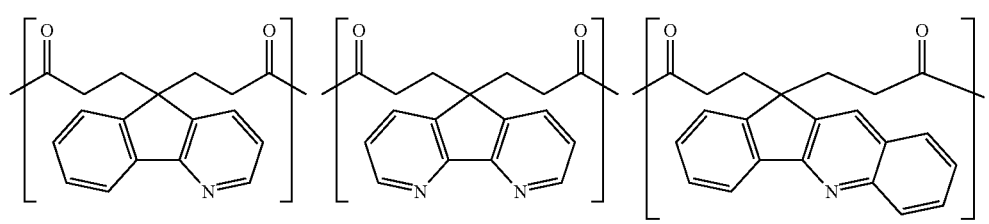

[A]

-continued
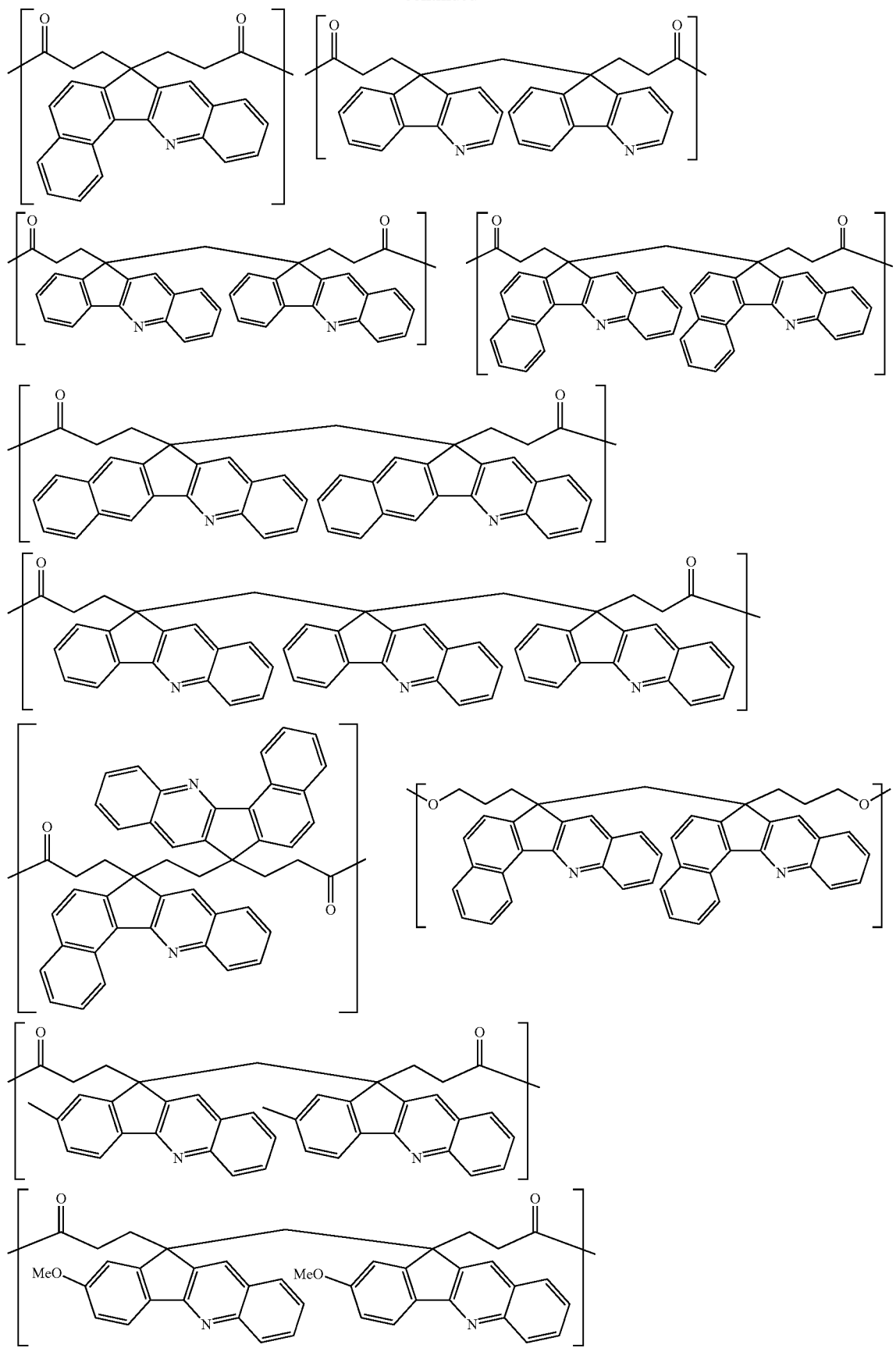

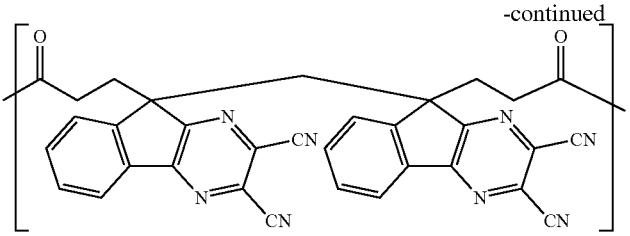

Among them, structural units shown below as group [B] are more preferred. In this case, the resin is excellent not only in optical properties but also in heat resistance, heat stability, and mechanical properties. Further, in this case, monomer synthesis can also relatively inexpensively be performed, and a high-purity monomer is easily be obtained.

[Formula 15]

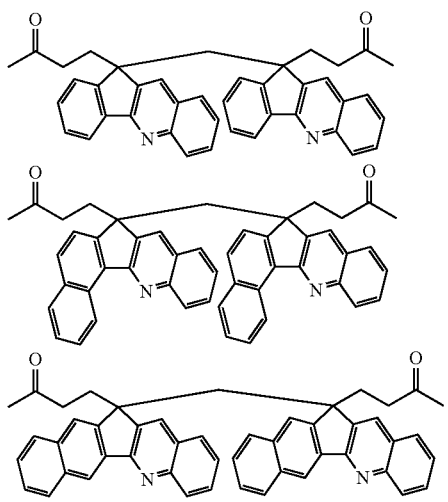

[B]

The oligofluorene structural unit in the present disclosure has characteristics described below as compared to a structural unit derived from 9,9-bis[4-(2-hydroxyethoxy)phenyl] fluorene conventionally heavily used (structural formula (4) shown below) or a structural unit derived from 9,9-bis(4-hydroxy-3-methylphenyl)fluorene (structural formula (5) shown below).

- An aromatic component, such as a phenyl group, conventionally incorporated into the main chain of a polymer is not incorporated thereinto, which makes it possible to reduce photoelastic coefficient.
- The aromatic component incorporated into the main chain exhibits a positive wavelength dispersion property such that the birefringence increases as the wavelength becomes shorter, and therefore a reverse wavelength dispersion property derived from a fluorene ring in the side chain is canceled out so that the reverse wavelength dispersion property of the resin reduces as a whole. On the other hand, when the aromatic component is not incorporated into the main chain, a reverse wavelength dispersion property can more strongly be developed.
- By changing the fluorene ring in the side chain to an azafluorene ring, a reverse wavelength dispersion property can more strongly be developed.
- By introducing two (aza)flurorene rings into the structural unit, high heat resistance and low photoelastic coefficient can be imparted to the resin.
- The main chain is constituted from a flexible alkylene chain, which makes it possible to impart flexibility and melt processability to the resin.

[Formula 16]

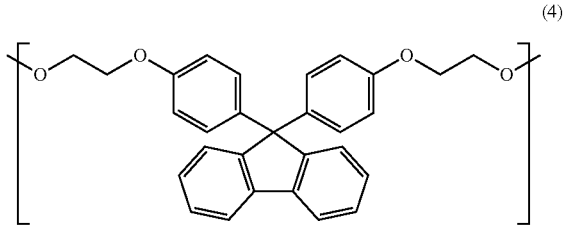

(4)

[Formula 17]

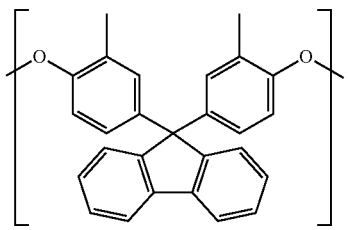

(5)

[Resin According to Present Disclosure]

The resin according to the present disclosure is a thermoplastic resin containing the structural unit (a). The resin is preferably a polycondensed or polyadditive thermoplastic resin. Specific examples thereof include resins having at least one bond selected from the group consisting of a carbonate bond, an ester bond, an amide bond, an ether bond, a urethane bond, a urea bond, and an imide bond, that is, a polycarbonate, a polyester, a polyamide, a polyether, an epoxy, a polyurethane, and a polyimide. The resin is more preferably a polycondensed thermoplastic resin, and examples thereof include resins having at least one bond selected from the group consisting of a carbonate bond, an ester bond, an amide bond, and an imide bond, that is, a polycarbonate, a polyester, a polyamide, and a polyimide. The resin is even more preferably a resin having a carbonate bond and/or an ester bond, that is, a polycarbonate, a polyester, or a polyester carbonate. These resins are excellent in heat resistance, mechanical properties, and melt processability. Further, there is an advantage that various physical properties such as optical property, heat resistance, and mechanical properties can easily be controlled within their respective desired ranges by copolymerizing a plurality of monomers including a monomer as a raw material of the structural unit (a).

The structural unit (a) according to the present disclosure may be introduced into the resin by polymerizing a diol, a dicarboxylic acid, a diester, or a diamine having the structural unit (a) in the molecular structure thereof with another diol or diester, an isocyanate, an epoxy, or the like. More specifically, a polycarbonate can be obtained by polymerizing a diol in combination with a diester carbonate represented by the following formula (6). A polyester can be obtained by polymerizing a diol in combination with a diester. A polyester carbonate can be obtained by polymerizing a diol in combination with a diester and a diester carbonate.

[Formula 18]

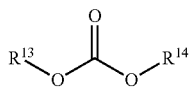

(6)

In the formula (6), $R^{13}$ and $R^{14}$ are each an optionally substituted aryl group having 6 to 11 carbon atoms, an optionally substituted heteroaryl group having 3 to 10 carbon atoms, or an optionally substituted alkyl group having 1 to 10 carbon atoms. $R^{13}$ and $R^{14}$ may be the same or different from each other.

Examples of the monomer as a raw material of the structural unit (a) include a diol represented by the following formula (7) and a diester represented by the following formula (8). It is to be noted that the diol represented by the formula (7) or the diester represented by the formula (8) is sometimes referred to as an "azafluorene monomer".

stituted alkyl group having 1 to 10 carbon atoms. $R^{11}$ and $R^{12}$ may be the same or different from each other. From the viewpoint of easy synthesis, $R^{11}$ and $R^{12}$ are preferably the same.

Among them, the specific diester represented by the formula (8) is preferably used. The specific diester is relatively superior in heat stability to the specific diol represented by the formula (7), and azafluorene rings in the polymer are oriented in a preferred direction so that a stronger reverse wavelength dispersion property tends to be exhibited.

Comparing a polycarbonate and a polyester, a polycarbonate obtained by polymerization of a diol and a diester carbonate tends to have a better balance between heat resistance and mechanical properties. Therefore, the resin according to the present disclosure is particularly preferably a polyester carbonate obtained by incorporating the specific diester having the structural unit (a) into a polycarbonate.

When $R^{11}$ and $R^{12}$ in the formula (8) are each a hydrogen atom or an alkyl group such as a methyl group or an ethyl group, there is a case where a polymerization reaction is less likely to occur under polymerization conditions usually used for polycarbonate. For this reason, $R^{11}$ and $R^{12}$ in the formula (8) are preferably aryl groups.

When n is 0 in the diol represented by the formula (7), $R^9$ is preferably an optionally substituted alkylene group having 1 to 20 carbon atoms. In this case, the diol represented by the formula (7) is excellent in stability, and therefore there is no fear that the diol is decomposed by heat generated during resin polymerization so that a resin cannot be obtained. From the same viewpoint, when n is 0, $R^9$ is more preferably an optionally substituted alkylene group having 1 to 3

[Formula 13]

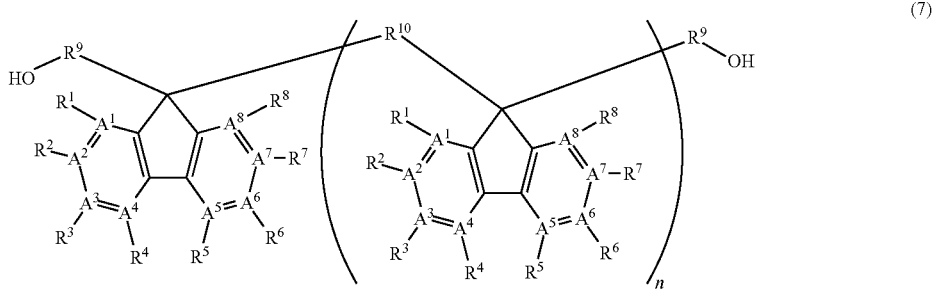

(7)

[Formula 20]

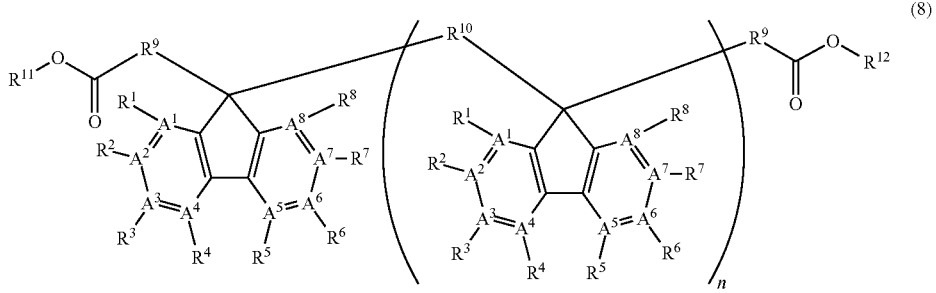

(8)

In the formula (7) or (8), $A^1$ to $A^8$, $R^1$ to $R^{10}$, and n are the same as those in the formula (1). $R^{11}$ and $R^{12}$ are each a hydrogen atom, an optionally substituted aryl group having 6 to 11 carbon atoms, an optionally substituted heteroaryl group having 3 to 10 carbon atoms, or an optionally subcarbon atoms, even more preferably an optionally substituted alkylene group having 2 to 3 carbon atoms.

When a polymerization reaction is performed using also the diester carbonate represented by the formula (6), $R^{13}$ and $R^{14}$ in the formula (6) and $R^{11}$ and $R^{12}$ in the formula (8) all preferably have the same structure. In this case, the same component is eliminated from the diester carbonate represented by the formula (6) and the diester represented by the formula (8) during the polymerization reaction, and therefore the eliminated component is easily collected and reused. Further, from the viewpoint of polymerization reactivity and usability in reuse, $R^{11}$ to $R^{14}$ are particularly preferably phenyl groups. When $R^{11}$ to $R^{14}$ are phenyl groups, a component eliminated during the polymerization reaction is phenol.

Specific examples of the azafluorene ring in the formula (7) or (8) include structures shown below as group [I].

[Formula 21]

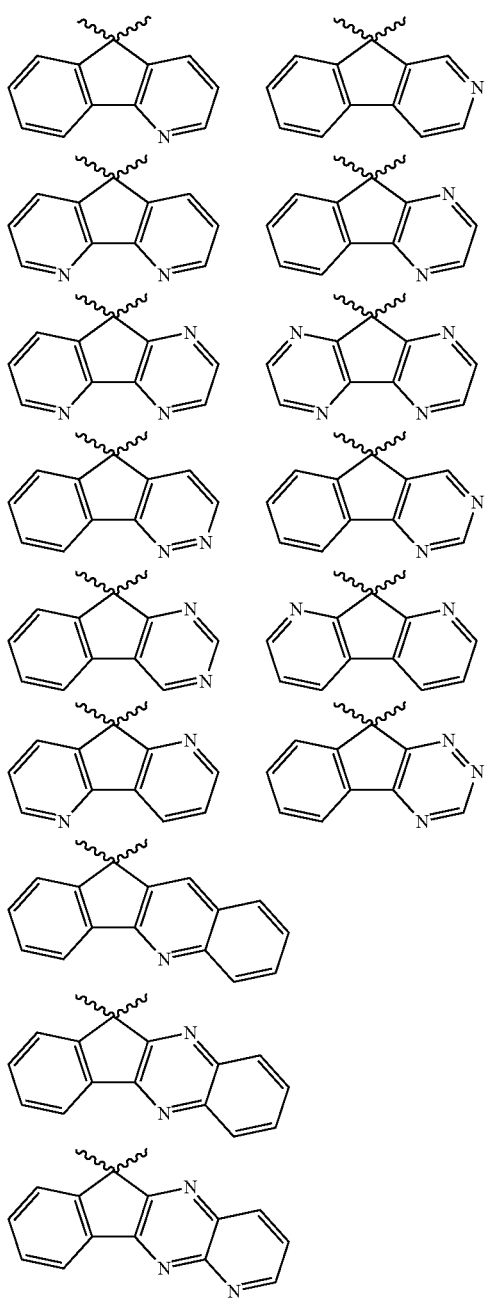

[L]

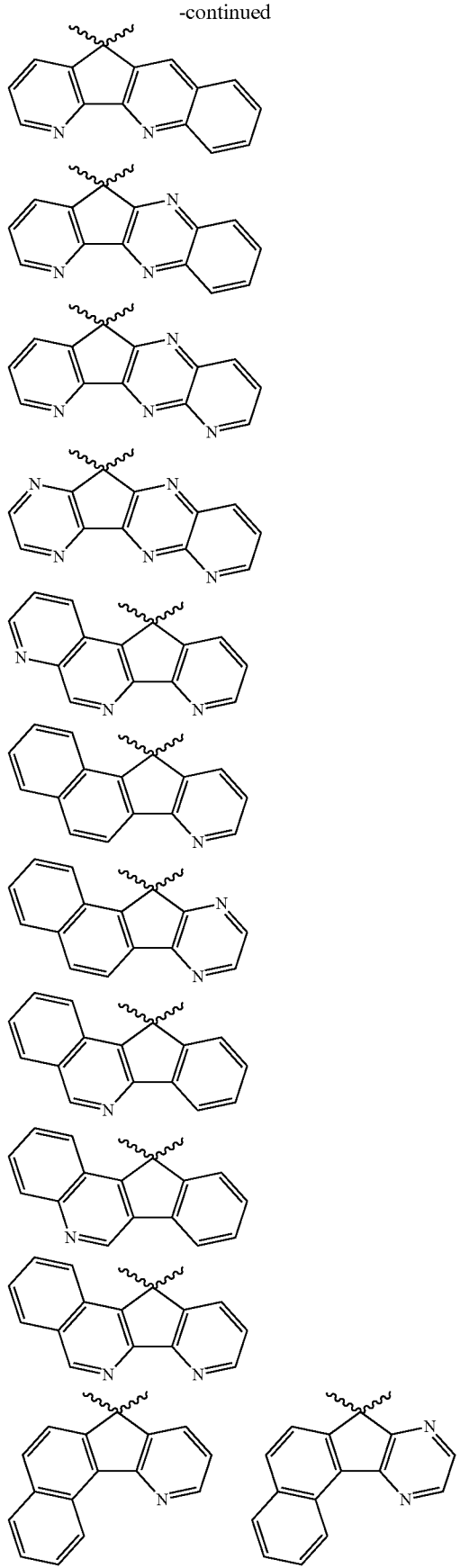

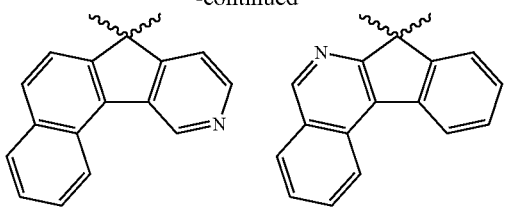
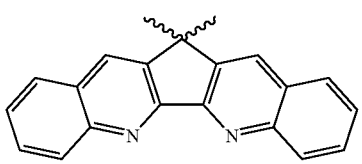
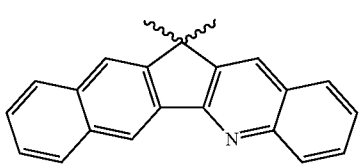
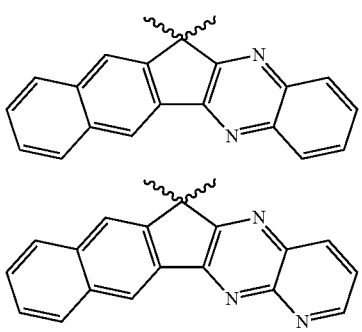
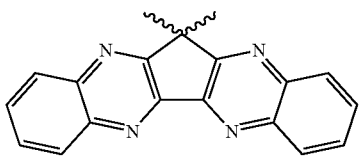
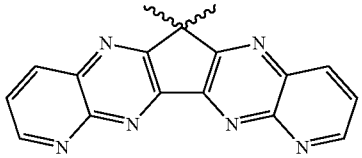
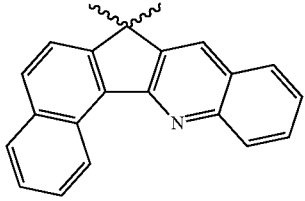
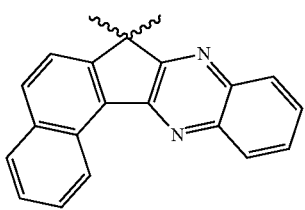
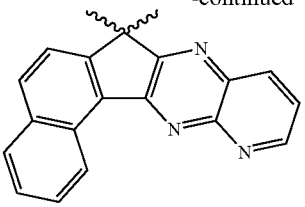
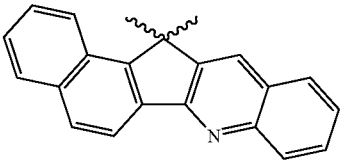
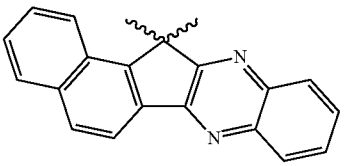
Among them (specifically, in group [I]), preferred azafluorene rings are shown below as group [J].
[Formula 22]
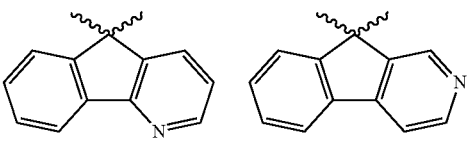
[J]
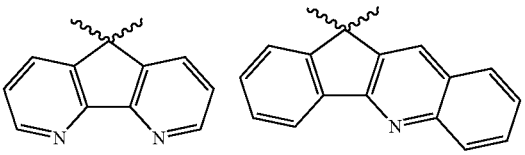
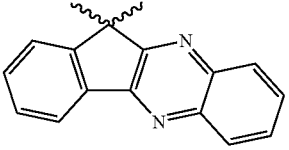
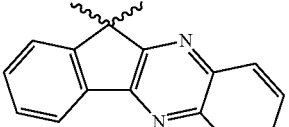
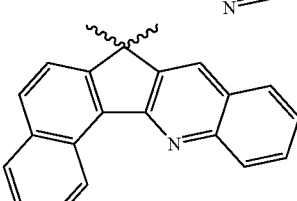
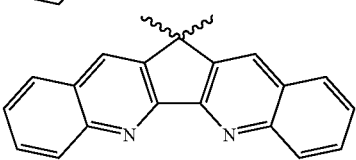

-continued

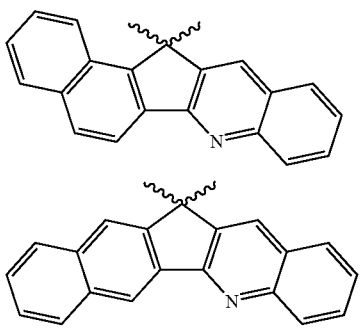

Among them (specifically in group [J]) particularly preferred azafluorene rings are shown below as group [K].

[Formula 23]

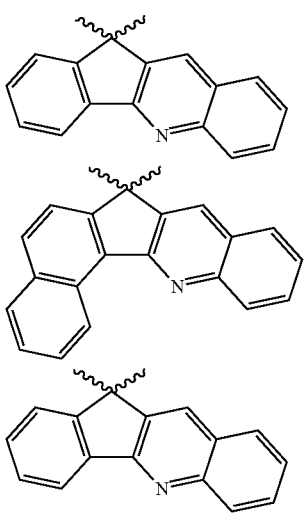

[K]

[Formula 24]

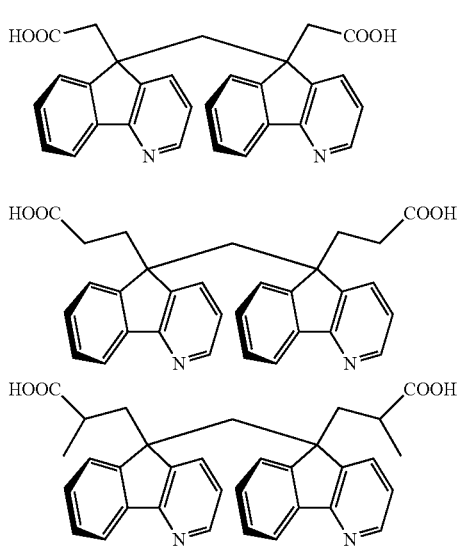

-continued

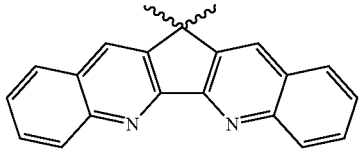

The "optionally substituted aryl group having 6 to 11 carbon atoms", the "optionally substituted heteroaryl group having 3 to 10 carbon atoms", and the "optionally substituted alkyl group having 1 to 10 carbon atoms" described as $R^{11}$ and $R^{12}$ in the formula (8) are the same as such substituents described as $R^1$ to $R^8$.

$R^{11}$ and $R^{12}$ are particularly preferably each a methyl group or an ethyl group. In this case, a polyester or a polyester carbonate can efficiently be synthesized by removing a low-boiling alcohol generated by interesterification between the diester compound represented by the formula (8) and a dihydroxy compound. On the other hand, from the viewpoint that a polyester carbonate can be synthesized in one step by adding the diester compound, the dihydroxy compound, and the diester carbonate to a reactor at a time so that interesterification reaction readily proceeds, $R^{11}$ and $R^{12}$ are preferably optionally substituted aryl groups having 6 to 11 carbon atoms. $R^{11}$ and $R^{12}$ are particularly preferably phenyl groups. In this case, the phenyl group can be distilled away as phenol after the synthesis of a polyester carbonate. When $R^{11}$ and $R^{12}$ are optionally substituted aryl groups having 6 to 11 carbon atoms, from the viewpoint of reactivity during polymerization, a diaryl carbonate that will be described later is preferably used as a diester carbonate, and from the viewpoint that a by-product can easily be removed, the aryl groups as $R^{11}$ and $R^{12}$ and aryl groups in the diaryl carbonate are more preferably the same.

In the azafluorene monomer represented by the formula (7) or (8), n is an integer of 0 to 5. From the viewpoint that when the value of n increases, purification becomes difficult due to a reduction in solubility, the value of n is preferably 2 or less, more preferably 0 or 1, particularly preferably 1.

<Specific Structure>

Examples of the azafluorene monomer represented by the formula (7) or (8) are shown below as group [L].

[L]

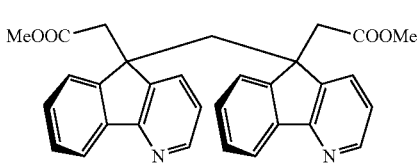

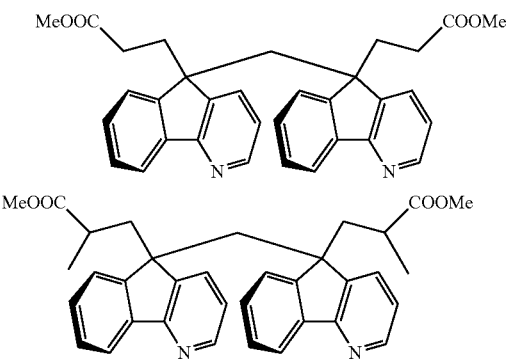

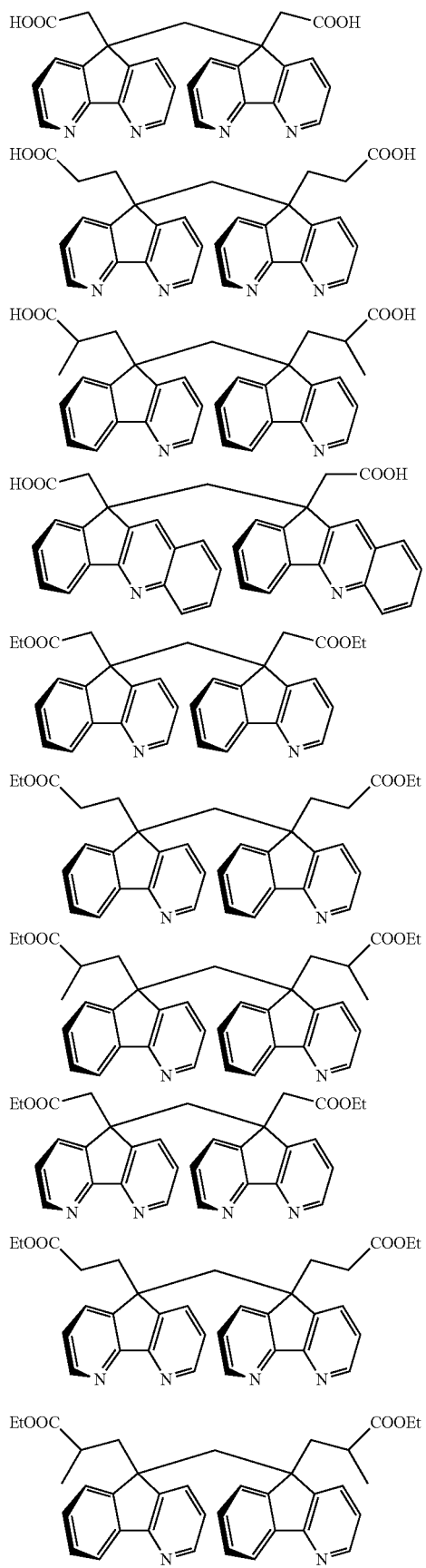
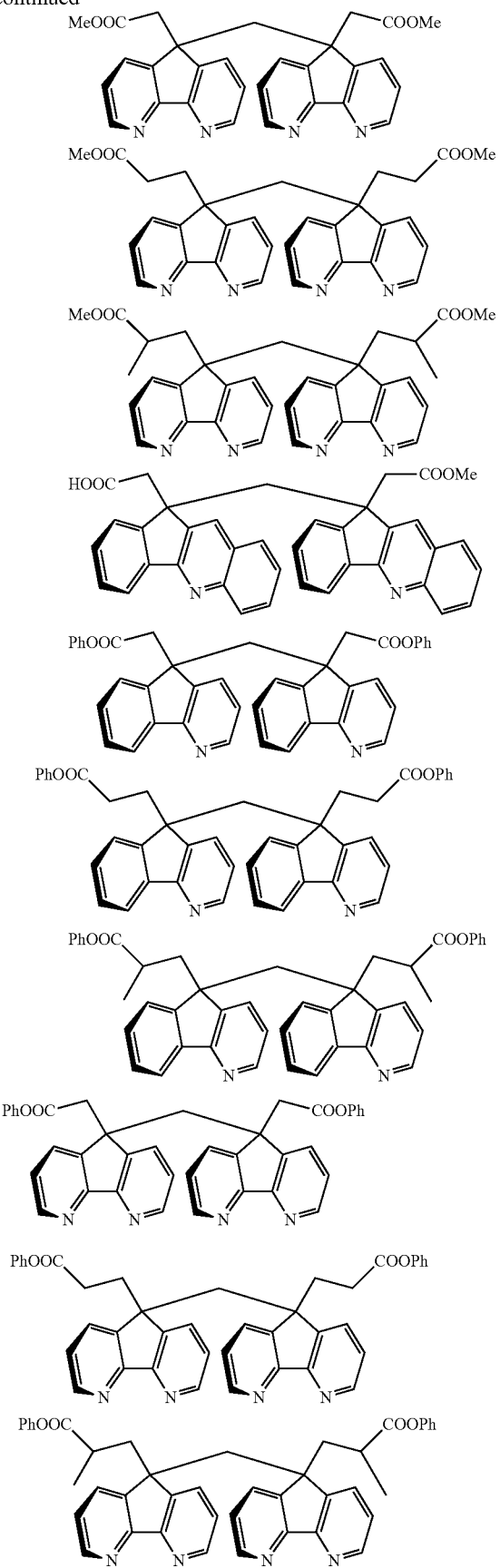

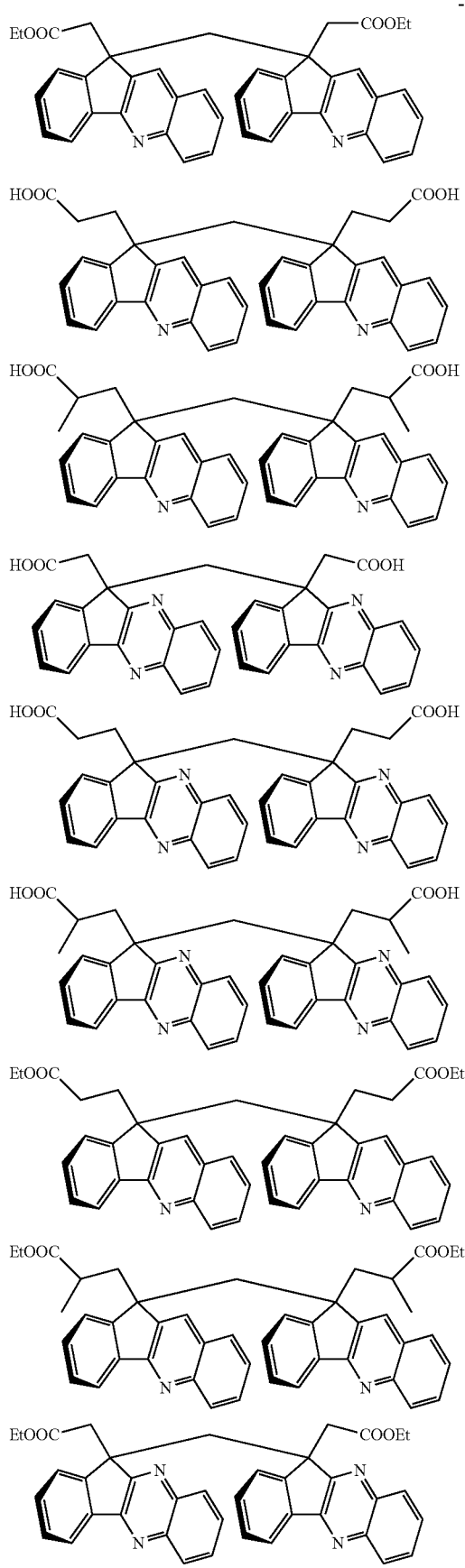
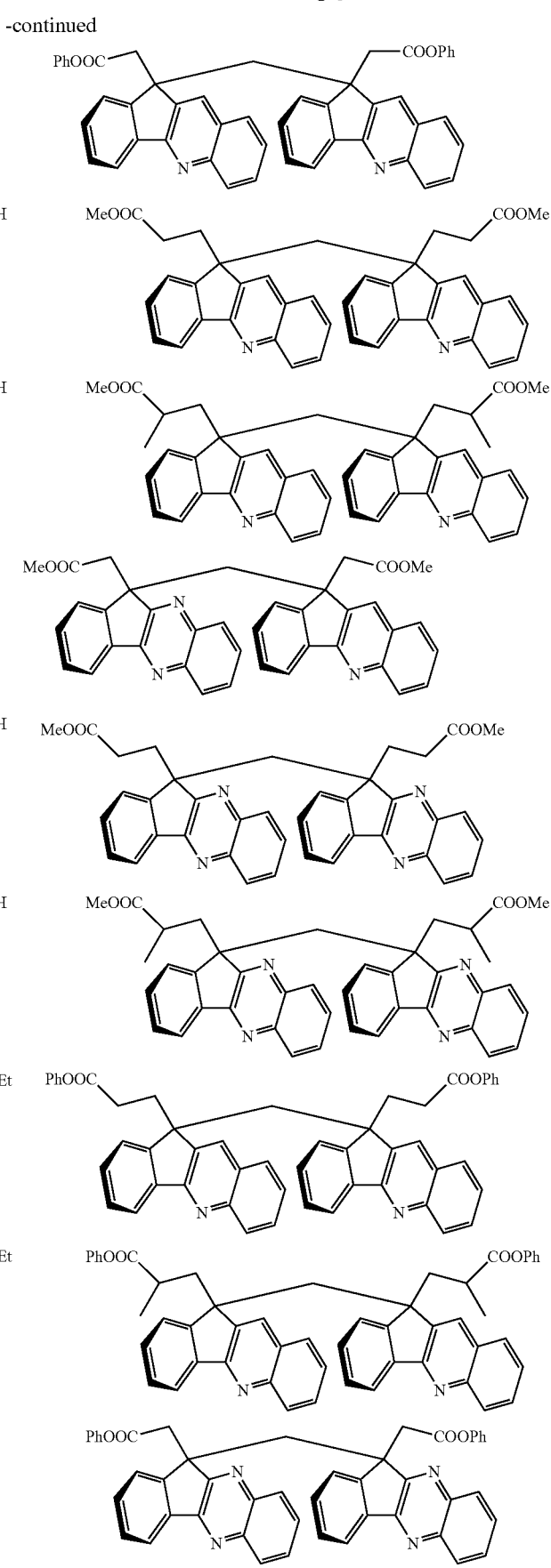

35
-continued
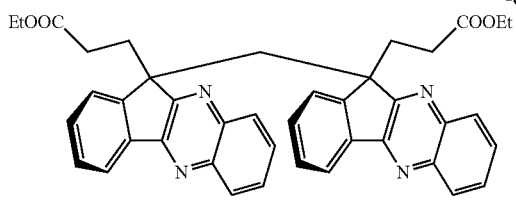
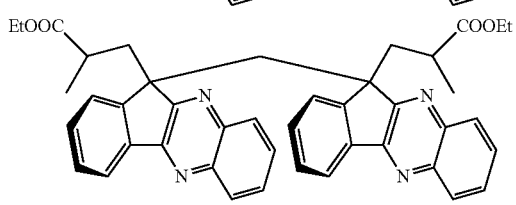
[Formula 25]
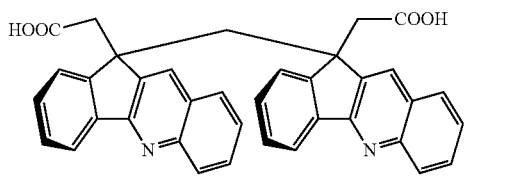
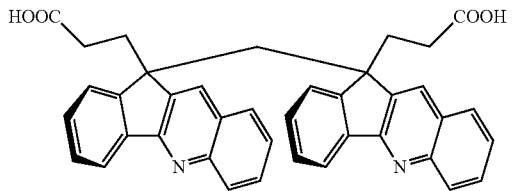
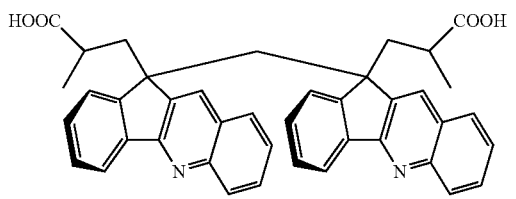
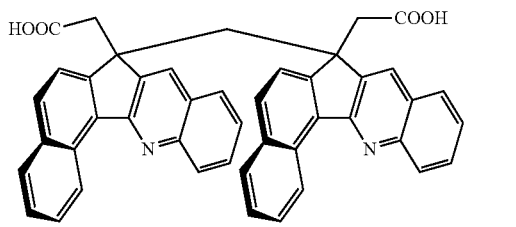
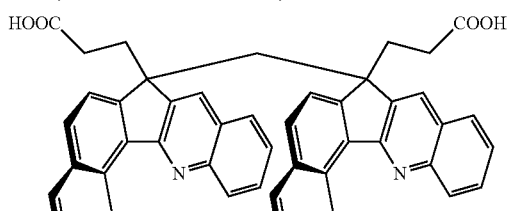
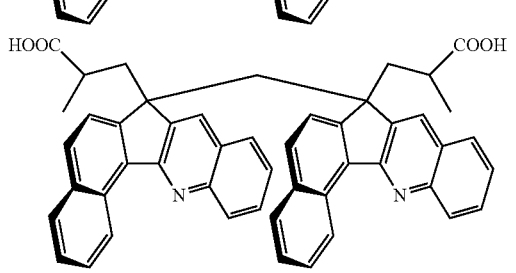
36
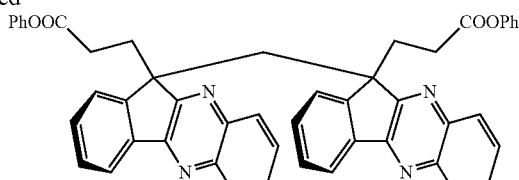
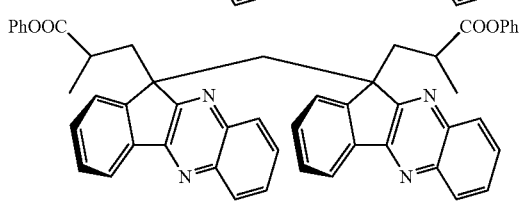
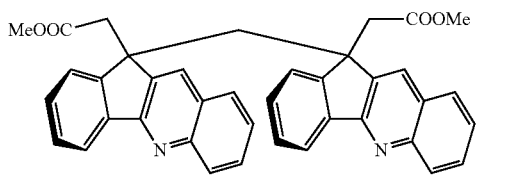
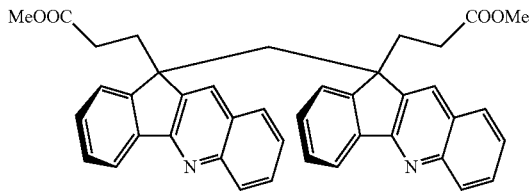
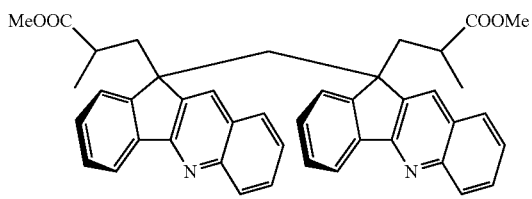
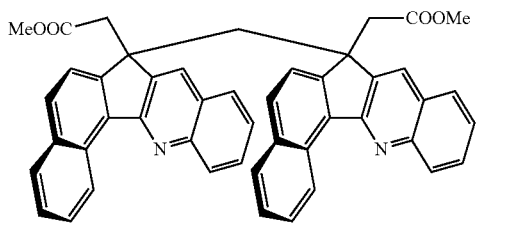
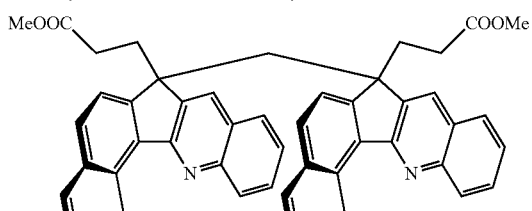
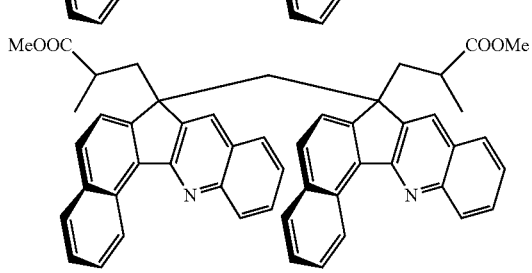

-continued
| 37 | 38 |
|---|---|
| 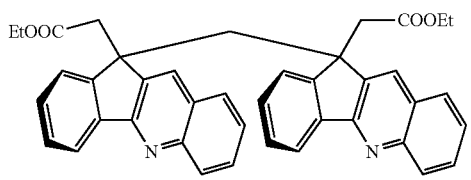 | 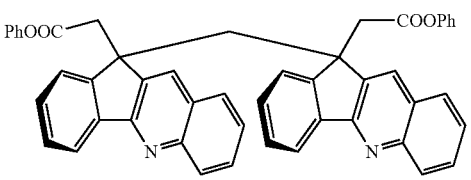 |
| 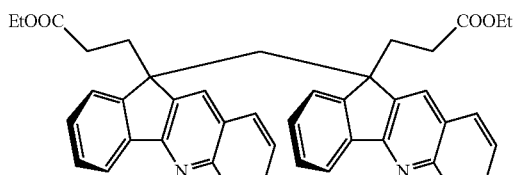 | 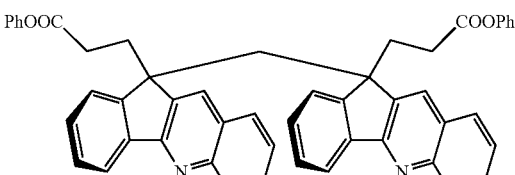 |
| 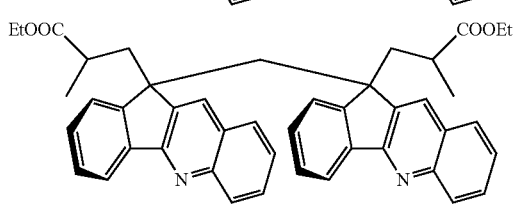 | 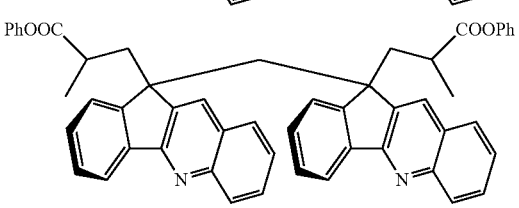 |
| 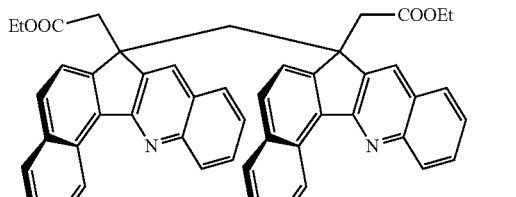 | 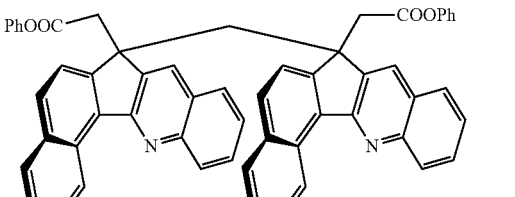 |
| 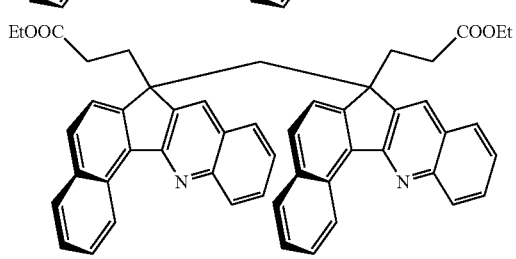 | 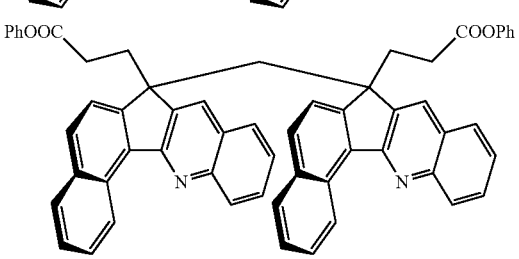 |
| 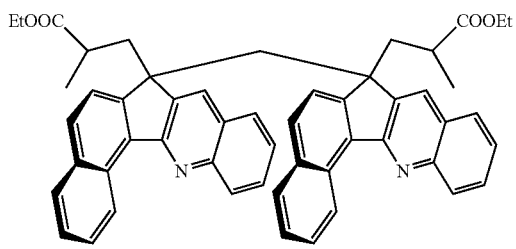 | 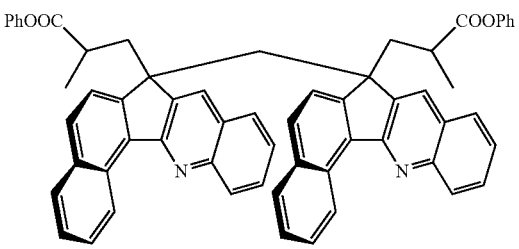 |
| 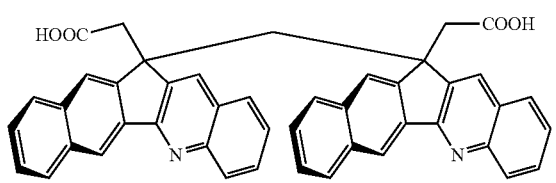 | 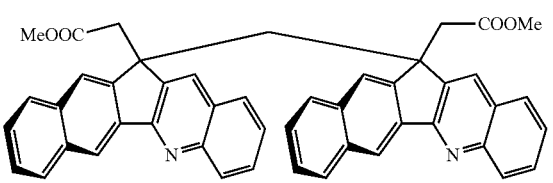 |
| 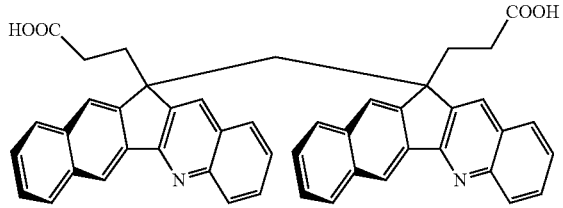 | 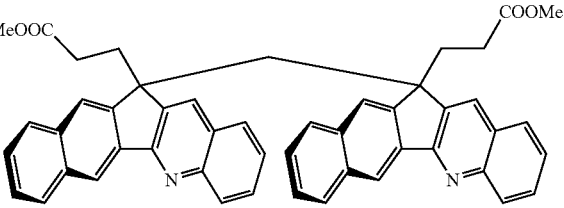 |

-continued
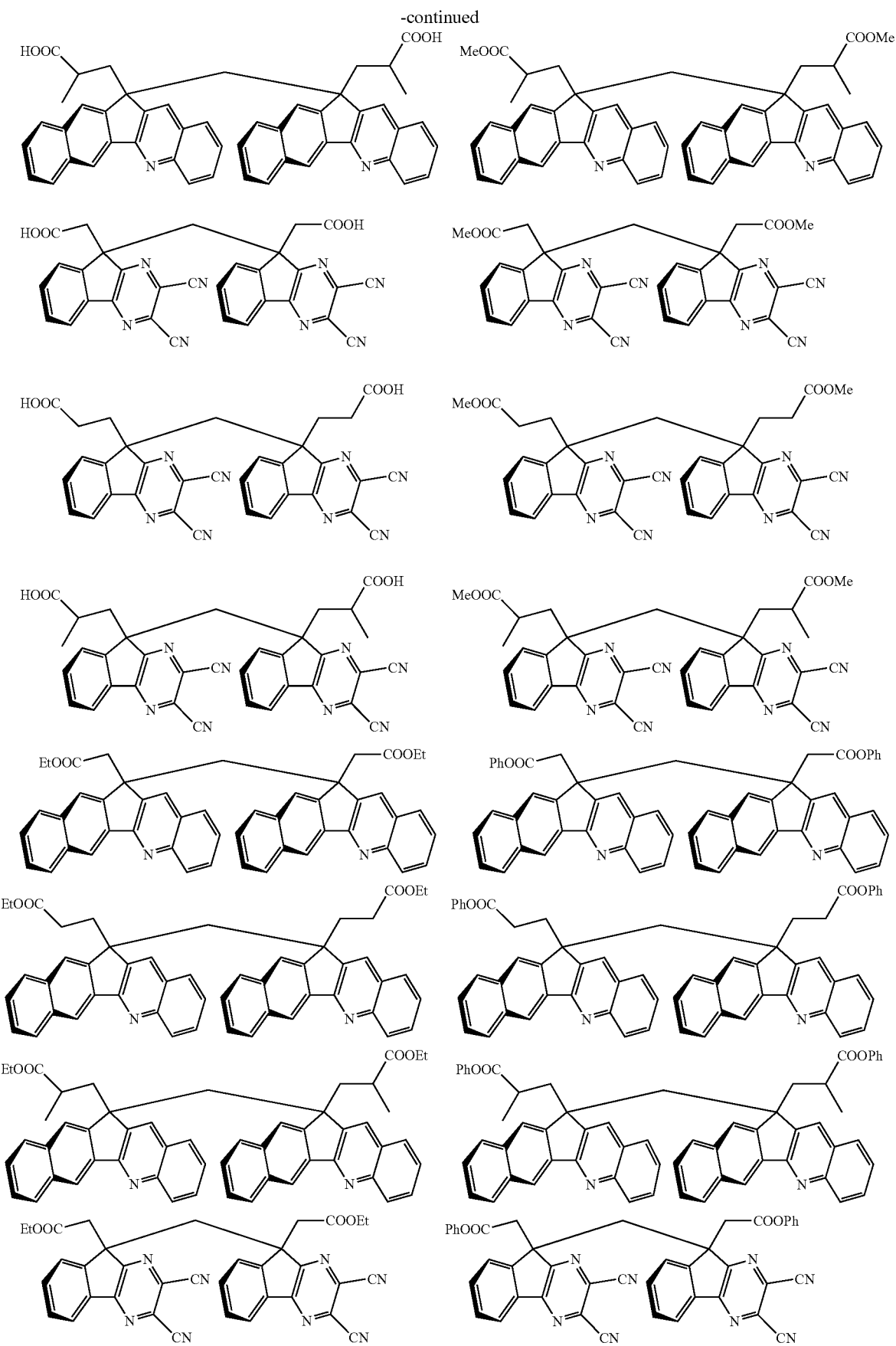

41 42
-continued
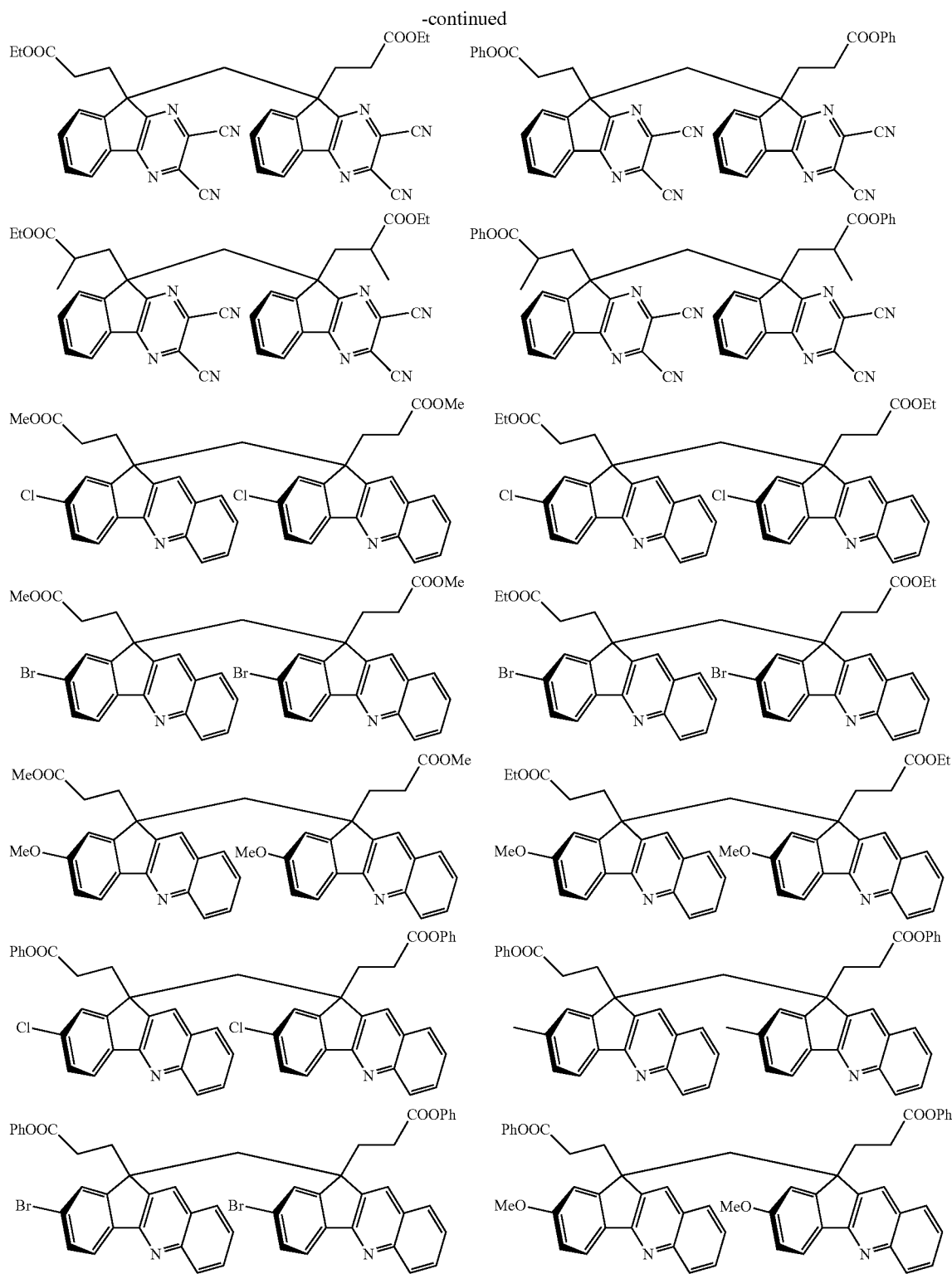
[Formula 26]
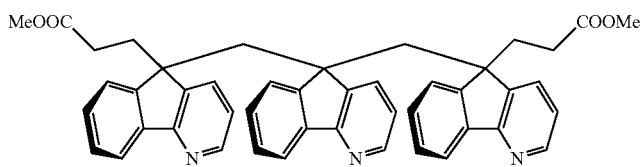

-continued
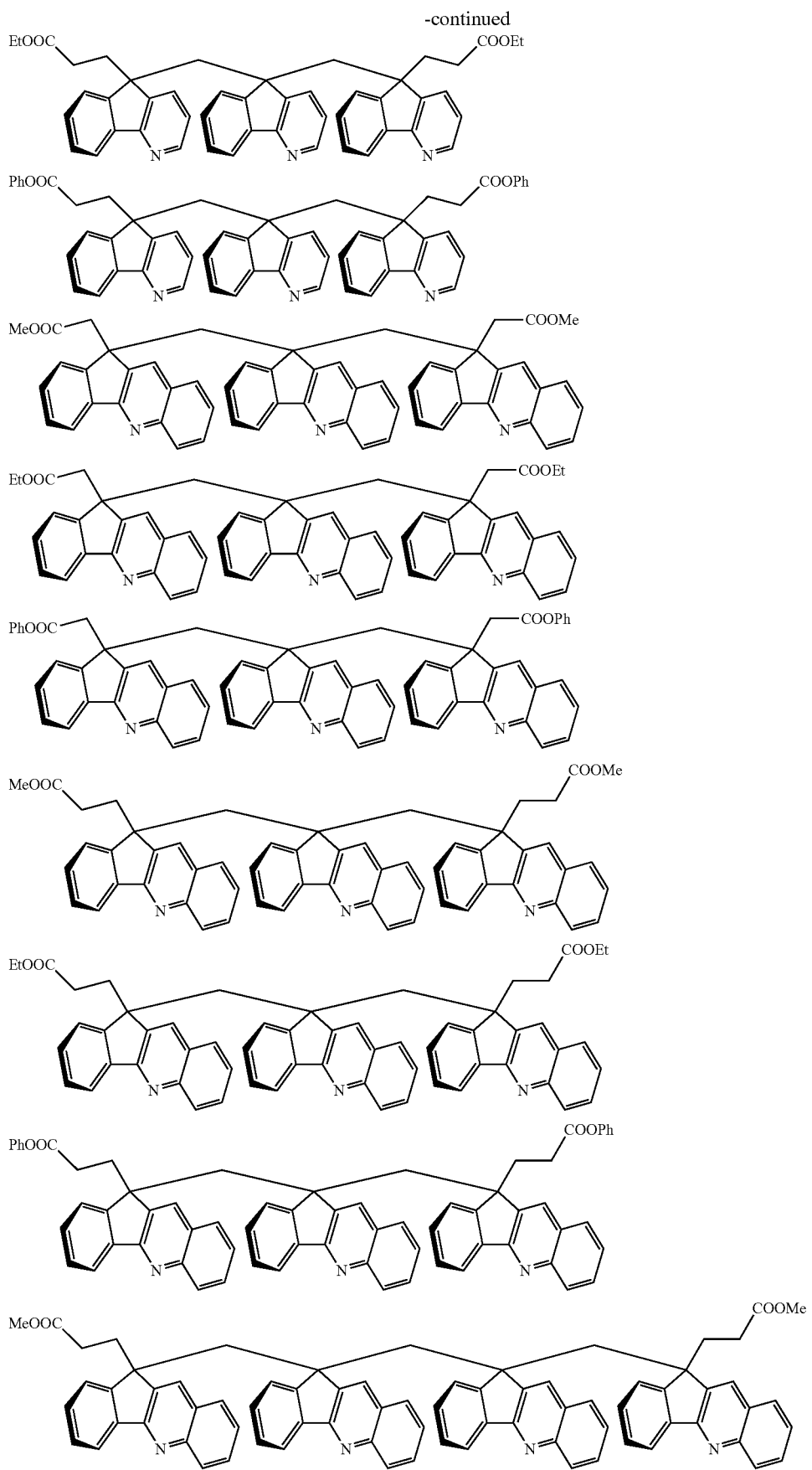

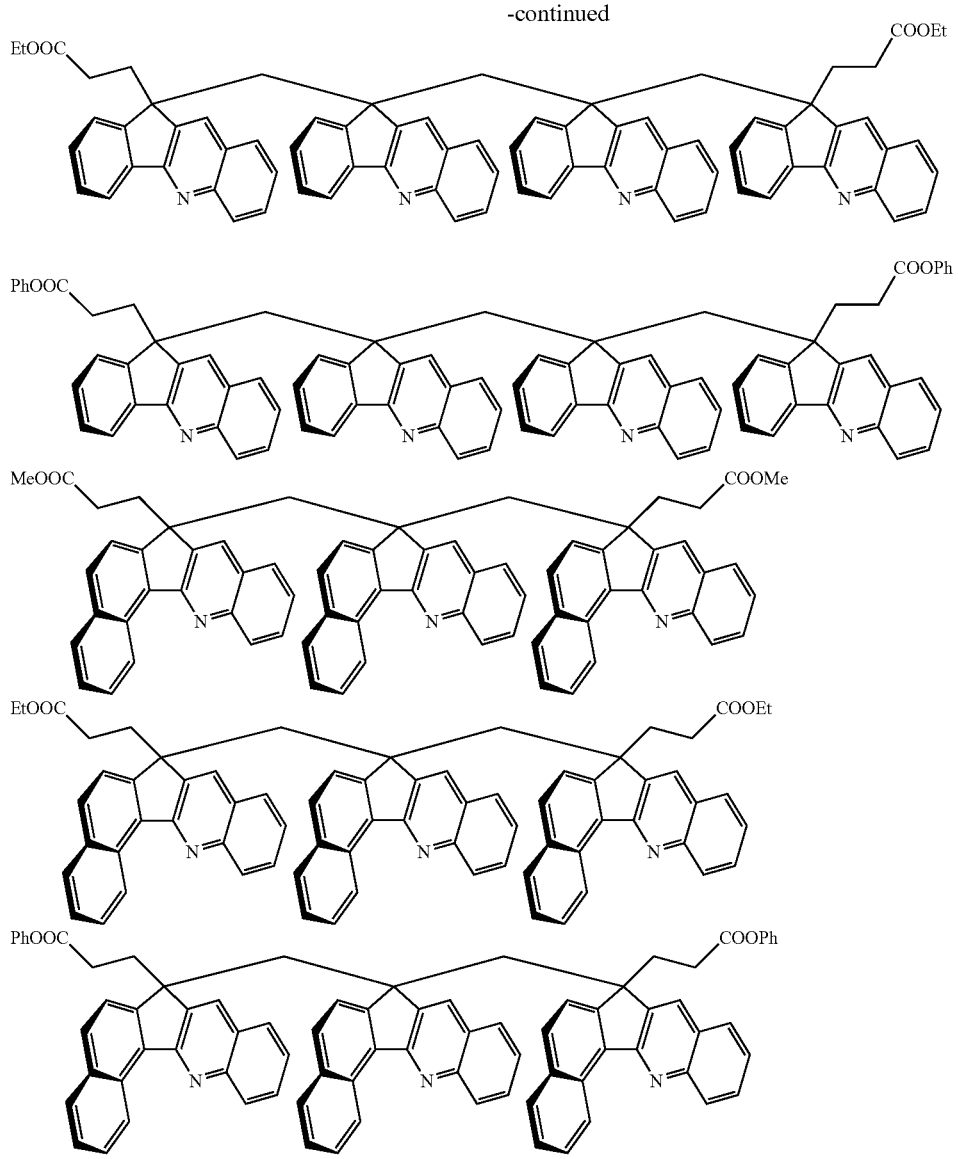
Among them, preferred azafluorene monomers are shown below as group [M].
[Formula 27]
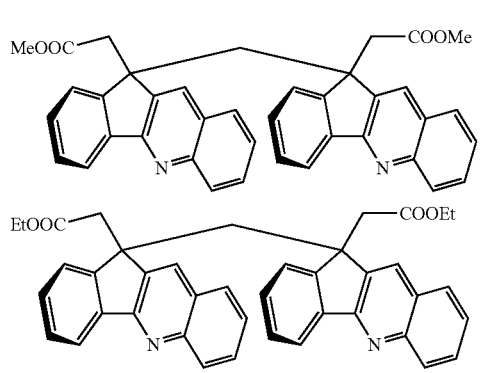
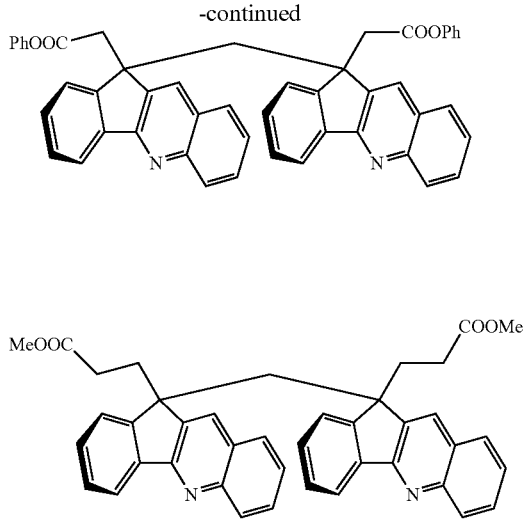

-continued

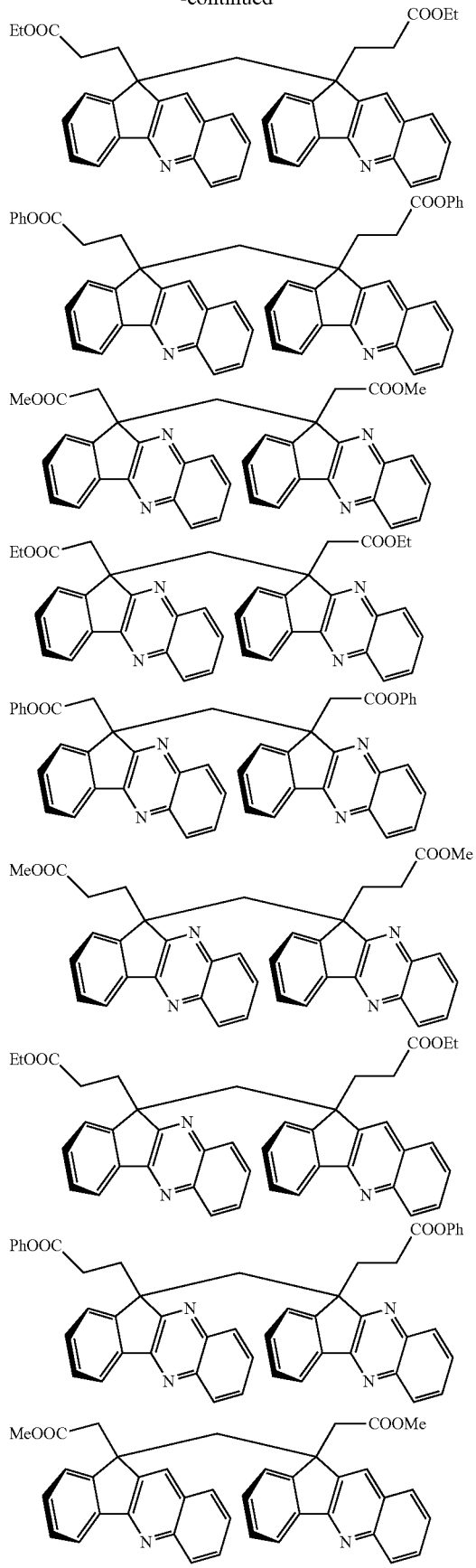

-continued

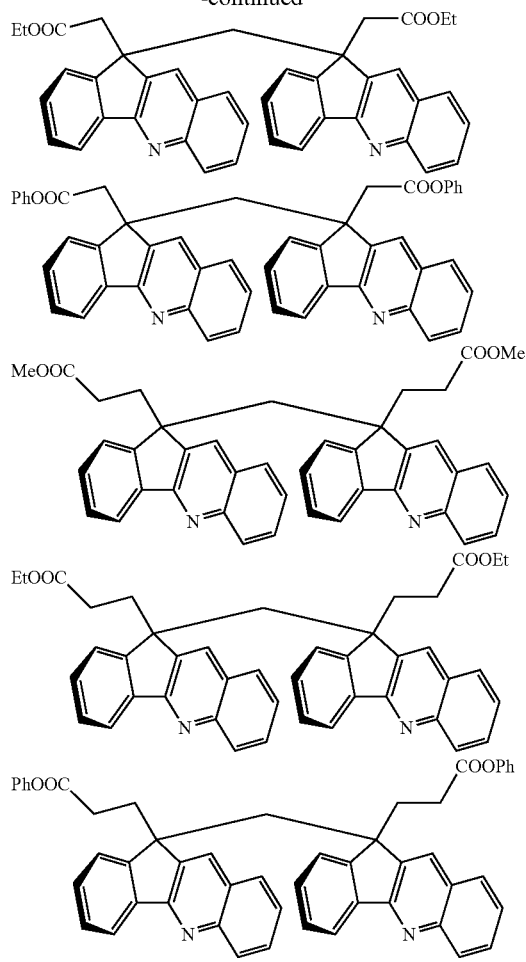

The azafluorene monomer according to the present disclosure has isomers depending on the orientation of the azafluorene ring when the two aromatic rings thereof sharing a bond with the five-membered ring are asymmetrical with respect to the five-membered ring (i.e., across the five-membered ring). These isomers may be used singly or in combination of two or more of them.

<Physical Properties of Azafluorene Monomer>

The physical property values of the azafluorene monomer according to the present disclosure are not particularly limited, but the azafluorene monomer preferably satisfies physical property values described below as examples.

When the resin according to the present disclosure is used for optical materials such as optical lenses, the refractive index of the azafluorene monomer at a wavelength of 587 nm is preferably 1.61 or more. In this case, an optical lens obtained by using a composition containing a polyester carbonate resin or a polyester resin can be made thin. A higher refractive index of the azafluorene monomer is advantageous for reducing the thickness of the lens. Therefore, the refractive index of the azafluorene monomer at a wavelength of 587 nm is more preferably 1.62 or more, even more preferably 1.63 or more, particularly preferably 1.64 or more. The refractive index of the azafluorene monomer at a wavelength of 587 nm is usually 1.75 or less.

The Abbe's number of the azafluorene monomer is preferably 25 or less. This is advantageous when a composition containing a polyester carbonate resin or a polyester resin is used for optical materials such as image-capturing optical lenses. A lower Abbe's number of the monomer is advantageous for designing image-capturing optical lenses. Therefore, the Abbe's number of the azafluorene monomer is more preferably 22 or less, even more preferably 20 or less, particularly preferably 18 or less. The Abbe's number of the azafluorene monomer is usually 13 or more.

When a composition containing a polyester carbonate resin or a polyester resin is used for an optical material, the azafluorene monomer preferably has a refractive index at a wavelength of 587 nm of 1.61 or more and an Abbe's number of 25 or less. In this case, the influence of chromatic aberration can be avoided when the optical material is reduced in size and thickness. From the viewpoint of improving such an effect, the azafluorene monomer more preferably has a refractive index at a wavelength of 587 nm of 1.62 or more and an Abbe's number of 22 or less, even more preferably has a refractive index at a wavelength of 587 nm of 1.63 or more and an Abbe's number of 20 or less, and particularly preferably has a refractive index at a wavelength of 587 nm of 1.64 or more and an Abbe's number of 18 or less.

<Method for Producing Azafluorene Monomer>

A method for producing the azafluorene monomer according to the present disclosure is not particularly limited, and the azafluorene monomer is produced by, for example, a production method A or production method B represented by the following formula.

[Formula 28]

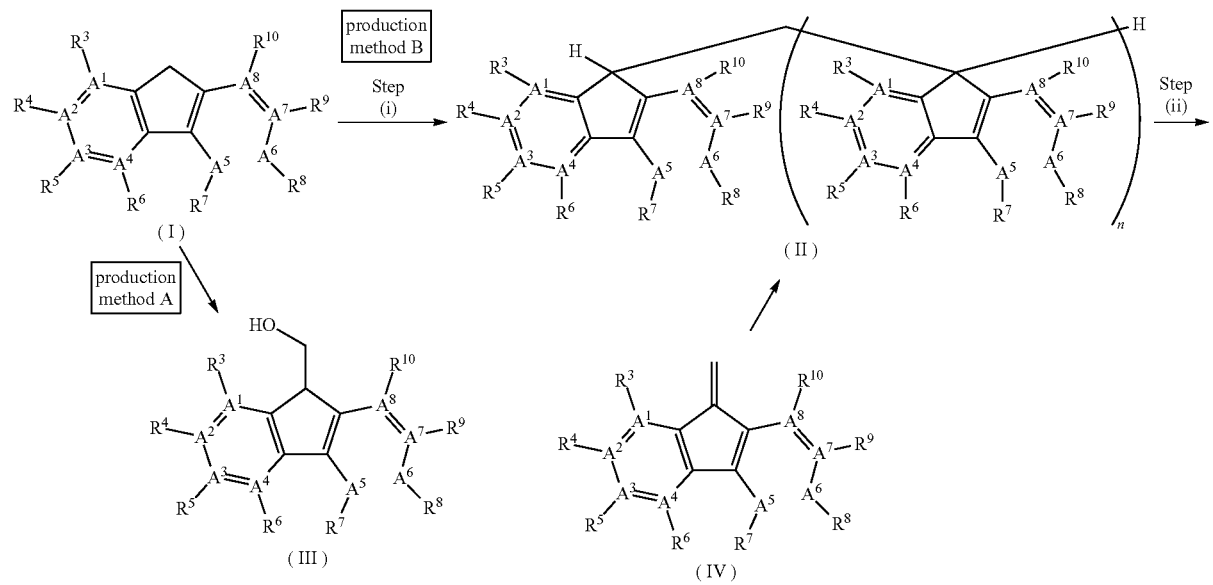

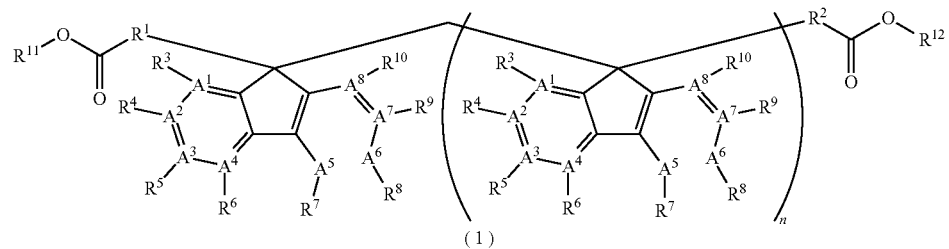

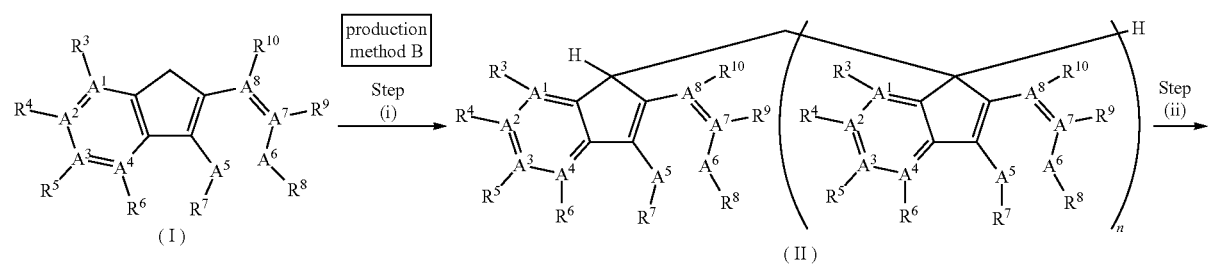

-continued

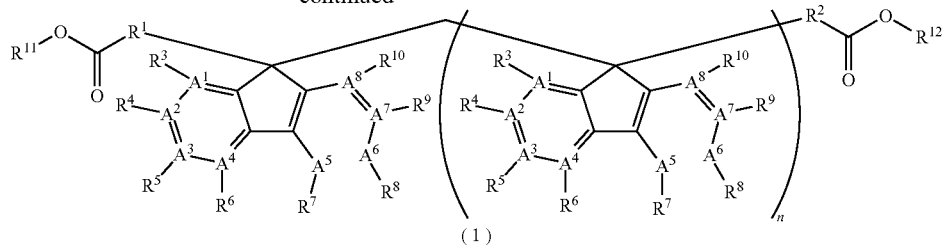

(1)

In each structural formula, $A^1$ to $A^8$ are each independently =CH— or =N—, and at least one of $A^1$ to $A^8$ is =N—. $R^1$ to $R^8$ are each independently a hydrogen atom, an optionally substituted alkyl group having 1 to 10 carbon atoms, an optionally substituted aryl group having 6 to 11 carbon atoms, an optionally substituted heteroaryl group having 3 to 10 carbon atoms, an optionally substituted acyl group having 1 to 10 carbon atoms, an optionally substituted alkoxy group having 1 to 10 carbon atoms, an optionally substituted aryloxy group having 6 to 11 carbon atoms, an optionally substituted amino group, an optionally substituted vinyl group having 2 to 10 carbon atoms, an optionally substituted ethynyl group having 2 to 10 carbon atoms, a silicon atom having a substituent, a sulfur atom having a substituent, a halogen atom, a nitro group, or a cyano group. At least two adjacent groups out of $R^1$ to $R^8$ may be bonded to each other to form a ring. $R^9$ and $R^{10}$ are each independently a direct bond or an optionally substituted alkylene group having 1 to 20 carbon atoms. $R^{11}$ and $R^{12}$ are each a hydrogen atom, an optionally substituted aryl group having 6 to 11 carbon atoms, an optionally substituted heteroaryl group having 3 to 10 carbon atoms, or an optionally substituted alkyl group having 1 to 10 carbon atoms. $R^{11}$ and $R^{12}$ may be the same or different from each other. n is an integer of 0 to 5.

<Production Method A>

In the production method A, an azafluorene (I) as a raw material is converted to a 9-hydroxymethyl azafluorene (III). Then, an olefin (IV) is synthesized by dehydration and reacted with an azafluorenyl anion. In this way, an azaoligofluorene compound (II) is produced. From the azafluorene compound (II) obtained here, an azafluorene monomer (1) can be obtained according to a step (ii).

For example, a method is known in which 9-hydroxymethylfluorene is converted to dibenzofulvene, and then an oligofluorene mixture is synthesized by anion polymerization (see Tamaki Nakano, Kazuyuki Takewaki, Tohru Yade, and Yoshio Okamoto "Dibenzofulvene, a 1,1-Diphenylethylene Analogue, Gives a π-Stacked Polymer by Anionic, Free-Radical, and Cationic Catalysts" Journal of the American Chemical Society, 1155 Sixteenth, Street N.W. Washington, DC 20036, ACS Publications, 25 Aug. 2001, 123, p. 9182-9183). Referring to this, an azafluorene compound (II) can be produced by replacing fluorene with an azafluorene (I).

It is to be noted that a method for producing the azafluorene (I) as a raw material is not particularly limited, but for example, the following method is known. 11H-indeno[1,2-b]quinoline is synthesized by, for example, converting 2-nitrobenzaldehyde to 2-aminobenzaldehyde by reduction and then reacting 2-aminobenzaldehyde with 1-indanone under basic conditions (see Nada Marquise, Guillaume Bretel, Frederic Lassagne, Floris Chevallier, Thierry Roisnel, Vincent Dorcet, Yury S. Halauko, Oleg A. Ivashkevich, Vadim E. Matulis, Philippe C. Gros and Florence Mongin. "Deproto-metallation using mixed lithium-zinc and lithium-copper bases and computed CH acidity of 2-substituted quinolines." Advances, Royal Society of Chemistry, Thomas Graham House (290), Science Park, Milton Road, Cambridge, CB4 0WF., 16 Apr. 2014. 4,19602-19612). In the same manner, 7H-benz[6,7]indeno[1,2-b]quinoline can be synthesized by, for example, reacting 2-aminobenzaldehyde and 2,3-dihydro-1H-benz[e]inden-1-one under basic conditions. 11H-indeno[1,2-b]quinoxaline is synthesized by reacting benzene-1,2-diamine and indan-1,2-dione (see Frederic Lassagne, Floris Chevallier, Thierry Roisnel, Vincent Dorcet, Florence Mongin, Luis R. Domingo. "A Combined Experimental and Theoretical Study of the Ammonium Bifluoride Catalyzed egioselective Synthesis of Quinoxalines and Pyrido[2,3-b]pyrazines." Synthesis, Georg Thieme Verlag KG., 19 May 2015. 47, p. 2680-2689). 3,3'-methylene-2,2-biquinoline is synthesized by, for example, reacting 2-aminobenzaldehyde and 1,2-cyclopentanedione under basic conditions (see Jacques Royer, Henri Philippe Husson. "Asymmetric synthesis. 2. Practical method for the asymmetric synthesis of indolizidine alkaloids: total synthesis of (−)-monomorine I." The Journal of Organic Chemistry, 1155 Sixteenth Street N.W. Washington, DC 20036, ACS Publications, 1 Mar. 1985, 50, 5, p. 670-673).

<Production Method B>

In the production method B, an azafluorene (I) as a raw material is subjected to a crosslinking reaction (step (i)) to synthesize an azafluorene compound (II). Then, an ester group is introduced into the azafluorene compound (II) (step (ii)) to produce an azafluorene monomer (1).

[Formula 29]

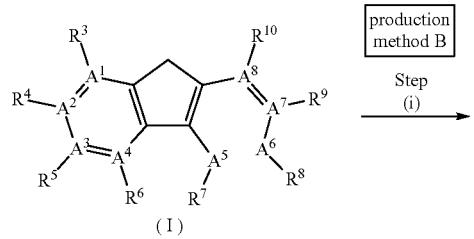

(I)

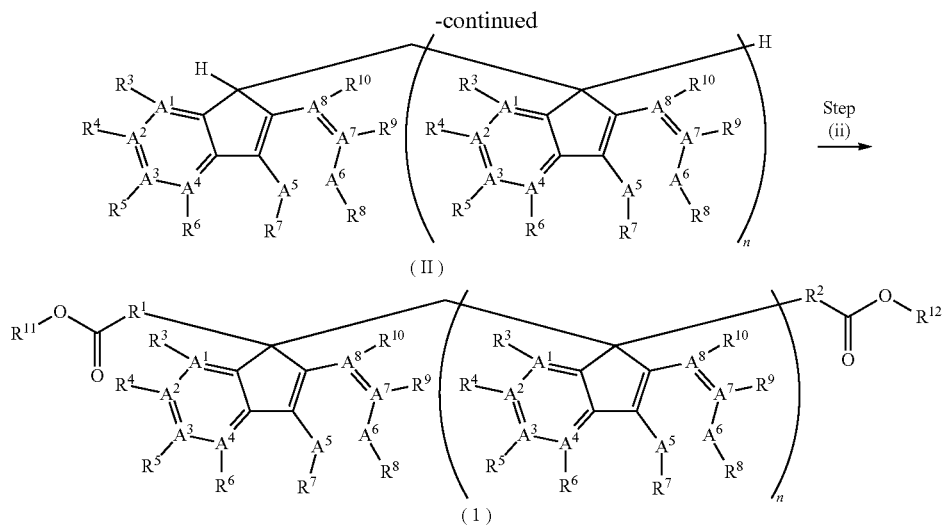

(II)

(1)

In the formula, $A^1$ to $A^8$, $R^1$ to $R^{12}$, and n are the same as those in the formulas (7) and (8).

Hereinbelow, the production method B will be described which is divided into a method for producing an azafluorene compound (II) in a step (i) and a method for producing an azafluorene monomer (1) in a step (ii).

<Step (i): Method for Producing Azafluorene Compound (II)>

An azafluorene compound having a methylene crosslink represented by the following general formula (II) is produced from, for example, an azafluorene (I) and a formaldehyde in the presence of a base through a reaction represented by the following formula.

[Formula 30]

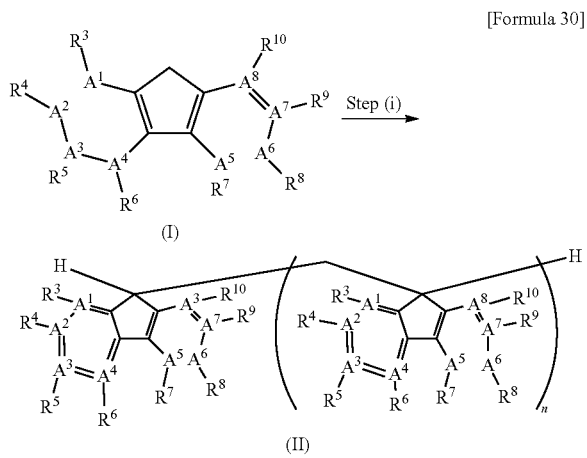

In the formula, $A^1$ to $A^8$, $R^1$ to $R^8$, and n are the same as those in the formula (1).

<Formaldehyde>

The formaldehyde used in the step (i) is not particularly limited as long as formaldehyde can be supplied to a reaction system. Specific examples of the formaldehyde include gaseous formaldehyde, an aqueous formaldehyde solution, paraformaldehyde obtained by polymerizing formaldehyde, and trioxane. Among them, an aqueous formaldehyde solution or paraformaldehyde is preferably used. In this case, inexpensive industrial production can be achieved, and the formaldehyde can easily be handled and therefore can accurately be weighed.

(Definition of Theoretical Amount)

In order to produce an azafluorene compound (II) in which n is a desired value, the theoretical amount (mole ratio) of a formaldehyde relative to an azafluorene (I) as a raw material is represented by n/(n+1).

(Reason why it is Better not to Exceed Theoretical Amount)

When the formaldehyde is used in an amount exceeding a theoretical amount relative to the azafluorene (I), an azafluorene compound (IIa) in which n exceeds a desired value tends to be generated. Since solubility reduces as n increases, a heavier load tends to be applied to purification when the amount of the azafluorene compound (IIa), in which n exceeds a desired value, present in a desired product (specifically, an azafluorene compound (II) in which n is a desired value) is larger. Therefore, it is preferred that the amount of the formaldehyde used is usually n/(n+1) times by mol, which is a theoretical amount, or less.

(Reason why it is Better not to be Much Smaller than Theoretical Amount)

On the other hand, if the amount of the formaldehyde used is much smaller than n/(n+1) that is a theoretical amount, an azafluorene compound (IIb) in which n is not a desired value is mainly produced or the unreacted azafluorene (I) as a raw material remains. It has been found that this tends to significantly reduce the yield.

More specifically, when n=1, the amount of the formaldehyde used is usually 0.1 times by mol or more, preferably 0.3 times by mol or more, more preferably 0.38 times by mol or more relative to the azafluorene (I). Further, when n=1, the amount of the formaldehyde used is usually 0.5 times by mol or less, preferably 0.46 times by mol or less, more preferably 0.42 times by mol or less relative to the azafluorene (I).

When n=2, the amount of the formaldehyde used is usually 0.5 times by mol or more, preferably 0.55 times by mol or more, more preferably 0.6 times by mol or more relative to the azafluorene (I). Further, when n=2, the amount of the formaldehyde used is usually 0.66 times by mol or less, preferably 0.65 times by mol or less, more preferably 0.63 times by mol or less relative to the azafluorene (I). As described above, it has been found that the structure of a main product and the ratio of a product significantly change depending on the amount of the formaldehyde used. Therefore, an azafluorene compound (II) in which n is a desired value can be obtained in high yield by limiting the amount of the formaldehyde used.

<Base>

Examples of the base used in the step (i) include: hydroxides of alkali metals such as lithium hydroxide, sodium hydroxide, and potassium hydroxide; hydroxides of alkaline earth metals such as calcium hydroxide and barium hydroxide; carbonates of alkali metals such as sodium carbonate, sodium hydrogen carbonate, and potassium carbonate; carbonates of alkaline earth metals such as magnesium carbonate and calcium carbonate; alkali metal salts of phosphoric acid such as sodium phosphate, sodium hydrogen phosphate, and potassium phosphate; organic lithium salts such as n-butyllithium and tertiary butyllithium; alkoxide salts of alkali metals such as sodium methoxide, sodium ethoxide, and potassium tertiary butoxide; alkali metal hydrides such as sodium hydride and potassium hydride; tertiary amines such as triethylamine and diazabicycloundecene; and quaternary ammonium hydroxides such as tetramethylammonium hydroxide and tetrabutylammonium hydroxide. These bases may be used singly or in combination of two or more of them.

Among them, alkoxides of alkali metals having sufficient basicity in the reaction in the step (i) are preferred, and industrially inexpensive sodium methoxide and sodium ethoxide are more preferred. The alkali metal alkoxide to be used here may be in the form of powder or may be a liquid such as an alcohol solution. The alkali metal alkoxide may be prepared by reacting an alkali metal and an alcohol.

The upper limit of the amount of the base used relative to the azafluorene (I) as a raw material is not particularly limited, but if the amount of the base used is too large, a heavy load is applied to stirring or purification after the reaction. From such a viewpoint, the amount of the base used is usually 10 times by mol or less, preferably 5 times by mol or less, more preferably 1 times by mol or less the azafluorene (I). On the other hand, if the amount of the base used is too small, the reaction slows down. Therefore, the amount of the base used is usually 0.01 times by mol or more, preferably 0.1 times by mol or more, more preferably 0.2 times by mol or more relative to the azafluorene (I) as a raw material.

<Solvent>

The step (i) is preferably performed using a solvent. Specific examples of a usable solvent include: alkyl nitrile-based solvents such as acetonitrile and propionitrile; ether-based solvents such as diethyl ether, tetrahydrofuran, 1,4-dioxane, methyl cyclopentyl ether, and tertiary butyl methyl ether; halogen-based solvents such as 1,2-dichloroethane, dichloromethane, chloroform, and 1,1,2,2-tetrachloroethane; halogen-based aromatic hydrocarbons such as chlorobenzene and 1,2-dichlorobenzene; amide-based solvents such as N,N-dimethylformamide, N,N-dimethylacetamide, and N-methylpyrrolidone; sulfoxide-based solvents such as dimethylsulfoxide and sulfolane; monocyclic aliphatic hydrocarbons (it is to be noted that monocyclic aliphatic hydrocarbons are a kind of cyclic aliphatic hydrocarbons) such as cyclopentane, cyclohexane, cycloheptane, and cyclooctane; monocyclic aliphatic hydrocarbon derivatives such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, and 1,3,5-trimethylcyclohexane; polycyclic aliphatic hydrocarbons (it is to be noted that polycyclic aliphatic hydrocarbons are a kind of cyclic aliphatic hydrocarbons) such as decalin; acyclic aliphatic hydrocarbons such as n-pentane, n-hexane, n-heptane, n-octane, isooctane, n-nonane, n-decane, n-dodecane, and n-tetradecane; aromatic hydrocarbons such as toluene, p-xylene, o-xylene, and m-xylene; and alcohol-based solvents such as methanol, ethanol, isopropanol, n-butanol, tertiary-butanol, hexanol, octanol, and cyclohexanol.

Among them, polar solvents are preferred because they have a high ability to dissolve an anion generated from the azafluorene (I), and therefore the reaction tends to successfully proceed. More specifically, amide-based solvents or sulfoxide-based solvents are preferred. Among them, N,N-dimethylformamide is particularly preferred when an azafluorene compound (II) in which n=1 or 2 (specifically, an oligoazafluorene compound (II)) is produced. This is because the solubility of the azafluorene compound (II), in which n=1 or 2, in N,N-dimethylformamide is low, and therefore a generated desired product is immediately precipitated, and the reaction is prevented from further proceeding so that the selectivity of the desired product tends to improve.

These solvents may be used singly or in combination of two or more of them (specifically, a mixture of two or more solvents).

It has been found that the solubility of the azafluorene compound (II) produced in the step (i) in the solvent reduces as the value of n increases, and therefore it is considered that further progress of the reaction is prevented due to immediate precipitation of the generated desired product. Therefore, the amount of the solvent used is preferably appropriately adjusted depending on the value of n. Particularly, when an azafluorene compound (II) in which n=1 or 2 is produced, it is better not to use the solvent excessively in order to increase the selectivity of the desired product. For example, when N,N-dimethylformamide that is a particularly preferred solvent is used, the upper limit of the amount of the solvent used is usually 10 times by volume, preferably 7 times by volume, more preferably 4 times by volume the azafluorene (I) as a raw material. On the other hand, if the amount of the solvent used is too small, stirring is difficult and the reaction slows down, and therefore the lower limit of the amount of the solvent used is usually 1 times by volume, preferably 2 times by volume, more preferably 3 times by volume the azafluorene (I) as a raw material.

<Reaction Mode>

When the step (i) is performed, the mode of the reaction is not particularly limited, and may be batch mode, flow-through mode, or a combination of them.

<Reaction Conditions>

The conditions of the reaction in the step (i) are appropriately adjusted so that an azafluorene compound (II) in which n is a desired value is generated. In order to prevent the reaction from proceeding so that a product having n exceeding a desired value is not generated, the reaction is preferably performed at a temperature as low as possible. On the other hand, if the temperature is too low, there is a possibility that a sufficient reaction speed cannot be achieved.

When N,N-dimethylformamide that is a particularly preferred solvent and sodium ethoxide that is a particularly preferred base are used and n=1 or 2, the upper limit of the reaction temperature is usually 30° C., preferably 20° C., more preferably 10° C. On the other hand, the lower limit of the reaction temperature is usually −50° C., preferably −20° C., more preferably 0° C.

The lower limit of a general reaction time in the step (i) is usually 30 minutes, preferably 60 minutes, more preferably 2 hours. The upper limit of the reaction time is not particularly limited, but is usually 20 hours, preferably 10 hours, more preferably 5 hours.

<Separation and Purification of Desired Product>

After the completion of the reaction, an azafluorene compound (II) as a desired product is precipitated and isolated by adding a reaction liquid to an acidic water such as dilute hydrochloric acid or by adding acidic water such as dilute hydrochloric acid to a reaction liquid.

Alternatively, after the completion of the reaction, an azafluorene compound (II) as a desired product may be extracted by adding a solvent capable of dissolving the desired product and water to a reaction liquid. The desired product extracted by the solvent is isolated by, for example, a method in which the solvent is concentrated or a method in which a poor solvent is added. However, the solubility of the azafluorene compound (II) in the solvent tends to be very low at room temperature, and therefore the azafluorene compound (II) is usually preferably precipitated by a method in which a reaction liquid is brought into contact with acidic water.

The obtained azafluorene compound (II) can directly be used as a raw material in the step (ii), but may be purified before used in the step (ii). A purification method is not particularly limited, and a usual purification method can be used. More specifically, purification is performed by recrystallization, reprecipitation, extractive purification, or column chromatography.

<Method for Producing Azafluorene Monomer (1)>

Hereinbelow, methods for producing an azafluorene monomer (1) in the step (ii) represented by the following formula will be described, which are different in the type of reaction.

[Formula 31]

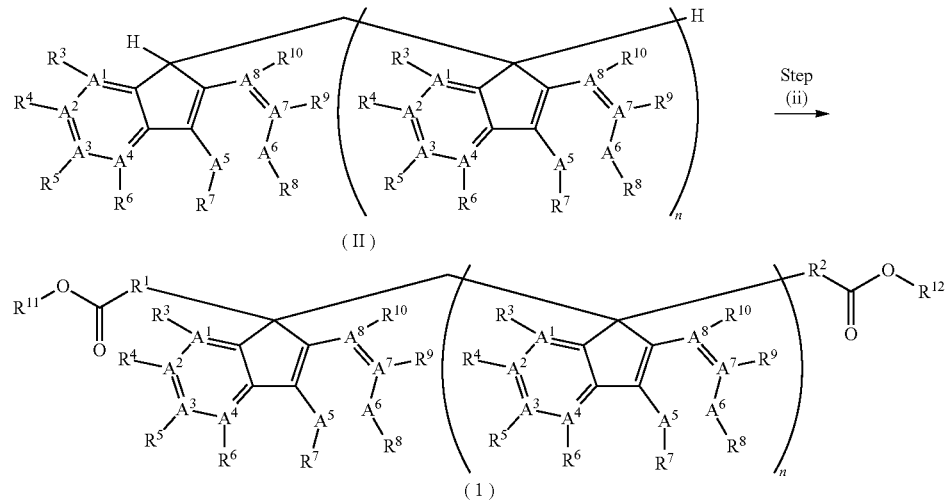

In the formula, $A^1$ to $A^8$, $R^1$ to $R^{12}$, and n are the same as those in the formulas (7) and (8).

<Step (iia): Production Method Based on Michael Addition>

An azafluorene monomer represented by the following general formula (1a) is produced from an azafluorene compound (II) and an ester group-substituted olefin (V) in the presence of a base through a reaction in the step (iia) shown below.

[Formula 32]

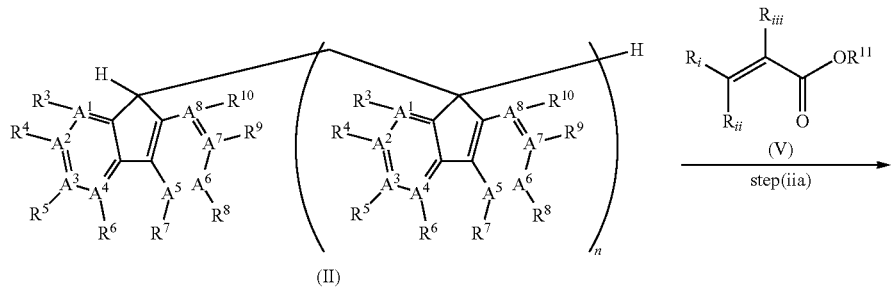

-continued

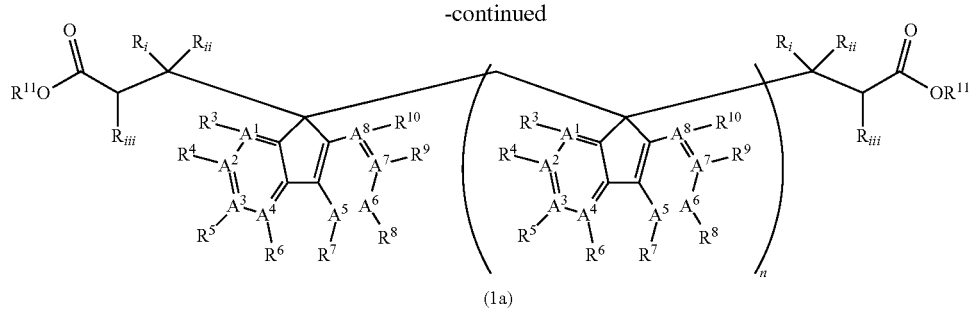

(1a)

In the formula, $A^1$ to $A^8$, $R^1$ to $R^{11}$, and n are the same as those in the formulas (7) and (8), and $R_i$, $R_{ii}$, and $R_{iii}$ are each a hydrogen atom, an optionally substituted alkyl group having 1 to 10 carbon atoms, an optionally substituted aryl group having 4 to 10 carbon atoms, or an optionally substituted aralkyl group having 6 to 10 carbon atoms.

<Electron Withdrawing Group-Substituted Olefin>

The electron withdrawing group-substituted olefin as a reaction reagent is represented by a general formula (V) in the step (iia). In the general formula (V), $R_i$, $R_{ii}$, and $R_{iii}$ are each independently a hydrogen atom, an alkyl group having 1 to 10 carbon atoms, an optionally substituted aryl group having 4 to 10 carbon atoms, or an optionally substituted aralkyl group having 6 to 10 carbon atoms. Specific examples of $R_i$, $R_{ii}$, and $R_{iii}$ include: linear or branched alkyl groups such as a methyl group, an ethyl group, an n-propyl group, an isopropyl group, and a cyclohexyl group; aryl groups such as a phenyl group, a 1-naphthyl group, a 2-naphthyl group, and a 2-thienyl group; and aralkyl groups such as a benzyl group, a 2-phenylethyl group, and a p-methoxybenzyl group.

These substituents may further be substituted with any substituent as long as the reaction in the step (iia) is not inhibited.

Examples of the electron withdrawing group-substituted olefin (V) include: acrylic acid esters such as methyl acrylate, ethyl acrylate, phenyl acrylate, allyl acrylate, glycidyl acrylate, 2-hydroxyethyl acrylate, 4-hydroxybutyl acrylate, and 1,4-cyclohexanedimethanol monoacrylate; methacrylic acid esters such as methyl methacrylate, ethyl methacrylate, phenyl methacrylate, allyl methacrylate, glycidyl methacrylate, and 2-hydroxyethyl methacrylate; α-substituted unsaturated esters such as methyl 2-ethylacrylate and methyl 2-phenylacrylate; and β-substituted unsaturated esters such as methyl cinnamate, ethyl cinnamate, methyl crotonate, and ethyl crotonate.

The electron withdrawing group-substituted olefin (V) is preferably an unsaturated carboxylic acid ester represented by the following general formula (V-1) capable of directly introducing a polymerizable reactive group. From the viewpoint of reaction speed and reaction selectivity, acrylic acid esters, methacrylic acid esters, or α-substituted unsaturated esters included in unsaturated carboxylic acid esters represented by the formula (V-1) are more preferred, and acrylic acid esters in which $R_{iii}$ is a hydrogen atom or a methyl group or methacrylic acid esters in which $R_{iii}$ is a hydrogen atom or a methyl group are even more preferred. When $R^{11}$ is smaller, more inexpensive industrial production can be achieved, distillation purification is easier, and reactivity is higher. Therefore, methyl acrylate, methyl methacrylate, ethyl acrylate, ethyl methacrylate, phenyl acrylate, or phenyl methacrylate is particularly preferred.

[Formula 33]

(V-1)

In the formula, $R^{11}$ is the same as that in the formula (8). $R_{iii}$ is a hydrogen atom, an optionally substituted alkyl group having 1 to 10 carbon atoms, an optionally substituted aryl group having 4 to 10 carbon atoms, or an optionally substituted aralkyl group having 6 to 10 carbon atoms.

The organic substituent of the ester group is preferably a hydroxyalkyl group. More specifically, the unsaturated carboxylic acid ester represented by the formula (V-1) is preferably an ester having a hydroxyalkyl group, such as 2-hydroxyethyl acrylate, 4-hydroxybutyl acrylate, or a 1,4-cyclohexanedimethanol monoacrylate. In this case, the raw material of a polyester carbonate or polyester can be obtained in one step.

Two or more different kinds of electron withdrawing group-substituted olefins (V) may be used, but one kind of electron withdrawing group-substituted olefin (V) is preferably used from the viewpoint of ease of purification.

The electron withdrawing group-substituted olefin (V) has high polymerization activity. Therefore, when the electron withdrawing group-substituted olefin (V) is present in high concentration, polymerization tends to readily proceed due to external stimuli such as light, heat, acid, and base. At this time, a large amount of heat is generated. Therefore, it is better not to use the electron withdrawing group-substituted olefin (V) excessively from the viewpoint of safety. The amount of the electron withdrawing group-substituted olefin (V) used is usually 10 times by mol or less, preferably 5 times by mol or less, more preferably 3 times by mol or less relative to the azafluorene compound (II) as a raw material. The lower limit of a theoretical amount is 2 times by mol relative to the raw material, and therefore the amount of the electron withdrawing group-substituted olefin (V) used is usually 2 times by mol or more relative to the azafluorene compound (II) as a raw material. In order to promote the reaction and prevent the raw material and an intermediate from remaining, the amount of the electron withdrawing group-substituted olefin (V) used is preferably 2.2 times by mol or more, more preferably 2.5 times by mol or more relative to the azafluorene compound (II) as a raw material.

<Base>

Examples of the base to be used include: hydroxides of alkali metals such as lithium hydroxide, sodium hydroxide, and potassium hydroxide; hydroxides of alkaline earth metals such as potassium hydroxide and barium hydroxide; carbonates of alkali metals such as sodium carbonate, sodium hydrogen carbonate, and potassium carbonate; carbonates of alkaline earth metals such as magnesium carbonate and calcium carbonate; alkali metal salts of phosphoric acid such as sodium phosphate, sodium hydrogen phosphate, and potassium phosphate; organic lithium salts such as n-butyllithium and tertiary butyllithium; alkoxide salts of alkali metals such as sodium methoxide, sodium ethoxide, and potassium tertiary butoxide; alkali metal hydrides such as sodium hydride and potassium hydride; tertiary amines such as triethylamine and diazabicycloundecene; quaternary ammonium hydroxides such as tetramethylammonium hydroxide, tetrabutylammonium hydroxide, and benzyltrimethylammonium hydroxide. These bases may be used singly or in combination of two or more of them.

A methylene group as a crosslinking group of the azafluorene compound (II) is readily subjected to a decomposition reaction in a solvent in the presence of a base. Therefore, a water-soluble inorganic base is preferably used because when the reaction is performed in a bilayer system including an organic layer and an aqueous layer, a side reaction such as a decomposition reaction can be inhibited. Among others, from the viewpoint of reactivity, an alkali metal hydroxide is preferred, and sodium hydroxide or potassium hydroxide is more preferred.

When sodium hydroxide is used as a base, the concentration of an aqueous solution (specifically, an aqueous sodium hydroxide solution) is usually 5 wt/vol % or more, preferably 10 wt/vol % or more, more preferably 25 wt/vol % or more because when the concentration of the aqueous solution is low, the reaction speed significantly reduces.

The upper limit of the amount of the base used is not particularly limited. However, when the amount of the base used relative to the azafluorene compound (II) as a raw material is too large, there is a case where a heavy load is applied to stirring or purification after the reaction. Therefore, when an aqueous sodium hydroxide solution is used as a base in a concentration of 25 wt/vol % or more, the amount of the base used is usually 20 times by volume or less, preferably 10 times by volume or less, more preferably 5 times by volume or less relative to the azafluorene compound (II). If the amount of the base is too small, the reaction speed significantly reduces, and therefore the amount of the base used is usually 0.2 times by volume or more, preferably 0.5 times by volume or more, more preferably 1 times by volume or more relative to the azafluorene compound (II) as a raw material.

<1-4-2-2-3. Phase Transfer Catalyst>

When the reaction is performed in a bilayer system including an organic layer and an aqueous layer in the step (iia), a phase transfer catalyst is preferably used to increase the reaction speed.

Examples of the phase transfer catalyst include: halides (except for fluorides) of quaternary ammonium salts such as tetramethylammonium chloride, tetrabutylammonium bromide, methyltrioctylammonium chloride, methyltridecylammonium chloride, benzyltrimethylammonium chloride, trioctylmethylammonium chloride, tetrabutylammonium iodide, acetyltrimethylammonium bromide, and benzyltriethylammonium chloride; halides (except for fluorides) of quaternary pyrrolidinium salts such as N,N-dimethylpyrrolidinium chloride, N-ethyl-N-methylpyrrolidinium iodide, N-butyl-N-methylpyrrolidinium bromide, N-benzyl-N-methylpyrrolidinium chloride, and N-ethyl-N-methylpyrrolidinium bromide; halides (except for fluorides) of quaternary morpholinium salts such as N-butyl-N-methylmorpholinium bromide, N-butyl-N-methylmorpholinium iodide, and N-allyl-N-methylmorpholinium bromide; and halides (except for fluorides) of quaternary piperidinium salts such as N-methyl-N-benzylpiperidinium chloride, N-methyl-N-benzylpiperidinium bromide, N,N-dimethylpiperidinium iodide, N-methyl-N-ethylpiperidinium acetate, N-methyl-N-ethylpiperidinium iodide; and crown ethers. These phase transfer catalysts may be used singly or in combination of two or more of them.

The phase transfer catalyst is preferably a quaternary ammonium salt, more preferably benzyltrimethylammonium chloride or benzyltriethylammonium chloride.

If the amount of the phase transfer catalyst used is too large relative to the azafluorene compound (II) as a raw material, a side reaction such as ester hydrolysis or successive Michael reaction tends to remarkably proceed, and further costs increase. From such a viewpoint, the amount of the phase transfer catalyst used is usually 5 times by mol or less, preferably 2 times by mol or less, more preferably 1 times by mol or less relative to the azafluorene compound (II). If the amount of the phase transfer catalyst used is too small, there is a case where the effect of increasing the reaction speed cannot sufficiently be obtained, and therefore the reaction speed significantly reduces. Therefore, the amount of the phase transfer catalyst used is usually 0.01 times by mol or more, preferably 0.1 times by mol or more, more preferably 0.5 times by mol or more relative to the azafluorene compound as a raw material.

<Solvent>

It is desirable that the step (iib) is performed using a solvent.

Specific examples of a usable solvent include: alkyl nitrile-based solvents such as acetonitrile and propionitrile; ketone-based solvents such as acetone, methyl ethyl ketone, and methyl isobutyl ketone; linear esters (it is to be noted that linear esters are a kind of ester-based solvents) such as methyl acetate, ethyl acetate, propyl acetate, phenyl acetate, methyl propionate, ethyl propionate, propyl propionate, phenyl propionate, methyl 3-methoxy propionate, methyl 3-ethoxy propionate, methyl lactate, and ethyl lactate; cyclic esters (it is to be noted that cyclic esters are a kind of ester-based solvents) such as γ-butyrolactone and caprolactone; ether esters (it is to be noted that ether esters are a kind of ester-based solvents) such as ethylene glycol monomethyl ether acetate, ethylene glycol monoethyl ether acetate, ethylene glycol monobutyl ether acetate, propylene glycol-1-monomethyl ether acetate, propylene glycol-1-monoethyl ether acetate; ether-based solvents such as diethyl ether, tetrahydrofuran, 1,4-dioxane, methyl cyclopentyl ether, and tertiary butyl methyl ether; halogen-based solvents such as 1,2-dichloroethane, dichloromethane, chloroform, and 1,1,2,2-tetrachloroethane; halogen-based aromatic hydrocarbons such as chlorobenzene and 1,2 dichlorobenzene; amide-based solvents such as N,N-dimethylformamide and N,N-dimethylacetamide; sulfoxide-based solvents such as dimethylsulfoxide and sulfolane; monocyclic aliphatic hydrocarbons (it is to be noted that monocyclic aliphatic hydrocarbons are a kind of cyclic aliphatic hydrocarbons) such as cyclopentane, cyclohexane, cycloheptane, and cyclooctane; monocyclic aliphatic hydrocarbon derivatives such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4- trimethylcyclohexane, and 1,3,5-trimethylcyclohexane; polycyclic aliphatic hydrocarbons (polycyclic aliphatic hydrocarbons are a kind of cyclic aliphatic hydrocarbons) such as decalin; acyclic aliphatic hydrocarbons such as n-pentane, n-hexane, n-heptane, n-octane, isooctane, n-nonane, n-decane, n-dodecane, and n-tetradecane; aromatic hydrocarbons such as toluene, p-xylene, o-xylene, and m-xylene; aromatic heterocycles such as pyridine; and alcohol-based solvents such as methanol, ethanol, isopropanol, n-butanol, tertiary butanol, hexanol, octanol, and cyclohexanol.

It has been found that the use of a solvent that causes phase separation from water tends to inhibit a side reaction such as a decomposition reaction of a methylene group as a crosslinking group of the azafluorene compound (II). Further, when a solvent capable of well dissolving the azafluorene compound (II) as a raw material is used, the reaction tends to successfully proceed, and therefore a solvent in which the solubility of the azafluorene compound (II) is 0.5 mass % or more at a temperature of 25° C. is preferably used. A solvent in which the solubility of the azafluorene compound (II) at a temperature of 25° C. is 1.0 mass % or more is more preferred, and a solvent in which the solubility is 1.5 mass % or more is even more preferred. More specifically, halogen-based aliphatic hydrocarbons, halogen-based aromatic hydrocarbons, aromatic hydrocarbons, or ether-based solvents are preferred, and dichloromethane, chlorobenzene, chloroform, 1,2-dichlorobenzene, tetrahydrofuran, 1,4-dioxane, or methyl cyclopentyl ether are more preferred.

These solvents may be used singly or in combination of two or more of them.

The upper limit of the amount of the solvent used is not particularly limited, but from the viewpoint of the generation efficiency of a desired product per reactor, the upper limit of the amount of the solvent used is 20 times by volume, preferably 15 times by volume, more preferably 10 times by volume the azafluorene compound (II) as a raw material. On the other hand, if the amount of the solvent used is too small, stirring is difficult due to poor solubility of the reagent, and the reaction slows down. Therefore, the lower limit of the amount of the solvent used is usually 1 times by volume, preferably 2 times by volume, more preferably 4 times by volume the azafluorene compound (II) as a raw material.

<Reaction Mode>

When the step (iia) is performed, the mode of the reaction is not particularly limited, and may be batch mode, flow-through mode, or a combination of them.

In the case of batch mode, when the electron withdrawing group-substituted olefin (V) is added to a reactor at a time at the start of the reaction, the electron withdrawing group-substituted olefin (V) is present in a high concentration, and therefore a polymerization reaction as a side reaction readily proceeds. From the viewpoint of inhibiting the side reaction, the electron withdrawing group-substituted olefin (V) is preferably successively added to a reactor little by little after the azafluorene compound (II) as a raw material, the phase transfer catalyst, the solvent, and the base are added to the reactor.

<Reaction Conditions>

If the temperature is too low in the step (iia), a sufficient reaction speed cannot be achieved. On the other hand, if the temperature is too high, the hydrolysis reaction of the electron withdrawing group-substituted olefin (V) and the azafluorene monomer (1a) as a product tends to readily proceed. Therefore, temperature control is preferably performed. More specifically, the lower limit of the reaction temperature is usually −20° C., preferably −10° C., more preferably −5° C. On the other hand, the upper limit of the reaction temperature is usually 40° C., preferably 30° C., more preferably 20° C., particularly preferably 5° C.

The lower limit of a general reaction time in the step (iia) is usually 15 minutes, preferably 30 minutes, more preferably 1 hour. The upper limit of the reaction time is not particularly limited, but is usually 20 hours, preferably 10 hours, more preferably 5 hours.

<Separation and Purification of Desired Product>

The azafluorene monomer (1a) as a desired product is separated and purified, for example, in the following manner. First, after the completion of the reaction, a by-produced metal halide and the remaining inorganic base are removed by filtration from a reaction liquid. Then, the azafluorene monomer (1a) as a desired product is precipitated and isolated by, for example, a method in which the solvent is concentrated or a method in which a poor solvent for the desired product is added.

Alternatively, after the completion of the reaction, the azafluorene monomer (1a) as a desired product may be extracted by adding acidic water and a solvent capable of dissolving the azafluorene monomer (1a) to a reaction liquid. The desired product extracted with the solvent can be isolated by, for example, a method in which the solvent is concentrated or a method in which a poor solvent is added.

The solvent that can be used for extraction is not particularly limited as long as the azafluorene monomer (1a) as a desired product can be dissolved therein. Specific examples of such a solvent to be used include: aromatic hydrocarbon compounds such as toluene and xylene; and halogen-based solvents such as dichloromethane and chloroform. These solvents may be used singly or in combination of two or more of them.

The azafluorene monomer (1a) obtained here can directly be used as a raw material monomer of a polyester or polyester carbonate or as a precursor of a raw material monomer of a polycarbonate, but may be purified before use. A purification method is not particularly limited, and a usual purification method can be used. More specifically, purification is performed by recrystallization, reprecipitation, extractive purification, or column chromatography. Alternatively, the azafluorene monomer (1a) may be dissolved in an appropriate solvent and then treated (specifically, purified) with activated carbon. The solvent that can be used at this time is the same as that usable for extraction.

When the azafluorene monomer (1a) obtained here has a carboxyl group, such an azafluorene monomer (1a) having a carboxyl group can be used as, for example, a raw material monomer of a polyester or polyester carbonate or as a precursor of a raw material monomer of a polycarbonate. The azafluorene monomer (1a) having a carboxyl group can be converted to an azafluorene monomer (1a) having an ester group by an esterification reaction.

<Step (iib) Method for Producing Azafluorene Monomer (1b) by Alkylation Reaction>

An azafluorene monomer (1b) can be produced through an alkylation reaction between an azafluorene compound (II) and an alkylation agent (VI-1) and an alkylation agent (VI-2) in the presence of a base.

[Formula 34]

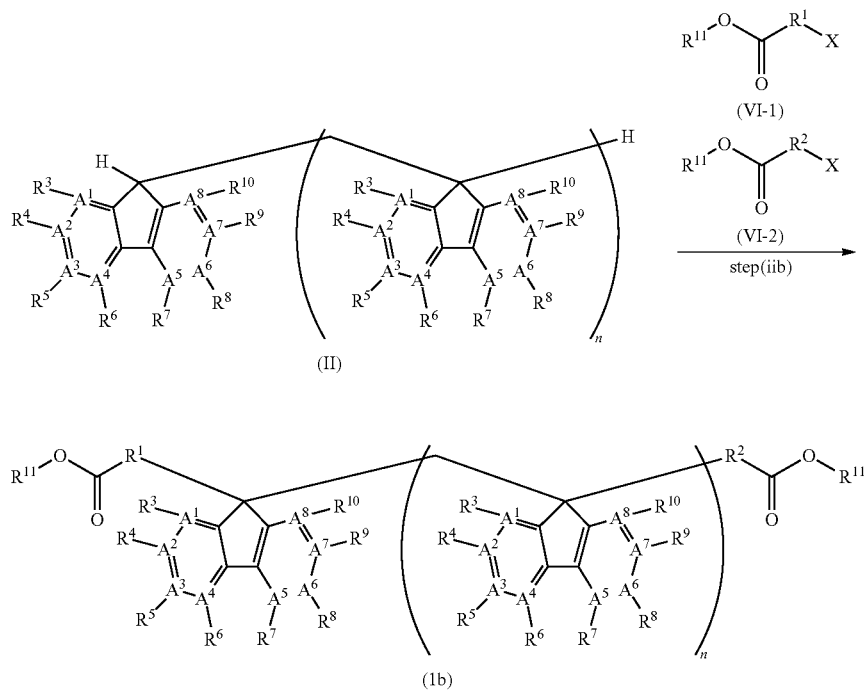

In the formula, $A^1$ to $A^8$, $R^1$ to $R^{11}$, and n are the same as those in the formulas (7) and (8), and X is a leaving group. Examples of the leaving group include halogen atoms (except for fluorine), a mesyl group, and a tosyl group.

Alkylation of fluorenes is widely known, and for example, there are reported 9,9-bis(haloalkyl)fluorenes such as 9,9-bis(bromohexyl)fluorene and 9,9-bis(iodohexyl)fluorene (see Gunin Saikia, Parameswar K. Iyer. "Facile C-H Alkylation in Water: Enabling Defect-Free Materials for Optoelectronic Devices." The Journal of Organic Chemistry, 1155 Sixteenth Street N.W. Washington, DC 20036, ACS Publications, 18 Mar. 2010, 75, 8, p. 2714-2717). On the basis of such knowledge, an azafluorene monomer (1b) can be synthesized using an azafluorene compound (II) as a raw material.

Examples of the alkylation agent used in the step (iib) include: alkyl haloalkanoates such as methyl chloroacetate, methyl bromoacetate, methyl iodoacetate, ethyl chloroacetate, ethyl bromoacetate, ethyl iodoacetate, propyl chloroacetate, n-butyl chloroacetate, tert-butyl chloroacetate, tert-butyl bromoacetate, tert-butyl iodoacetate, methyl 2-chloropropionate, methyl 2-bromopropionate, methyl 2-iodopropionate, ethyl 2-chloropropionate, tert-butyl 2-chloropropionate, tert-butyl 2-bromopropionate, ethyl 2-bromopropionate, ethyl 2-iodopropionate, methyl 3-chlorolactate, methyl 3-bromolactate, methyl 3-iodolactate, ethyl 3-chlorolactate, ethyl 3-iodolactate, and tert-butyl 2-iodopropionate; aryl haloalkanoates such as phenyl chloroacetate, phenyl bromoacetate, and phenyl iodoacetate; alkyl haloalkylbenzoates such as methyl 4-chloromethylbenzoate, methyl 4-bromomethylbenzoate, ethyl 4-chloromethylbenzoate, ethyl 4-bromomethylbenzoate, methyl 3-chloromethylbenzoate, and methyl 3-bromomethylbenzoate.

<Step (IIc): Method for Producing Compound Represented by Formula (8) in which $R^{11}$ and $R^{12}$ have Hydroxyester Group (Method for Producing Azafluorene Dihydroxyester (1c) by Interesterification Reaction of Azafluorene Monomer (1))>

An azafluorene dihydroxyester compound represented by the following general formula (1c) is produced from an azafluorene monomer (1) and a diol (VII) in the presence of a base according to the following step (iic).

[Formula 35]

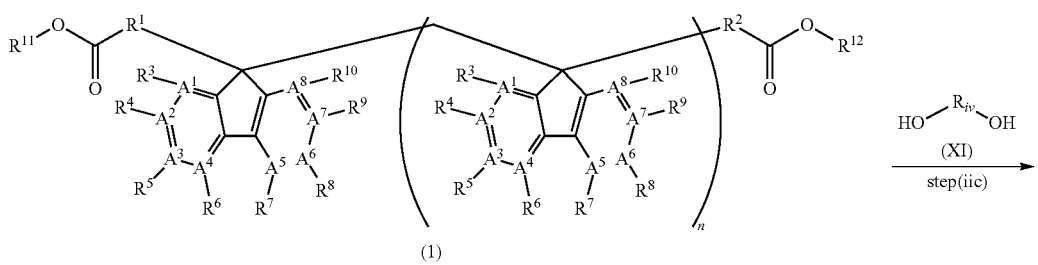

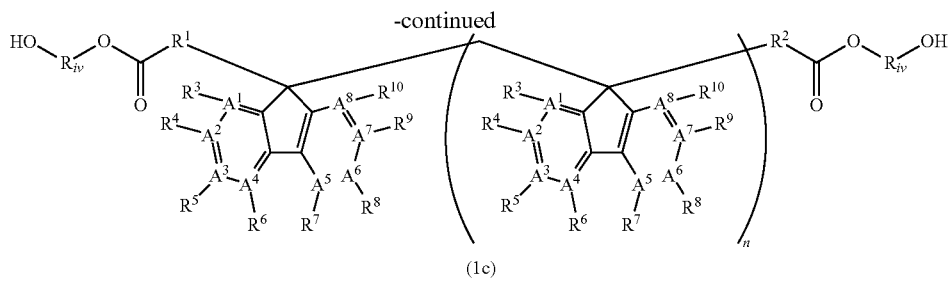

(1c)

In the formula, $A^1$ to $A^8$, $R^1$ to $R^{12}$, and n are the same as those in the formulas (7) and (8), and $R_{iv}$ is an organic substituent having 1 to 10 carbon atoms.

<Diol>

The diol (VII) used in the step (iic) is a diol having 1 to 10 carbon atoms. Specific examples of the diol include: chain alkylene diols (which may be either straight or branched) such as ethylene glycol, neopentyl glycol, 1,4-butanediol, and 1,6-hexanediol; cyclic alkylene diols such as cyclohexane dimethanol; oligoethylene glycols such as diethylene glycol, triethylene glycol, and tetraethylene glycol; secondary diols such as isosorbide; and aromatic diols such as resorcinol. These diols may be substituted with any substituent as long as the reaction is not inhibited.

Among them, alkylene glycols or oligoethylene glycols are preferred from the viewpoint of reaction speed and cost, and ethylene glycol is particularly preferred.

polycarbonate including a polyester carbonate or a raw material of a polyester, and therefore it is considered that even when contained in the azafluorene dihydroxyester compound (1c), the self-interesterified product (VIII) does not cause major problems as a raw material of a polycarbonate, a raw material of a polyester, or a raw material of a polyester carbonate. However, from the viewpoint of the quality of a polycarbonate, polyester, or polyester carbonate, the content of the self-interesterified product (VIII) is usually 0.1 times by mol or less, preferably 0.05 times by mol or less, more preferably 0.03 times by mol or less relative to the azafluorene dihydroxyester compound (1c) as a product. The amount of the diol (VII) used is usually 3 times by mol or more, preferably 10 times by mol or more, more preferably 50 times by mol or more relative to the azafluorene monomer (1).

[Formula 36]

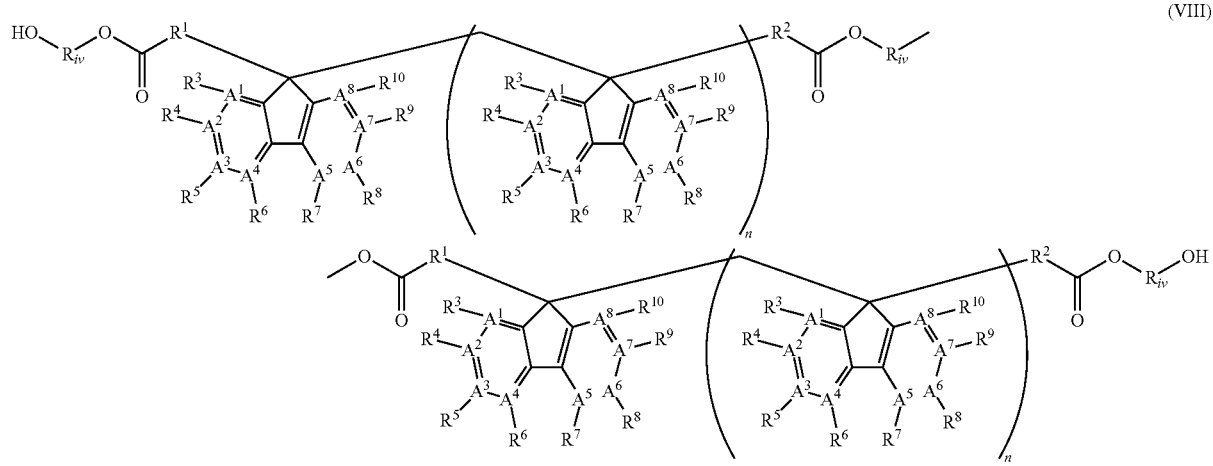

(VIII)

In the step (iic), two or more different kinds of diols (VII) may be used, but one kind of diol (VII) is usually used from the viewpoint of ease of purification.

When the amount of the diol (VII) used is larger, the reaction proceeds faster because a competitive reaction tends to occur between an alcohol generated from the organic substituent of the ester group of the azafluorene monomer (1) as a raw material and the diol (VII) added. Further, when the amount of the diol (VII) used is large, it is possible to prevent the generation of a by-product represented by the following general formula (VIII) in which azafluorene is crosslinked with the diol. The self-interesterified product (VIII) acts by itself as a raw material of a In the formula, $A^1$ to $A^8$, $R^1$ to $R^{10}$, and n are the same as those in the formulas (7) and (8), and $R_{iv}$ is an organic substituent having 1 to 10 carbon atoms.

The diol (VII) may be added at a time during preparation, or may be added dividedly during the progress of the reaction. The self-interesterified product represented by the general formula (VIII) can be converted to the azafluorene dihydroxyester compound (1c) by adding the diol (VII).

<Base>

Examples of the base used in the step (iic) include: alkali metal hydroxides such as lithium hydroxide, sodium hydroxide, and potassium hydroxide; hydroxides of alkaline earth metals such as calcium hydroxide and barium hydroxide; carbonates of alkali metals such as sodium carbonate, sodium hydrogen carbonate, and potassium carbonate; carbonates of alkaline earth metals such as magnesium carbonate and calcium carbonate; alkali metal salts of phosphoric acid such as sodium phosphate, sodium hydrogen phosphate, and potassium phosphate; organic lithium salts such as n-butyllithium and tertiary butyllithium; alkoxide salts of alkali metals such as sodium methoxide, sodium ethoxide, and potassium tertiary butoxide; alkali metal hydrides such as sodium hydride and potassium hydride; and quaternary ammonium hydroxides such as tetramethylammonium hydroxide and tetrabutylammonium hydroxide.

These bases may be used singly or in combination of two or more of them.

Among these bases, from the viewpoint of cost and reactivity, alkoxides of alkali metals are preferred, and particularly sodium methoxide or sodium ethoxide is more preferred.

The upper limit of the amount of the base used is not particularly limited, but if the amount of the base used is too large, a heavy load tends to be applied to stirring or purification after the reaction. Therefore, the amount of the base used is 10 times by mol or less, preferably 5 times by mol or less, more preferably 1 times by mol or less the azafluorene monomer (1).

On the other hand, if the amount of the base used is too small, the reaction tends to slow down. Therefore, the amount of the base used is usually 0.01 times by mol or more, preferably 0.05 times by mol or more, more preferably 0.1 times by mol or more the azafluorene monomer (1) as a raw material.

<Solvent>

The step (iic) may be performed in the absence of solvent, but may be performed using a solvent when the solubility of the azafluorene monomer (1) as a raw material in the diol (VII) as a reaction reagent is low and therefore reactivity with the diol is low.

Specific examples of a usable solvent include: alkyl nitrile-based solvents such as acetonitrile and propionitrile; ether-based solvents such as diethyl ether, tetrahydrofuran, 1,4-dioxane, methyl cyclopentyl ether, tertiary butyl methyl ether, diethylene glycol dimethyl ether, and triethylene glycol dimethyl ether; halogen-based solvents such as 1,2-dichloroethane, dichloromethane, chloroform, and 1,1,2,2-tetrachloroethane; halogen-based aromatic hydrocarbons such as chlorobenzene and 1,2-dichlorobenzene; amide-based solvents such as N,N-dimethylformamide and N,N-dimethylacetamide; sulfoxide-based solvents such as dimethylsulfoxide and sulfolane; monocyclic aliphatic hydrocarbons (it is to be noted that monocyclic aliphatic hydrocarbons are a kind of cyclic aliphatic hydrocarbons) such as cyclopentane, cyclohexane, cycloheptane, and cyclooctane; monocyclic aliphatic hydrocarbon derivatives such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, and 1,3,5-trimethylcyclohexane; polycyclic aliphatic hydrocarbons (polycyclic aliphatic hydrocarbons are a kind of cyclic aliphatic hydrocarbons) such as decalin; acyclic aliphatic hydrocarbons such as n-pentane, n-hexane, n-heptane, n-octane, isooctane, n-nonane, n-decane, n-dodecane, and n-tetradecane; and aromatic hydrocarbons such as toluene, p-xylene, o-xylene, and m-xylene. These solvents may be used singly or in combination of two or more of them.

Among these solvents, ether-based solvents are preferred because the reaction tends to successfully proceed when a solvent in which both the azafluorene monomer (1) as a raw material and the diol (VII) are highly soluble is used. Further, diethylene glycol dimethyl ether or triethylene glycol dimethyl ether is particularly preferred because the reaction can be performed at high temperature.

The upper limit of the amount of the solvent used is not particularly limited, but from the viewpoint of the generation efficiency of a desired product per reactor, the upper limit of the amount of the solvent used is usually 20 times by volume, preferably 15 times by volume, more preferably 10 times by volume the azafluorene monomer (1) as a raw material. On the other hand, if the amount of the solvent used is too small, stirring is difficult due to poor solubility of the reagent, and the reaction tends to slow down. Therefore, the lower limit of the amount of the solvent used is usually 1 times by volume, preferably 2 times by volume, more preferably 4 times by volume the azafluorene monomer (1) as a raw material.

<Reaction Mode>

When the step (iic) is performed, the mode of the reaction is not particularly limited, and may be batch mode, flow-through mode, or a combination of them.

<Reaction Conditions>

When the solvent and the diol (VII) as a reaction reagent contain moisture, ester hydrolysis proceeds so that a dicarboxylic acid (IX) or a hydroxycarboxylic acid (X) shown below tends to be generated as a by-product. The amount of the by-product tends to increase as the amount of moisture increases. In order to reduce the amount of the by-product, it is preferred that the solvent and the diol (VII) as a reaction reagent are anhydrous, or azeotropic dehydration is performed using a solvent, such as toluene or xylene, that is not involved in the reaction but is azeotropic with water before the reaction.

[Formula 37]

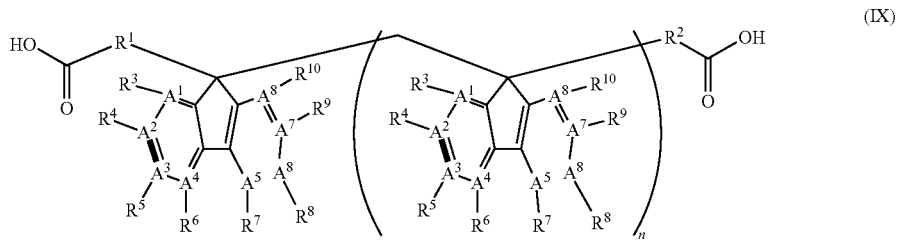

(IX)

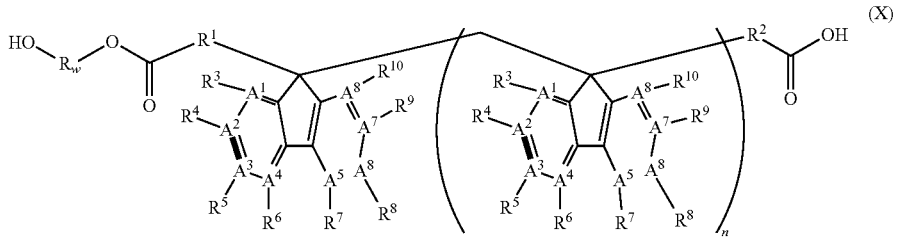

In the formula, $A^1$ to $A^8$, $R^1$ to $R^{10}$, and n are the same as those in the formulas (7) and (8), and $R_{iv}$ is an organic substituent having 1 to 10 carbon atoms.

It is to be noted that the dicarboxylic acid (IX) or the hydroxycarboxylic acid (X) can also be used as a raw material of a polycarbonate including a polyester carbonate or a raw material of a polyester.

In the step (iic), a sufficient reaction speed tends not to be achieved if the temperature is too low. Therefore, the lower limit of the reaction temperature is usually 20° C., preferably 50° C., more preferably 80° C. On the other hand, the upper limit of the reaction temperature is usually 150° C., preferably 120° C., more preferably 100° C.

The lower limit of a general reaction time in the step (iic) is usually 1 hour, preferably 2 hours, more preferably 4 hours. The upper limit of the reaction time is not particularly limited, but is usually 30 hours, preferably 20 hours, more preferably 10 hours.

<Separation and Purification of Desired Product>

The azafluorene dihydroxyester compound (1c) as a desired product is separated and purified, for example, in the following manner. First, after the completion of the reaction, insoluble substances such as a by-produced metal halide and the remaining inorganic base are removed by filtration from a reaction liquid. Then, the azafluorene dihydroxyester compound (1c) as a desired product is precipitated and isolated by, for example, a method in which the solvent is concentrated or a method in which a poor solvent for the desired product is added.

Alternatively, after the completion of the reaction, the azafluorene dihydroxyester compound (1c) as a desired product may be extracted by adding acidic water and a solvent capable of dissolving the azafluorene dihydroxyester compound (1c) to a reaction liquid. The desired product extracted with the solvent can be isolated by, for example, a method in which the solvent is concentrated or a method in which a poor solvent is added. Further, the desired product extracted with the solvent may be washed with an aqueous solution of sodium carbonate or potassium carbonate to remove a carboxylic acid as a by-product.

The solvent that can be used for extraction is not particularly limited as long as the azafluorene dihydroxyester compound (1c) as a desired product can be dissolved therein. Specific examples of such a solvent to be used include: ester-based solvents such as ethyl acetate; aromatic hydrocarbon compounds such as toluene and xylene; and halogen-based solvents such as dichloromethane and chloroform. These solvents may be used singly or in combination of two or more of them.

The azafluorene dihyroxyester compound (1c) may directly be used for polymerization as a raw material of a polycarbonate including a polyester carbonate or a raw material of a polyester, or may be purified before use. A purification method is not particularly limited, and a usual purification method can be used. More specifically, purification is performed by recrystallization, reprecipitation, or extractive purification. Alternatively, the azafluorene dihydroxyester compound (1c) may be dissolved in an appropriate solvent and then treated (specifically, purified) with activated carbon. The solvent that can be used at this time is the same as that usable for extraction.

<Method for Producing Azafluorene Diaryl Ester Compound Represented by General Formula (1d) (Method for Producing Azafluorene Diaryl Ester Compound (1d) by Interesterification Reaction after Synthesis of Azafluorene Diester Compound (1)>

An azafluorene diaryl ester compound (1d) can be produced by a method including a step (step (iia) or step (iib)) of synthesizing an azafluorene diester compound (1), followed by an interesterification reaction with a diaryl carbonate (XI) (step (iid)).

[Formula 38]

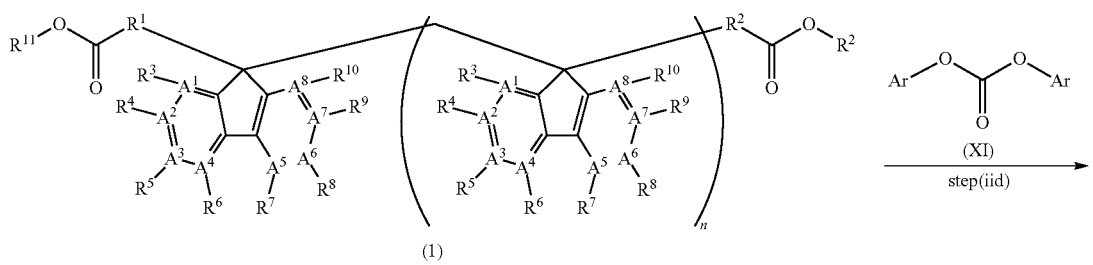

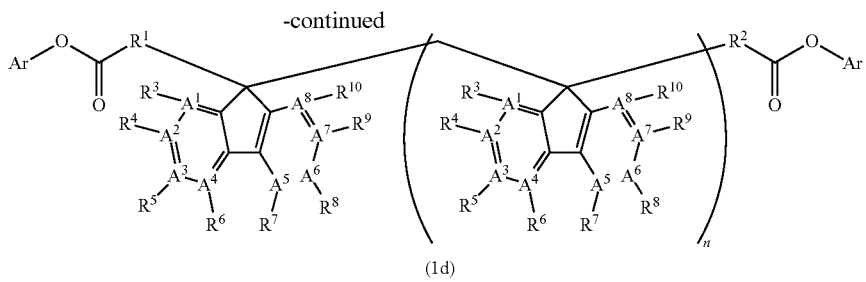

(1d)

In the formula, $A^1$ to $A^8$, $R^1$ to $R^{12}$, and n are the same as those in the formulas (7) and (8), and Ar is an aryl group having 6 to 11 carbon atoms.

<Diaryl Carbonate (XI)>

The diaryl carbonate (XI) is a reaction reagent. Examples of the diaryl carbonate (XI) include diphenyl carbonate, ditolyl carbonate, bis(chlorophenyl)carbonate, m-cresyl carbonate, dinaphthyl carbonate, and bis(biphenyl) carbonate. Among them, diphenyl carbonate is preferred because it is inexpensive and industrially available. These diaryl carbonates may be used singly or in combination of two or more of them.

The upper limit of the diaryl carbonate (XI) used is not particularly limited. However, if the amount of the diaryl carbonate (XI) is too large relative to the azafluorene monomer (1) as a raw material, a heavy load tends to be applied to purification after the reaction. Therefore, the amount of the diaryl carbonate (XI) used is usually 20 times by mol or less, preferably 10 times by mol or less, more preferably 5 times by mol or less the azafluorene monomer. On the other hand, if the amount of the diaryl carbonate (XI) used is too small, there is a case where the azafluorene monomer (1) as a raw material remains in a product, or an azafluorene monoaryl ester compound (1e) shown below is generated as an intermediate and remains in a final product. In order to prevent this, the amount of the diaryl carbonate (XI) used is usually 1 times by mol or more, preferably 1.5 times by mol or more, more preferably 2 times by mol or more the azafluorene monomer (1) as a raw material.

diisopropoxide bis(acetylacetonate); alkali metal compounds such as lithium carbonate, dibutylamino lithium, lithium acetylacetonate, sodium phenoxide, and potassium phenoxide; cadmium compounds such as cadmium acetylacetonate and cadmium carbonate; zirconium compounds such as zirconium acetylacetonate and zirconocene; lead compounds such as lead sulfide, lead hydroxide, plumbate, zincate, lead carbonate, lead acetate, tetrabutyllead, tetraphenyllead, triphenyllead, dimethoxylead, and diphenoxylead; copper compounds such as copper acetate, copper bisacetylacetonate, copper oleate, butylcopper, dimethoxycopper, and copper chloride; iron compounds such as iron hydroxide, iron carbonate, triacetoxyiron, trimethoxyiron, and triphenoxyiron; zinc compounds such as zinc bisacetylacetonate, diacetoxyzinc, dimethoxyzinc, diethoxyzinc, and diphenoxyzinc; organic tin compounds such as di-n-butyltin oxide, diphenyltin oxide, di-n-octyltin oxide, di-n-butyltin dimethoxide, di-n-butyltin diacrylate, di-n-butyltin dimethacrylate, di-n-butyltin dilaurate, tetramethoxytin, tetraphenoxytin, and tetrabutyl-1,3-diacetoxydistannoxane; aluminum compounds such as aluminum acetate, aluminum methoxide, aluminum ethoxide, and aluminum phenoxide; vanadium compounds such as vanadium dichloride, vanadium trichloride, vanadium tetrachloride, and vanadium sulfate; and phosphonium salts such as tetraphenylphosphonium phenoxide. These interesterification reaction catalysts may be used singly or in combination of two or more of them.

[Formula 39]

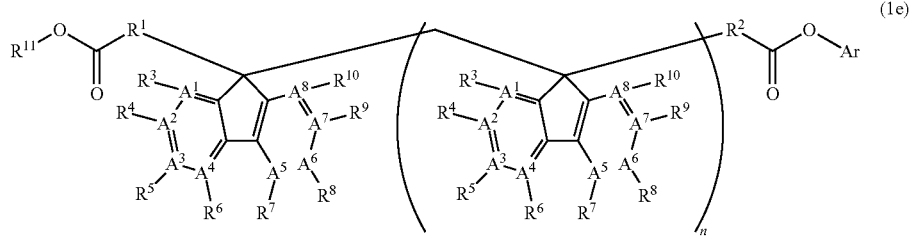

(1e)

In the formula, $A^1$ to $A^8$, $R^1$ to $R^{11}$, and n are the same as those in the formulas (7) and (8), and Ar is an aryl group having 6 to 11 carbon atoms.

<Interesterification Reaction Catalyst>

Examples of an interesterification reaction catalyst include: titanium compounds such as tetrabutoxytitanium, tetraisobutoxytitanium, tetramethoxytitanium, tetraisopropoxytitanium, tetraethoxytitanium, tetrakis(2-ethylhexyloxy)titanium, tetrastearyloxytitanium, tetraphenoxytitanium, titanium (IV) acetylacetonate, and titanium (IV)

Among them, phosphonium salts, lithium compounds, zirconium compounds, organic tin compounds, or titanium compounds are preferably used because they are industrially inexpensive and advantageous in terms of reaction operation. Among them, organic tin compounds or titanium compounds are particularly preferred.

The upper limit of the interesterification reaction catalyst used is not particularly limited. However, if the amount of the interesterification reaction catalyst used is too large, a heavy load is applied to purification after the reaction, and therefore the upper limit of the amount of the interesterification reaction catalyst used is usually 20 mol % or less, preferably 10 mol % or less, more preferably 5 mol % or less relative to the azafluorene monomer (1).

On the other hand, if the amount of the interesterification reaction catalyst used is too small, there is a case where the reaction time is too long. Therefore, the amount of the interesterification reaction catalyst used is usually 0.1 mol % or more, preferably 0.5 mol % or more, more preferably 1 mol % or more relative to the azafluorene monomer as a raw material.

<Solvent>

In the step (iid), a reaction solvent may be used, but the reaction is preferably performed using only the azafluorene monomer (1) as a raw material, the diaryl carbonate (XI), and the interesterification reaction catalyst without using a reaction solvent. However, when the azafluorene monomer (1) as a raw material and the diaryl carbonate (XI) are solid at ordinary temperature and are therefore difficult to stir, a reaction solvent may be used. When a reaction solvent is used, the kind thereof is not limited as long as the azafluorene monomer (1) as a raw material, the diaryl carbonate (XI), and the interesterification reaction catalyst can appropriately be dissolved and/or dispersed therein.

Specific examples of such a usable solvent include: alkyl nitrile-based solvents such as acetonitrile and propionitrile; ketone-based solvents such as acetone, methyl ethyl ketone, and methyl isobutyl ketone; ether-based solvents such as diethyl ether, tetrahydrofuran, 1,4-dioxane, methyl cyclopentyl ether, and tertiary butyl methyl ether; halogen-based solvents such as 1,2-dichloroethane, dichloromethane, chloroform, and 1,1,2,2-tetrachloroethane; halogen-based aromatic hydrocarbons such as chlorobenzene and 1,2-dichlorobenzene; amide-based solvents such as N,N-dimethylformamide and N,N-dimethylacetamide; sulfoxide-based solvents such as dimethylsulfoxide and sulfolane; monocyclic aliphatic hydrocarbons (it is to be noted that monocyclic aliphatic hydrocarbons are a kind of cyclic aliphatic hydrocarbons) such as cyclopentane, cyclohexane, cycloheptane, and cyclooctane; monocyclic aliphatic hydrocarbon derivatives such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, and 1,3,5-trimethylcyclohexane; polycyclic aliphatic hydrocarbons (it is to be noted that polycyclic aliphatic hydrocarbons are a kind of cyclic aliphatic hydrocarbons) such as decalin; acyclic aliphatic hydrocarbons such as n-pentane, n-hexane, n-heptane, n-octane, isooctane, n-nonane, n-decane, n-dodecane, and n-tetradecane; and aromatic hyhdrocarbons such as toluene, p-xylene, o-xylene, m-xylene, 1,3,5-trimethylbenzene, 1,2,4-trimethylbenzene, and 1,2,3,4-tetrahydronaphthalene. These solvents may be used singly or in combination of two or more of them.

It is preferred that the reaction in the step (iid) is usually performed at a high temperature of 100° C. or more. Therefore, among the above-mentioned solvents, preferred are solvents having a boiling point of 100° C. or more, such as chlorobenzene, 1,2-dichlorobenzene, trichlorobenzene, toluene, p-xylene, o-xylene, m-xylene, 1,3,5-trimethylbenzene, 1,2,4-trimethylbenzene, 1,2,3,4-tetrahydronaphthalene, decahydronaphthalene, N,N-dimethylformamide, N,N-dimethylacetamide, dimethylsulfoxide, and sulfolane. Particularly preferred are solvents that are capable of appropriately dissolving the azafluorene diester compound (1) as a raw material, have a boiling point of 130° C. or more, and allow the reaction to be performed at a higher temperature, such as 1,2-dichlorobenzene, xylene, 1,3,5-trimethylbenzene, 1,2,4-trimethylbenzene, 1,2,3,4-tetrahydronaphthalene, and decahydronaphthalene.

The upper limit of the amount of the solvent used is not particularly limited, but from the viewpoint of improving the generation efficiency of a desired product per reactor, the upper limit of the amount of the solvent used is usually 15 times by volume, preferably 10 times by volume, more preferably 5 times by volume the azafluorene monomer (1) as a raw material. On the other hand, if the amount of the solvent used is too small, stirring is difficult due to poor solubility of the reagent, and the reaction slows down. Therefore, the lower limit of the amount of the solvent used is usually 0.5 times by volume, preferably 1 times by volume, more preferably 2 times by volume the azafluorene monomer (1) as a raw material.

<Reaction Mode>

When the step (iid) is performed, the mode of the reaction is not particularly limited, and may be batch mode, flow-through mode, or a combination of them.

<Reaction Conditions>

In the reaction in the step (iid), a sufficient reaction speed tends not to be achieved if the temperature is too low. Therefore, the lower limit of the reaction temperature is usually 50° C., preferably 70° C., more preferably 100° C. On the other hand, the upper limit of the reaction temperature is usually 250° C., preferably 200° C., more preferably 180° C.

The lower limit of the reaction time in the step (iid) is usually 1 hour, preferably 2 hours, more preferably 3 hours. The upper limit of the reaction time is not particularly limited, but is usually 30 hours, preferably 20 hours, more preferably 10 hours.

In the step (iid), in order to shift the equilibrium to the product side, the reaction may be performed while by-products are distilled away under reduced pressure. In this case, the pressure is usually reduced to 20 kPa or less, preferably 10 kPa or less, more preferably 5 kPa or less. On the other hand, if the pressure is excessively reduced, there is a possibility that the diaryl carbonate used as a reagent is sublimated. From the viewpoint of preventing sublimation, the pressure is usually 0.1 kPa or more, preferably 0.5 kPa or more, more preferably 1.0 kPa or more.

<Separation and Purification of Desired Product>

After the completion of the reaction, the azafluorene diaryl ester monomer (1d) as a desired product can be precipitated and isolated by adding a poor solvent to a reaction liquid.

Alternatively, after the completion of the reaction, a desired product may be extracted by adding a solvent capable of dissolving the azafluorene diaryl ester monomer (1d) as a desired product and water to a reaction liquid. The desired product extracted with the solvent is isolated by, for example, a method in which the solvent is concentrated or a method in which a poor solvent is added.

The obtained azafluorene diaryl ester monomer (1d) may directly be used for polymerization as a raw material of a polycarbonate including a polyester carbonate or a raw material of a polyester, or may be purified before use. A purification method is not particularly limited, and a usual purification method can be used. More specifically, purification is performed by recrystallization, reprecipitation, extractive purification, or column chromatography.

<Method for Producing Diol Compound Represented by General Formula (7)>
(Method for Producing Diol Compound (7) by Reduction Reaction after Synthesis of Diester Compound (8))

A Method for Producing a Diol Compound (7) is not Particularly Limited, but a Diol compound (7) can be obtained by, for example, a reduction reaction using a diester compound (8) as a starting material.

[Formula 40]

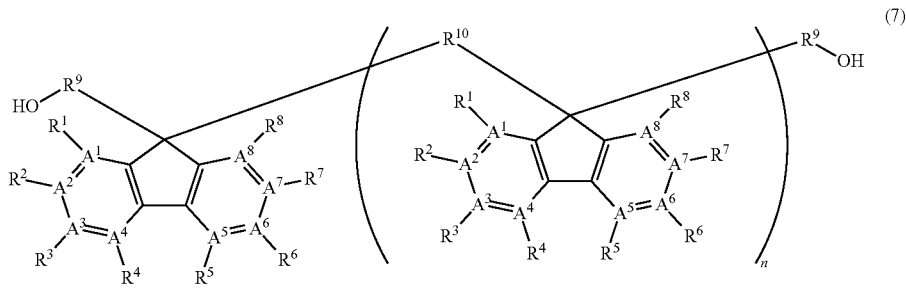

(7)

A method for synthesizing a diol by ester reduction is well known. U.S. Patent Application Publication No. 2012/0170118 discloses a diol produced by ester reduction using lithium aluminum hydride as a reducing agent. As a metal hydride, diisobutyl aluminum hydride or sodium bis(2-methoxyethoxy)aluminum hydride may also be used. Also, a method is widely known in which an ester is reduced by catalytic hydrogenation using ruthenium, rhodium, palladium, or platinum as a catalyst.

(Method for Producing a Compound Represented by General Formula (7) in which $R^9$ is Methylene Group)

The diol compound (7) in which $R^9$ is a methylene group is produced from an azafluorene compound (II) and a formaldehyde by reaction in the presence of a base.

<Formaldehyde>

The formaldehyde is not particularly limited as long as formaldehyde can be supplied to a reaction system. Specific examples of the formaldehyde include gaseous formaldehyde, an aqueous formaldehyde solution, paraformaldehyde obtained by polymerizing formaldehyde, and trioxane. Paraformaldehyde is preferably used because it is industrially inexpensive and powdery, and is therefore easily handled and can accurately be weighed.

The upper limit of the amount of the formaldehyde used is not particularly limited. However, if the amount of the formaldehyde used is too large, a heavy load tends to be applied to purification after the reaction, and therefore the amount of the formaldehyde used is usually 20 times by mol or less, preferably 10 times by mol or less, more preferably 5 times by mol or less relative to the azafluorene compound (II). The lower limit of the formaldehyde used is theoretically 2 times by mole relative to the raw material, and therefore the amount of the formaldehyde used is usually 2 times by mol or more. In order to promote the reaction and prevent the raw material and the intermediate from remaining, the formaldehyde may be used slightly excessively relative to the azafluorene compound (II) as a raw material without any problem. From such a viewpoint, the amount of the formaldehyde used is preferably 2.1 times by mol or more, more preferably 2.2 times by mole or more relative to the oligofluorene compound (II) as a raw material.

<Base>

Examples of the base to be used include: hydroxides of alkali metals such as lithium hydroxide, sodium hydroxide, and potassium hydroxide; hydroxides of alkaline earth metals such as calcium hydroxide and barium hydroxide; carbonates of alkali metals such as sodium carbonate, sodium hydrogen carbonate, and potassium carbonate; carbonates of alkaline earth metals such as magnesium carbonate and calcium carbonate; alkali metal salts of phosphoric acid such as sodium phosphate, sodium hydrogen phosphate, and potassium phosphate; organic lithium salts such as n-butyllithium and tertiary butyllithium; alkoxide salts of alkali metals such as sodium methoxide, sodium ethoxide, and potassium tertiary butoxide; alkali metal hydrides such as sodium hydride and potassium hydride; tertiary amines such as triethylamine and diazabicycloundecene; and quaternary ammonium hydroxides such as tetramethylammonium hydroxide and tetrabutylammonium hydroxide. These interesterification reaction catalysts may be used singly or in combination of two or more of them.

Preferred bases are alkoxides of alkali metals because they exhibit sufficient basicity in the reaction. Further, more preferred bases are sodium methoxide and sodium ethoxide because they are industrially inexpensive. The alkali metal alkoxide may be used in the form of powder or may be a liquid such as an alcohol solution. The alkali metal alkoxide may be prepared by reacting an alkali metal and an alcohol.

When the base is used in an excessive amount, the decomposition reaction of the diol compound (7) tends to proceed. Therefore, the amount of the base used is usually 1 times by mol or less, preferably 0.5 times by mol or less, more preferably 0.2 times by mol or less relative to the azafluorene compound (II) as a raw material. On the other hand, if the amount of the base used is too small, the reaction slows down. Therefore, the amount of the base used is usually 0.01 times by mol or more, preferably 0.05 times by mol or more relative to the azafluorene compound (II) as a raw material.

The synthesis reaction preferably uses a solvent. Examples of a usable solvent are shown below. Specific examples of an alkylnitrile-based solvent to be used include acetonitrile and propionitrile. Specific examples of a ketone-based solvent to be used include acetone, methyl ethyl ketone, and methyl isobutyl ketone. Specific examples of an ester-based solvent to be used include: linear esters such as methyl acetate, ethyl acetate, propyl acetate, phenyl acetate, methyl propionate, ethyl propionate, propyl propionate, phenyl propionate, methyl 3-methoxypropionate, methyl 3-ethoxypropionate, methyl lactate, and ethyl lactate; cyclic esters such as γ-butyrolactone and caprolactone; ether esters such as ethylene glycol monomethyl ether acetate, ethylene glycol monoethyl ether acetate, ethylene glycol monobutyl ether acetate, propylene glycol-1-monomethyl ether acetate, and propylene glycol-1-monoethyl ether acetate. Specific examples of an ether-based solvent to be used include diethyl ether, tetrahydrofuran, 1,4-dioxane, methyl cyclopentyl ether, and tertiary butyl methyl ether. Specific examples of a halogen-based solvent to be used include 1,2-dichloroethane, dichloromethane, chloroform, and 1,1,2,2-tetrachloroethane. Specific examples of a halogen-based aromatic hydrocarbon to be used include chlorobenzene and 1,2-dichlorobenzene. Specific examples of an amide-based solvent to be used include N,N-dimethylformamide, N,N-dimethylacetamide, and N-methylpyrrolidone. Specific examples of a sulfoxide-based solvent to be used include dimethylsulfoxide and sulfolane. Specific examples of a cyclic aliphatic hydrocarbon to be used include: monocyclic aliphatic hydrocarbons such as cyclopentane, cyclohexane, cycloheptane, and cyclooctane; monocyclic aliphatic hydrocarbon derivatives such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, and 1,3,5-trimethylcyclohexane; polycyclic aliphatic hydrocarbons such as decalin; and acyclic aliphatic hydrocarbons such as n-pentane, n-hexane, n-heptane, n-octane, isooctane, n-nonane, n-decane, n-dodecane, and n-tetradecane. Specific examples of an aromatic hydrocarbon to be used include toluene, p-xylene, o-xylene, and m-xylene. Specific examples of an alcohol-based solvent to be used include methanol, ethanol, isopropanol, n-butanol, tertiary butanol, hexanol, octanol, and cyclohexanol.

Among the above-mentioned solvents, an amide-based solvent or a sulfoxide-based solvent as a polar solvent is preferred, and N,N-dimethylformamide is particularly preferred, because the solubility of an anion generated from the azafluorene compound (II) is high, and therefore the reaction tends to successfully proceed. These solvents may be used singly or in combination of two or more of them. The upper limit of the amount of the solvent used is not particularly limited, but from the viewpoint of the generation efficiency of a desired product per reactor, the upper limit of the amount of the solvent used is usually 10 times by volume, preferably 7 times by volume, more preferably 4 times by volume the azafluorene compound (II) as a raw material. On the other hand, if the amount of the solvent used is too small, stirring is difficult and the reaction tends to slow down. Therefore, the lower limit of the amount of the solvent used is usually 1 times by volume, preferably 2 times by volume, more preferably 3 times by volume the azafluorene compound (II) as a raw material.

<Reaction Mode>

The mode of the reaction is not particularly limited, and may be batch mode, flow-through mode, or a combination of them. In the case of batch mode, it is known that when the base as a reaction reagent is added to a reactor at a time at the start of the reaction, the decomposition reaction is likely to proceed, and therefore the base is preferably added little by little after the azafluorene compound (II) as a raw material, the formaldehyde, and the solvent are added.

<Reaction Conditions>

If the temperature is too low, a sufficient reaction speed is not achieved, and on the other hand if the temperature is too high, the decomposition reaction tends to proceed. Therefore, the reaction temperature is preferably controlled. When N,N-dimethylformamide as an optimum solvent and sodium ethoxide as an optimum base are used, the lower limit of the reaction temperature is usually −50° C., and the upper limit of the reaction temperature is usually 30° C. More specifically, when $R^{10}$ is a methylene group and n=1, the upper limit of the reaction temperature is preferably 20° C., more preferably 10° C. On the other hand, the lower limit of the reaction temperature is preferably −20° C., more preferably 0° C. or more. When $R^3$ is an ethylene group and n=1, the upper limit of the reaction temperature is preferably 25° C., more preferably 20° C. On the other hand, the lower limit of the reaction temperature is preferably 0° C., more preferably 10° C. When $R^{10}$ is a methylene group and n=2, the upper limit of the reaction temperature is preferably 25° C., more preferably 20° C. On the other hand, the lower limit of the reaction temperature is preferably 0° C., more preferably 10° C.

<Separation and Purification of Desired Product>

After the completion of the reaction, the diol compound (7) as a desired product can be precipitated and isolated by adding a reaction liquid to acidic water such as dilute hydrochloric acid or by adding acidic water such as dilute hydrochloric acid to a reaction liquid. Alternatively, after the completion of the reaction, the diol compound (7) as a desired product may be extracted by adding a solvent capable of dissolving the diol compound (7) and water to a reaction liquid. The desired product extracted with the solvent can be isolated by, for example, a method in which the solvent is concentrated or a method in which a poor solvent is added.

The obtained diol compound (7) may directly be used for polymerization as a raw material of a polymer, but may be purified before polymerization. A purification method is not particularly limited, and a usual purification method can be used. More specifically, recrystallization, reprecipitation, extractive purification, column chromatography, or the like may be used.

The presence of metal components often has an adverse effect on the polymerization reaction. The content of Group-1 and Group-2 metals of the long periodic table in the monomer is preferably 500 ppm by mass or less, more preferably 200 ppm by mass or less, even more preferably 50 ppm by mass or less, particularly preferably 10 ppm by mass or less. Generally, liquid-liquid separation is very effective for removing metal components. However, the diol compound (7) as a desired product is dissolved in a highly polar solvent such as N,N-dimethylformamide or tetrahydrofuran, and therefore it is very difficult to perform liquid-liquid separation of a bilayer system. On the other hand, even when the precipitate after the termination of the reaction is washed with water or purified by an ordinary method in which the precipitate is washed by adding any solvent (liquid), heating, and suspending the precipitate in the solvent, it is still difficult to fully remove metal components as contaminants, and there is a case where metal components remain in the precipitate on the order of a few hundred ppm by mass. Therefore, as a simple and effective method for removing inorganic salts (i.e., a purification method), a method is preferred in which the reaction precipitate containing impurities is dissolved in a highly polar solvent such as N,N-dimethylformamide or tetrahydrofuran, and then water is added to the solution for precipitation.

<Specific Examples of Azafluorene Monomer>

Specific examples of the azafluorene monomer represented by the formula (7) in which n=0 are shown below as group [N].

[Formula 41]
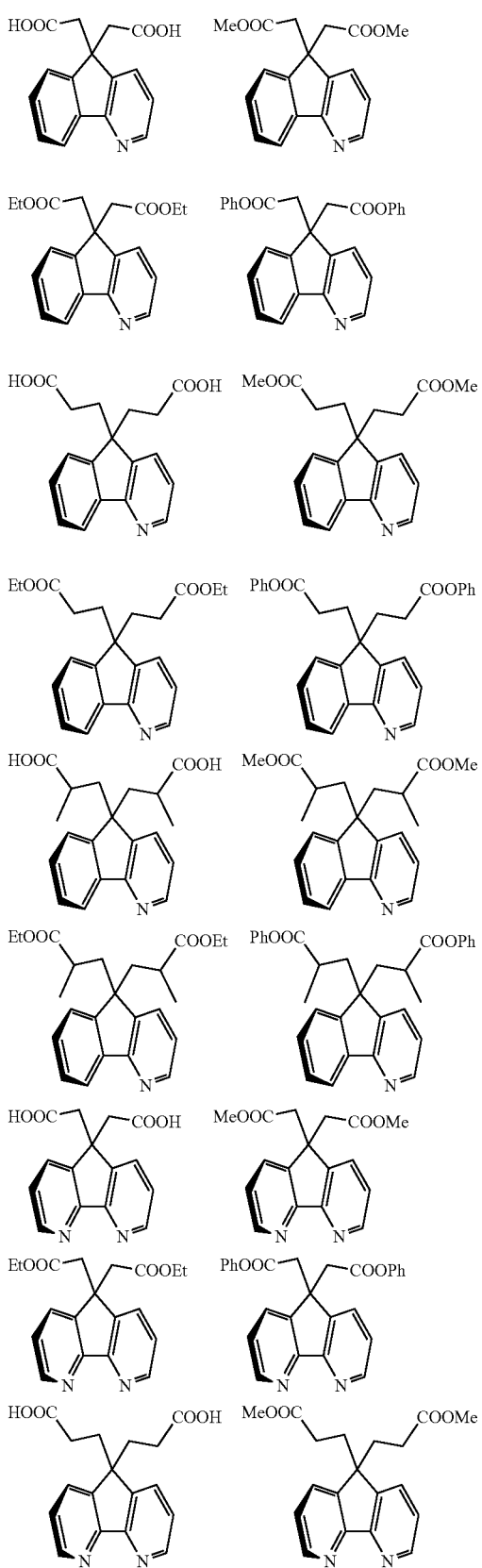
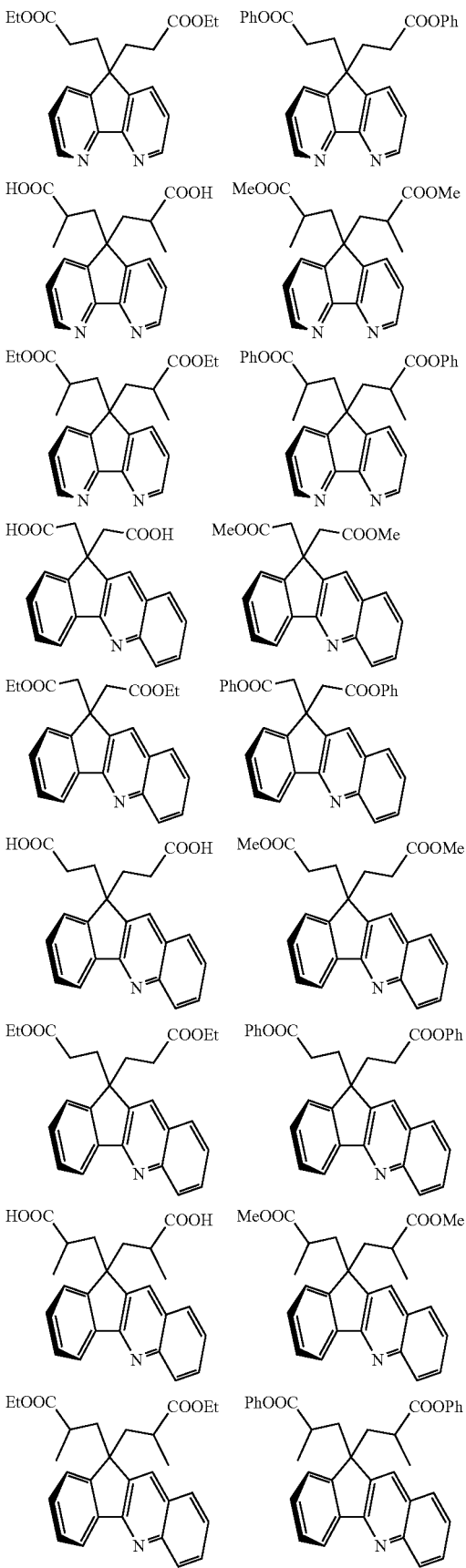

-continued
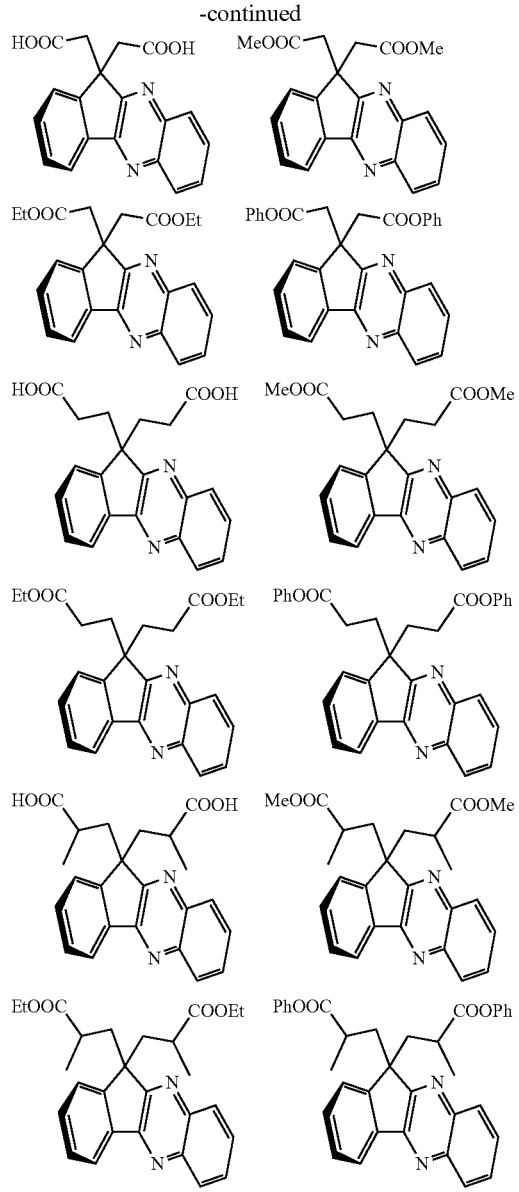
[Formula 42]
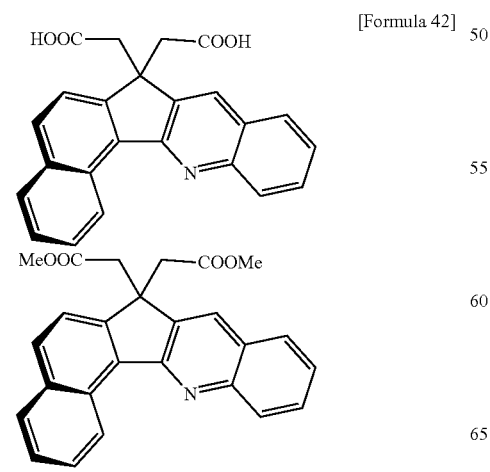
-continued
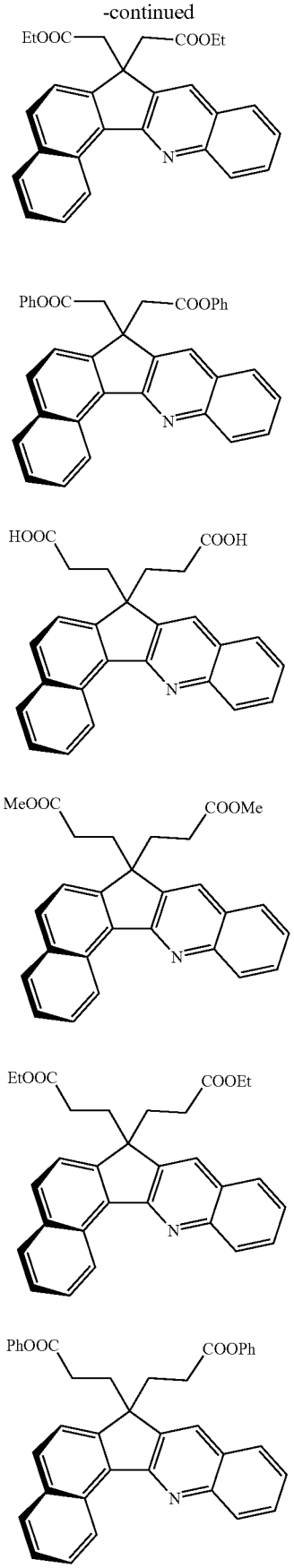

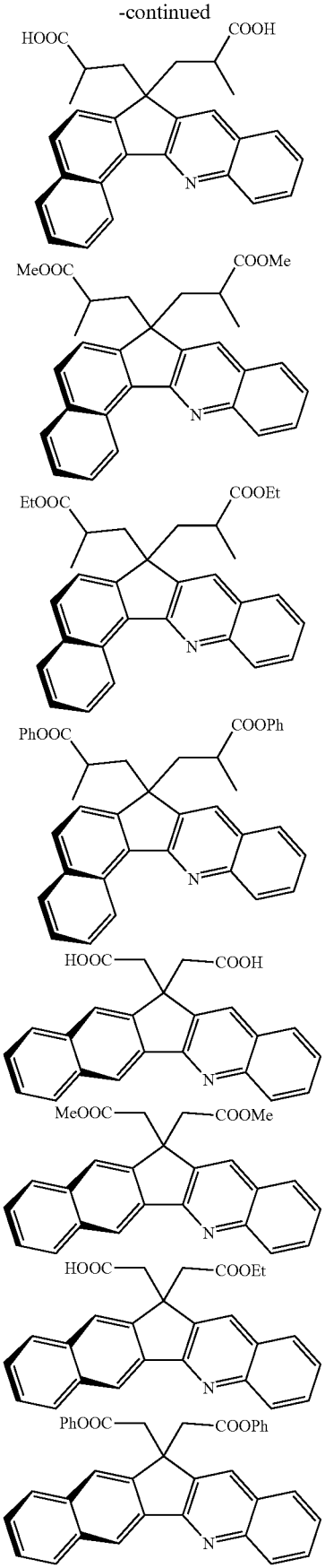
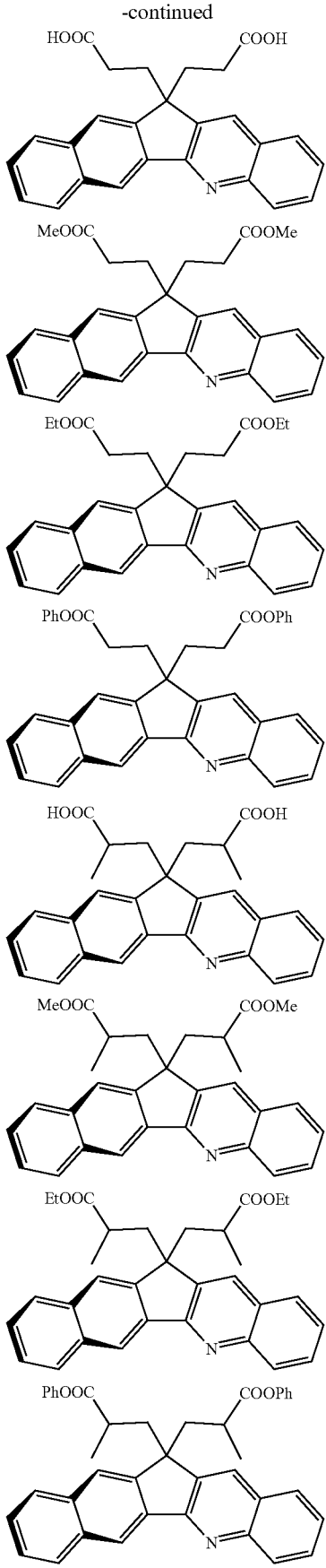

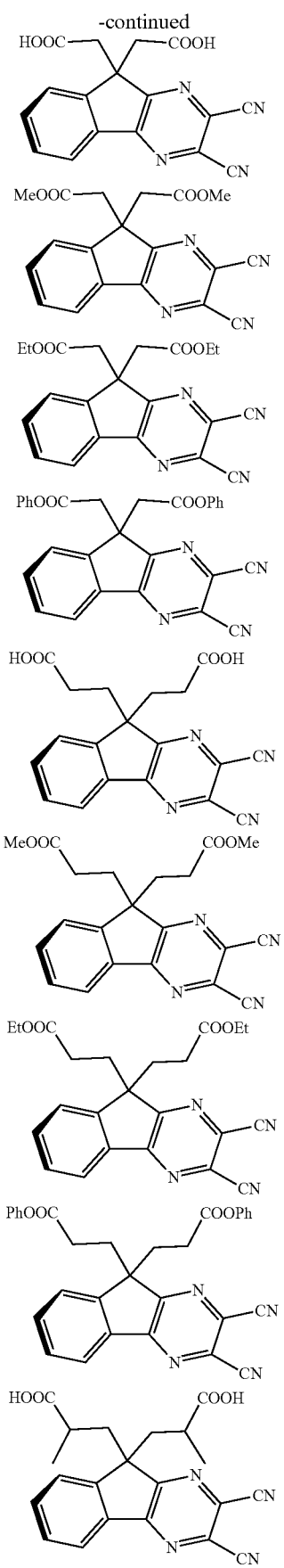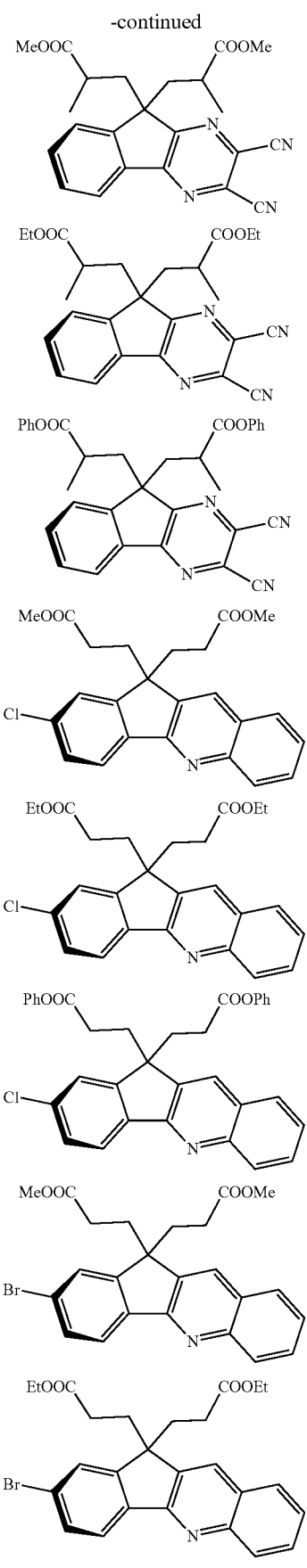

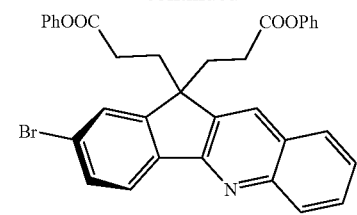
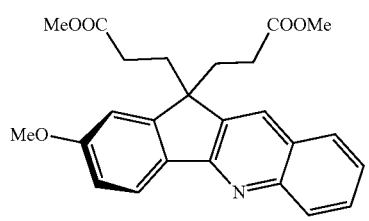
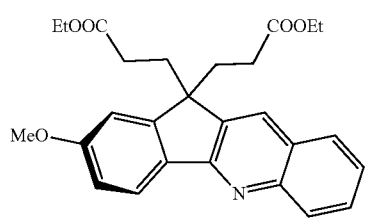
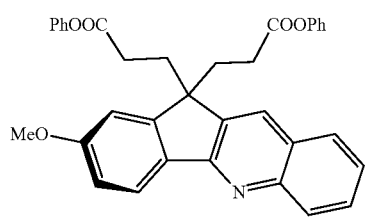
Specific preferred examples of the azafluorene diaryl ester monomer are shown below as group [O].
[Formula 43]
[O]
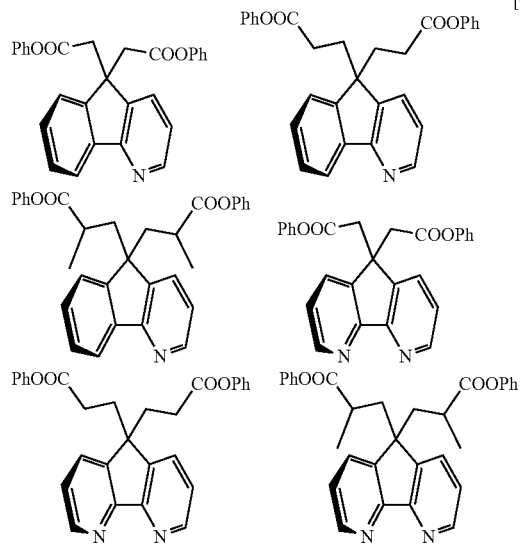
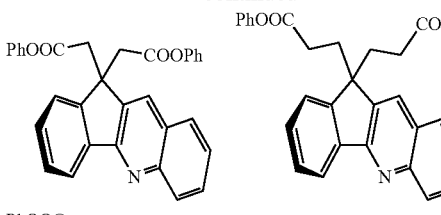
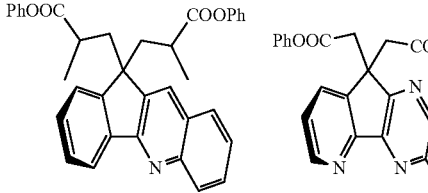
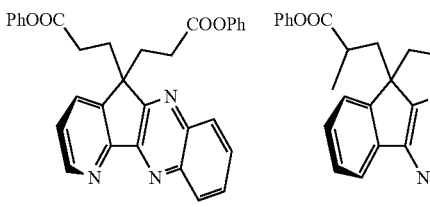
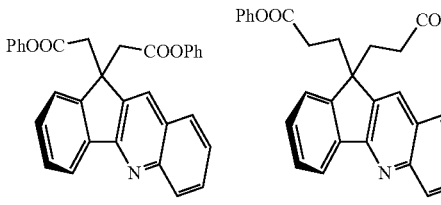
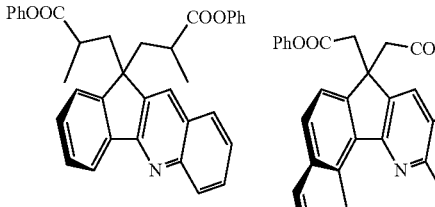
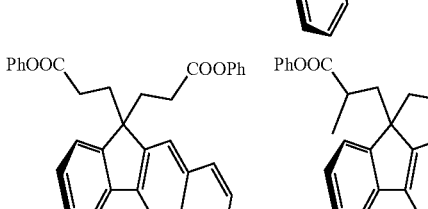
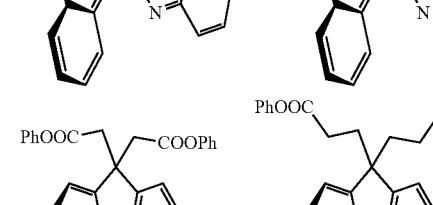
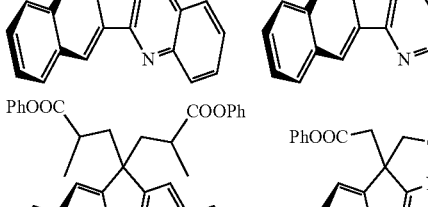

-continued

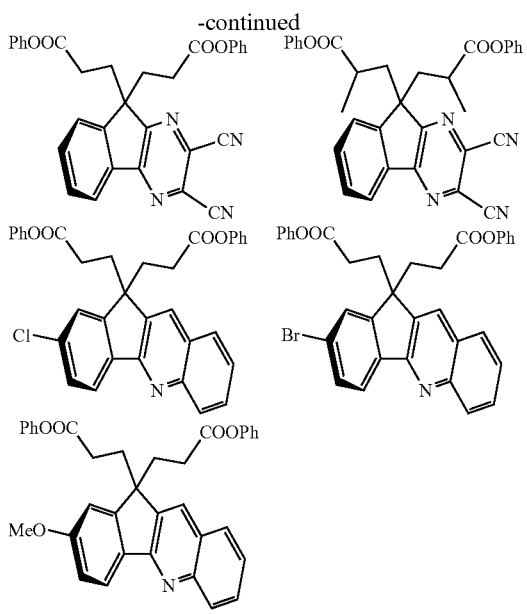

The resin according to the present disclosure can develop desired optical properties by adjusting the content of the structural unit (a) in the resin to fall within a specific range. The content of the structural unit (a) in the resin is preferably 1 wt % or more and 70 wt % or less relative to the total weight of the resin. Examples of a method for adjusting the content of the structural unit (a) in the resin include a method in which a monomer having the structural unit (a) is copolymerized with another monomer and a method in which a resin containing the structural unit (a) is blended with another resin. From the viewpoint that the content of the structural unit (a) can precisely be controlled, high transparency can be achieved, and the entire surface of a resulting film can have uniform properties, a method in which a monomer having the structural unit (a) is copolymerized with another monomer is preferred.

In order to achieve a positive refractive index anisotropy that will be described later and a sufficient reverse wavelength dispersion property, the content of the structural unit (a) is preferably 40 wt % or less, more preferably 25 wt % or less, particularly preferably 20 wt % or less. In this case, photoelastic coefficient and its stability are excellent, and a sufficiently high birefringence can be achieved by stretching. Further, in this case, since the occupancy of the structural unit (a) in the resin is low, flexibility in molecular design increases, and the resin can easily be modified if necessary. The content of the structural unit (a) is preferably 5 wt % or more, more preferably 10 wt % or more. In this case, optical properties do not sensitively change depending on slight variations in the content of the structural unit (a), and therefore the resin can easily be produced so that its various properties fall within their respective certain ranges.

Further, the structural unit (a) has a high refractive index, and therefore the resin using the structural unit (a) is suitable for use in high-refractive index lenses. In this case, from the viewpoint of imparting not only high refractive index but also proper heat resistance and flowability to the resin, the content of the structural unit (a) in the resin is preferably 65 wt % or less, more preferably 60 wt % or less. Further, in this case, the content of the structural unit (a) in the resin is preferably 20 wt % or more, more preferably 30 wt % or more.

The resin according to the present disclosure is preferably obtained by copolymerizing a monomer as a raw material of the structural unit (a) and another monomer. Examples of the another monomer to be copolymerized include dihydroxy compounds and diester compounds. In order to develop a desired reverse wavelength dispersion property, a structural unit having a positive birefringence as well as the structural unit (a) having a negative birefringence is preferably incorporated into a polymer structure. Therefore, the another monomer to be copolymerized is preferably a dihydroxy compound or diester compound as a raw material of a structural unit having a positive birefringence.

Examples of the copolymerizable monomer include a compound that can introduce a structural unit containing an aromatic ring and a compound that does not introduce a structural unit containing an aromatic ring, that is, a compound having an aliphatic structure. Specific examples of the compound having an aliphatic structure include: dihydroxy compounds of linear aliphatic hydrocarbons, such as ethylene glycol, 1,3-propanediol, 1,2-propanediol, 1,4-butanediol, 1,3-butanediol, 1,2-butanediol, 1,5-heptanediol, 1,6-hexanediol, 1,9-nonanediol, 1,10-decanediol, and 1,12-dodecanediol; dihydroxy compounds of branched aliphatic hydrocarbons, such as neopentyl glycol and hexylene glycol; dihydroxy compounds that are secondary alcohols and tertiary alcohols of alicyclic hydrocarbons, exemplified by 1,2-cyclohexanediol, 1,4-cyclohexanediol, 1,3-adamantanediol, hydrogenated bisphenol A, and 2,2,4,4-tetramethyl-1,3-cyclobutanediol; dihydroxy compounds that are primary alcohols of alicyclic hydrocarbons, such as 1,2-cyclohexane dimethanol, 1,3-cyclohexane dimethanol, 1,4-cyclohexane dimethanol, tricyclodecanedimethanol, pentacyclopentadecane dimethanol, 2,6-decalin dimethanol, 1,5-decalin dimethanol, 2,3-decalin dimethanol, 2,3-norbornane dimethanol, 2,5-norbornane dimethanol, 1,3-adamantane dimethanol, and limonene; oxyalkylene glycols such as diethylene glycol, triethylene glycol, tetraethylene glycol, polyethylene glycol, and polypropylene glycol; dihydroxy compounds having a cyclic ether structure, such as isosorbide; dihydroxy compounds having a cyclic acetal structure, such as spiroglycol and dioxane glycol; alicyclic dicarboxylic acids such as 1,2-cyclohexanedicarboxylic acid, 1,3-cyclohexanedicarboxylic acid, and 1,4-cyclohexanedicarboxylic acid; and aliphatic dicarboxylic acids such as malonic acid, succinic acid, glutaric acid, adipic acid, pimelic acid, suberic acid, azelaic acid, and sebacic acid. It is to be noted that examples of the primary alcohols of alicyclic hydrocarbons include dihydroxy compounds derived from terpene compounds.

Specific examples of the compound that can introduce a structural unit containing an aromatic ring include: aromatic bisphenol compounds such as 2,2-bis(4-hydroxyphenyl)propane, 2,2-bis(3-methyl-4-hydroxyphenyl)propane, 2,2-bis(4-hydroxy-3,5-dimethylphenyl)propane, 2,2-bis (4-hydroxy-3,5-diethylphenyl)propane, 2,2-bis(4-hydroxy-(3-phenyl)phenyl)propane, 2,2-bis(4-hydroxy-3,5-diphenyl) phenyl)propane, 2,2-bis(4-hydroxy-3,5-dibromophenyl) propane, bis(4-hydroxyphenyl)methane, 1,1-bis(4-hydroxyphenyl)ethane, 2,2-bis(4-hydroxyphenyl)butane, 2,2-bis(4-hydroxyphenyl)pentane, 1,1-bis(4-hydroxyphenyl)-1-phenylethane, bis(4-hydroxyphenyl)diphenylmethane, 1,1-bis(4-hydroxyphenyl)-2-ethylhexane, 1,1-bis(4-hydroxyphenyl)decane, bis(4-hydroxy-3-nitrophenyl) methane, 3,3-bis(4-hydroxyphenyl)pentane, 1,3-bis(2-(4-hydroxyphenyl)-2-propyl)benzene, 1,3-bis(2-(4-hydroxyphenyl)-2-propyl)benzene, 2,2-bis(4-hydroxyphenyl) hexafluoropropane, 1,1-bis(4-hydroxyphenyl)cyclohexane, bis(4-hydroxyphenyl)sulfone, 2,4'-dihydroxydiphenylsulfone, bis(4-hydroxyphenyl)sulfide, bis(4-hydroxy-3-methylphenyl)sulfide, bis(4-hydroxyphenyl)disulfide, 4,4'-dihydroxydiphenyl ether, and 4,4'-dihydroxy-3,3'-dichlorodiphenyl ether; dihydroxy compounds having an ether group bound to an aromatic group, such as 2,2-bis(4-(2-hydroxyethoxy)phenyl)propane, 2,2-bis(4-2-hydroxypropoxy)phenyl)propane, 1,3-bis(2-hydroxyethoxy)benzene, 4,4'-bis(2-hydroxyethoxy)biphenyl, and bis(4-(2-hydroxyethoxy)phenyl)sulfone; and aromatic dicarboxylic acids such as terephthalic acid, phthalic acid, isophthalic acid, 4,4'-diphenyldicarboxylic acid, 4,4'-diphenyletherdicarboxylic acid, 4,4'-benzophenonedicarboxylic acid, 4,4'-diphenoxyethanedicarboxylic acid, 4,4'-diphenylsulfonedicarboxylic acid, and 2,6-naphthalenedicarboxylic acid.

It is to be noted that the aliphatic dicarboxylic acid and aromatic dicarboxylic acid components may be used as a dicarboxylic acid itself for a raw material of the polyester carbonate, but depending on a production method, a dicarboxylic acid ester such as a methyl ester or a phenyl ester or a dicarboxylic acid derivative such as a dicarboxylic acid halide may also be used as a raw material.

As the copolymerizable monomer, a dihydroxy compound having a fluorene ring conventionally known as a compound having a structural unit having a negative birefringence, such as 9,9-bis(4-(2-hydroxyethoxy)phenyl)fluorene, 9,9-bis(4-hydroxyphenyl)fluorene, or 9,9-bis(4-hydroxy-3-methylphenyl)fluorene or a dicarboxylic acid compound having a fluorene ring may also be used in combination with a monomer having the structural unit (a).

From the viewpoint of optical properties, the resin according to the present disclosure preferably contains, as a structural unit other than the structural unit (a), a structural unit containing no aromatic component. That is, a compound having an aliphatic structure is preferably used as the copolymerizable monomer. Among compounds having an aliphatic structure, compounds having an alicyclic structure are more preferred from the viewpoint of excellent mechanical properties and heat resistance. When the main chain of the polymer contains an aromatic component, as described above, the reverse wavelength dispersion property of the azafluorene ring is cancelled out, and therefore the content of the structural unit (a) needs to be increased, which leads to a fear that photoelastic coefficient and mechanical properties deteriorate. The use of a structural unit containing no aromatic component as a structural unit other than the structural unit (a) makes it possible to prevent the incorporation of an aromatic component into the main chain.

On the other hand, incorporation of an aromatic component into the main chain or side chain of the polymer is sometimes effective at keeping optical properties and balancing optical properties with heat resistance, mechanical properties, etc. From the viewpoint of keeping a balance among various properties, the content of a structural unit containing an aromatic group (except for the structural unit (a)) in the resin is preferably 5 wt % or less.

From the viewpoint of optical properties, mechanical properties, and heat resistance, among structural units that can be introduced by the above-mentioned compounds having an alicyclic structure, the resin according to the present disclosure particularly preferably contains, as a copolymerization component, at least one of a structural unit represented by the following formula (10) and a structural unit represented by the following formula (11). It is to be noted that the structure represented by the formula (10) or the structure represented by the formula (11) is sometimes referred to as a "structural unit (b)".

[Formula 44]

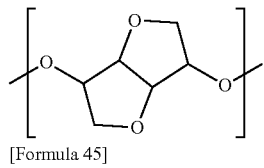

(10)

[Formula 45]

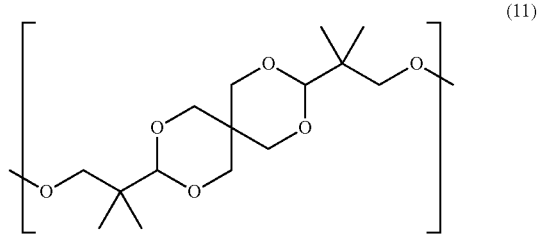

(11)

Examples of a dihydroxy compound that can introduce the structural unit represented by the formula (10) include isosorbide (ISB), isomannide, and isoidide that are in a stereoisomeric relationship. They may be used singly or in combination of two or more of them. Among them, from the viewpoint of availability and polymerization reactivity, ISB is preferably used.

As a dihydroxy compound that can introduce the structural unit represented by the formula (11), spiro glycol may be used.

The resin according to the present disclosure may contain either one or both of the structural unit represented by the formula (10) and the structural unit represented by the formula (11). The amount of the structural unit (b) contained in the resin according to the present disclosure is preferably 10 wt % or more and 90 wt % or less. The amount of the structural unit (b) contained in the resin is more preferably 85 wt % or less, even more preferably 80 wt % or less. The amount of the structural unit (b) contained in the resin is more preferably 50 wt % or more, even more preferably 60 wt % or more, particularly preferably 70 wt % or more. When the amount of the structural unit (b) contained in the resin is equal to or more than the above lower limit, sufficient mechanical properties and flowability and low photoelastic coefficient are achieved. On the other hand, when the amount of the structural unit (b) contained in the resin is equal to or less than the above upper limit, sufficient reverse wavelength dispersion property is developed by the structural unit (a).

The resin according to the present disclosure may further contain another structural unit other than the structural unit (a) and the structural unit (b). It is to be noted that such a structural unit is sometimes referred to as a "structural unit (c)". The resin contains at least the structural unit (a) and may further contain at least one of the structural unit (b) and the structural unit (c).

As a monomer having the structural unit (c) (i.e., a monomer that can introduce the structural unit (c) into the resin), 1,4-cyclohexane dimethanol, tricyclodecane dimethanol, 1,4-cyclohexanedicarboxylic acid, or a derivative thereof is preferably used, and 1,4-cyclohexane dimethanol or tricyclodecane dimethanol is more preferably used. The resin containing a structural unit derived from such a monomer has an excellent balance between optical properties and heat resistance, mechanical properties, etc. Diester compounds are relatively low in polymerization reactivity, and therefore from the viewpoint of increasing reaction efficiency, it is preferred that a diester compound other than a diester compound containing the structural unit (a) is not used.

The dihydroxy compounds and the diester compounds for introducing the structural unit (c) are used singly or in combination of two or more of them depending on performance required of a resulting resin. The amount of the structural unit (c) contained in the resin is preferably 1 wt % or more and 50 wt % or less, more preferably 5 wt % or more and 40 wt % or less, even more preferably 10 wt % or more and 30 wt % or less. The structural unit (c) particularly plays the role of adjusting the heat resistance of the resin or imparting flexibility or toughness to the resin. Therefore, if the amount of the structural unit (c) contained in the resin is too small, there is a fear that the mechanical properties and melt processability of the resin are reduced. On the other hand, if the amount of the structural unit (c) contained in the resin is too large, there is a fear that heat resistance and optical properties are reduced. That is, the mechanical properties, melt processability, heat resistance, and optical properties of the resin are improved by adjusting the amount of the structural unit (c) contained in the resin is adjusted to fall within the above range.

[Method for Producing Resin According to Present Disclosure]

A polycarbonate, polyester, or polyester carbonate suitably used as the resin according to the present disclosure is produced by, for example, a polymerization method generally used. That is, the resin can be produced by, for example, solution polymerization or interfacial polymerization using phosgene or a carboxylic acid halide or melt polymerization in which reaction is performed without using a solvent. Among these production methods, from the viewpoint that the resin can be produced without using a solvent or a highly-toxic compound, burdens on the environment can be reduced, and productivity is excellent, the resin is preferably produced by melt polymerization.

When a solvent is used for polymerization, there is a fear that the glass transition temperature of the resin reduces due to plasticizing effect of the solvent remaining in the resin. Therefore, it is difficult to control molecular orientation to be constant in a stretching process described later. Further, when a halogen-based organic solvent such as methylene chloride remains in the resin, the resin causes corrosion, and therefore, for example, when a molded body of the resin is incorporated into an electronic device or the like, corrosion may occur. The resin obtained by melt polymerization contains no solvent, and is therefore advantageous for a processing process or stabilization of product quality.

When the resin is produced by melt polymerization, for example, a monomer having the structural unit (a), another copolymerizable monomer such as a diol or a diester, and a polymerization catalyst are mixed and subjected to an interesterification reaction in a melt state, and the rate of reaction is increased by removing a desorbed component to the outside of the system. In the end of polymerization, the reaction is allowed to proceed under high temperature and high vacuum conditions until a desired molecular weight is achieved. When the reaction is completed, the resin in a melt state is extracted from a reactor. The thus obtained resin is used as, for example, a raw material of a molded article such as a retardation film.

In the present disclosure, the polycarbonate or polyester carbonate is obtained by poly condensation using a monomer containing at least the structural unit (a), at least one dihydroxy compound, and a diester carbonate as raw materials.

Examples of the diester carbonate usually used in the polycondensation reaction include the above-mentioned diester carbonates represented by the general formula (6). These diester carbonates may be used singly or in combination of two or more of them.

[Formula 46]

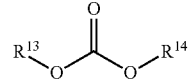

(6)

In the formula (6), $R^{13}$ and $R^{14}$ are each an optionally substituted aryl group having 6 to 11 carbon atoms, an optionally substituted heteroaryl group having 3 to 10 carbon atoms, or an optionally substituted alkyl group having 1 to 10 carbon atoms. $R^{13}$ and $R^{14}$ may be the same or different from each other. $R^{13}$ and $R^{14}$ are preferably optionally-substituted aryl groups, more preferably unsubstituted aryl groups. It is to be noted that examples of a substituent include an alkyl group, an ester group, an ether group, a carboxylic acid, an amide group, and a halogen.

Examples of the diester carbonate represented by the formula (6) include diphenyl carbonate (i.e., DPC) and a substituted diphenyl carbonate such as ditolyl carbonate. Other examples of the diester carbonate include dimethyl carbonate, diethyl carbonate, and di-tert-butyl carbonate. The diester carbonate is preferably diphenyl carbonate or a substituted diphenyl carbonate, more preferably diphenyl carbonate. It is to be noted that the diester carbonate sometimes contains impurities such as chloride ions. Such impurities may inhibit the polymerization reaction or impair the hue of the polycarbonate, and therefore it is preferred that if necessary, the diester carbonate is purified by distillation or the like before use.

In the poly condensation reaction, the mole ratio between all the dihydroxy compounds and all the diester compound used for the reaction is strictly adjusted, which makes it possible to control the reaction speed and the molecular weight of a resulting resin. In the case of a polycarbonate, the mole ratio of the diester carbonate too all the dihydroxy compounds is preferably adjusted to 0.90 to 1.10, more preferably adjusted to 0.95 to 1.07, and particularly preferably adjusted to 0.98 to 1.05. In the case of a polyester, the mole ratio of all the diester compounds to all the dihydroxy compounds is preferably adjusted to 0.70 to 1.10, more preferably adjusted to 0.80 to 1.05, and particularly preferably adjusted to 0.85 to 1.00. In the case of a polyester carbonate, the mole ratio of the total amount of the diester carbonate and all the diester compounds to all the dihydroxy compounds is preferably adjusted to 0.90 to 1.10, more preferably adjusted to 0.95 to 1.05, and particularly preferably adjusted to 0.97 to 1.02.

If the mole ratio greatly deviates from the above range, there is a fear that a resin having a desired molecular weight cannot be produced. If the mole ratio is too small, there is a case where the number of terminal hydroxyl groups of the produced resin increases so that the heat stability of the resin reduces. If the mole ratio is too large, there is a fear that the speed of the interesterification reaction reduces under the same conditions or the amount of the diester carbonate or the diester compound remaining in the produced resin increases.

The remaining low molecular component may volatilize during film formation from the resin or stretching of the resin so that a resulting film may have a defect.

The melt polymerization is usually performed by a multistage process including two or more stages. The polycondensation reaction may be performed by a process including two or more stages by using one polymerization reactor and sequentially changing conditions, or may be performed by a process including two or more stages by using two or more reactors and changing their respective conditions. However, from the viewpoint of production efficiency, the polycondensation reaction is usually performed using two or more reactors, preferably three or more reactors. The polycondensation reaction may be performed in any one of batch mode, continuous mode, and a combination of batch mode and continuous mode, but from the viewpoint of production efficiency and quality stability, continuous mode is preferred.

In the poly condensation reaction, it is preferred that a balance between temperature and pressure in the reaction system is properly controlled. If either one of the temperature and the pressure is changed too early, there is a fear that unreacted monomers are distilled out of the reaction system. As a result, there is a case where a resin having a desired molecular weight cannot be obtained due to a change in the mole ratio between the dihydroxy compound and the diester compound.

The polymerization speed of the polycondensation reaction is controlled by the balance between a terminal hydroxyl group and a terminal ester group or a terminal carbonate group. Particularly, in the case of performing polymerization in continuous mode, when the balance between terminal groups fluctuates due to distillation out of unreacted monomers, there is a fear that it is difficult to control the polymerization speed to be constant so that the molecular weight of a resulting resin greatly fluctuates. The molecular weight of the resin correlates with melt viscosity. Therefore, when film is formed from the obtained resin by melt film formation, there is a fear that it is difficult to keep the quality of the film, such as film thickness, constant due to fluctuation of melt viscosity so that the quality or productivity of the film reduces.

Further, if unreacted monomers are distilled out, there is a fear that not only fluctuation of the balance between terminal groups but also deviation of the copolymerization composition of the resin from a desired composition occurs, which affects also the optical quality of a retardation film. The later-described wavelength dispersion property of retardation of a retardation film according to the present disclosure is controlled by the ratio between the structural unit (a) and the copolymerization component in the resin. Therefore, when the ratio is changed during polymerization, there is a fear that optical properties cannot be obtained as designed, or, in the case of obtaining a long film, a polarizing plate having constant quality cannot be produced due to a change in optical properties depending on the position of the film.

More specifically, the following conditions may be employed as reaction conditions in the first-stage reaction. The maximum inner temperature of the polymerization reactor is usually set to 150° C. or more, preferably 170° C. or more, more preferably 190° C. or more. The maximum inner temperature of the polymerization reactor is usually set to 250° C. or less, preferably 240° C. or less, more preferably 230° C. or less. The pressure in the polymerization reactor is usually set to 70 kPa or less, preferably 50 kPa or less, more preferably 30 kPa or less. The pressure in the polymerization reactor is usually set to 1 kPa or more, preferably 3 kPa or more, more preferably 5 kPa or more. It is to be noted that the pressure is an absolute pressure. The reaction time is usually set to 0.1 hours or more, preferably 0.5 hours or more. The reaction time is usually set to 10 hours or less, preferably 5 hours or less, more preferably 3 hours or less. The first-stage reaction is performed while a generated monohydroxy compound derived from the diester compound is distilled out of the reaction system. For example, when diphenyl carbonate is used as the diester carbonate, phenol is distilled out of the reaction system as the monohydroxy compound in the first-stage reaction.

In the first-stage reaction, the polymerization reaction can be promoted by reducing the reaction pressure as low as possible. However, if the pressure is excessively reduced, the amount of unreacted monomers distilled out increases. In order to achieve both prevention of distillation out of unreacted monomers and promotion of the reaction by pressure reduction, it is effective to use a reactor equipped with a reflux condenser. Particularly, it is better to use the reflux condenser in the initial stage of the reaction in which the amount of unreacted monomers is large.

In and after the second-stage reaction, the pressure in the reaction system is gradually reduced from the pressure in the first stage, and is finally reduced to 5 kPa or less, preferably 3 kPa or less, more preferably 1 kPa or less while the generated monohydroxy compound is continued to be distilled out of the reaction system. The maximum inner temperature is usually set to 210° C. or more, preferably 220° C. or more. The maximum inner temperature is usually set to 260° C. or less, preferably 250° C. or less, particularly preferably 240° C. or less. The reaction time is usually set to 0.1 hours or more, preferably 0.5 hours or more, more preferably 1 hour or more. The reaction time is usually set to 10 hours or less, preferably 5 hours or less, more preferably 3 hours or less. In order to prevent coloring or heat deterioration to obtain a resin excellent in hue or heat stability, the maximum inner temperature in all the reaction stages is usually 260° C. or less, preferably 250° C. or less, more preferably 240° C. or less.

The interesterification reaction catalyst usable in the polymerization (hereinafter, the "interesterification reaction catalyst" is sometimes referred to as a "catalyst" or a "polymerization catalyst") may have a very large effect on the reaction speed or the hue or heat stability of a resin obtained by polycondensation. The catalyst to be used is not particularly limited as long as the produced resin can satisfy transparency, hue, heat resistance, heat stability, and mechanical strength requirements. Examples of such a catalyst include compounds of metals belonging to Group 1 or Group 2 in the long-form periodic table (hereinafter, Group 1 in the long-form periodic table is referred to as "Group 1" and Group 2 in the long-form periodic table is referred to as "Group 2") and basic compounds such as basic boron compounds, basic phosphorus compounds, basic ammonium compounds, and amine-based compounds. Preferably, a compound of at least one metal selected from the group consisting of metals belonging to Group 2 in the long-form periodic table and lithium is used.

As the Group 1 metal compound, for example, the following compounds may be used, but a Group 1 metal compound other than them may also be used: sodium hydroxide, potassium hydroxide, lithium hydroxide, cesium hydroxide, sodium hydrogen carbonate, potassium hydrogen carbonate, lithium hydrogen carbonate, cesium hydrogen carbonate, sodium carbonate, potassium carbonate, lithium carbonate, cesium carbonate, sodium acetate, potassium acetate, lithium acetate, cesium acetate, sodium stearate, potassium stearate, lithium stearate, cesium stearate, sodium boron hydride, potassium boron hydride, lithium boron hydride, cesium boron hydride, sodium tetraphenyl borate, potassium tetraphenyl borate, lithium tetraphenyl borate, cesium tetraphenyl borate, sodium benzoate, potassium benzoate, lithium benzoate, cesium benzoate, disodium hydrogen phosphate, dipotassium hydrogen phosphate, dilithium hydrogen phosphate, dicesium hydrogen phosphate, disodium phenyl phosphate, dipotassium phenyl phosphate, dilithium phenyl phosphate, dicesium phenyl phosphate, alcoholates and phenolates of sodium, potassium, lithium, and cesium, and disodium salt, dipotassium salt, dilithium salt, and dicesium salt of bisphenol A. Among them, from the viewpoint of polymerization activity and the hue of a resulting polycarbonate, a lithium compound is preferably used.

As the Group 2 metal compound, for example, the following compounds may be used, but a Group 2 metal compound other than them may also be used: potassium hydroxide, barium hydroxide, magnesium hydroxide, strontium hydroxide, calcium hydrogen carbonate, barium hydrogen carbonate, magnesium hydrogen carbonate, strontium hydrogen carbonate, calcium carbonate, barium carbonate, magnesium carbonate, strontium carbonate, calcium acetate, barium acetate, magnesium acetate, strontium acetate, calcium stearate, barium stearate, magnesium stearate, and strontium stearate. Among them, a magnesium compound, a calcium compound, and a barium compound are preferably used. From the viewpoint of polymerization activity and the hue of a resulting polycarbonate, a magnesium compound and/or a calcium compound are more preferably used, and a calcium compound is particularly preferably used.

It is to be noted that a basic compound such as a basic boron compound, a basic phosphorus compound, a basic ammonium compound, or an amine-based compound may also supplementarily be used in combination with the Group 1 metal compound and/or the Group 2 metal compound, but it is particularly preferred that a compound of at least one metal selected from the group consisting of metals belonging to Group 2 in the long-form periodic table and lithium is used.

As the basic phosphorus compound, for examples, the following compounds may be used, but a basic phosphorus compound other than them may also be used: triethylphosphine, tri-n-propylphosphine, triisopropylphosphine, tri-n-butylphosphine, triphenylphosphine, tributylphosphine, and quaternary phosphonium salts.

As the basic ammonium compound, for examples, the following compounds may be used, but a basic ammonium compound other than them may also be used: tetramethylammonium hydroxide, tetraethylammonium hydroxide, tetrapropylammonium hydroxide, tetrabutylammonium hydroxide, N,N,N-trimethylethanolamine (choline), trimethylethylammonium hydroxide, trimethylbenzylammonium hydroxide, trimethylphenylammonium hydroxide, triethylmethylammonium hydroxide, triethylbenzylammonium hydroxide, triethylphenylammonium hydroxide, tribuylbenzylammonium hydroxide, tributylphenylammonium hydroxide, tetraphenylammonium hydroxide, benzyltriphenylammonium hydroxide, methyltriphenylammonium hydroxide, and butyltriphenylammonium hydroxide.

As the amine-based compound, for example, the following compounds may be used, but an amine-based compound other than them may also be used: 4-aminopyridine, 2-aminopyridine, N,N-dimethyl-4-aminopyridine, 4-diethylaminopyridine, 2-hydroxypyridine, 2-methoxypyridine, 4-methoxypyridine, 2-dimethylaminoimidazole, 2-methoxyimidazole, imidazole, 2-mercaptoimidazole, 2-methylimidazole, aminoquinoline, and guanidine.

The amount of the polymerization catalyst used is usually 0.1 µmol to 300 µmol, preferably 0.5 µmol to 100 µmol, more preferably 1 µmol to 50 µmol per 1 mol of all the dihydroxy compounds used for polymerization. When a compound of at least one metal selected from the group consisting of metals belonging to Group 2 in the long-form periodic table and lithium is used as the polymerization catalyst, particularly when a magnesium compound and/or a calcium compound are/is used as the polymerization catalyst, the amount of the polymerization catalyst used is usually 0.1 µmol or more, preferably 0.3 µmol or more, more preferably 0.5 µmol or more in terms of the amount of metal per 1 mol of all the dihydroxy compounds. The amount of the polymerization catalyst used is usually 30 µmol or less, preferably 20 µmol or less, more preferably 10 µmol or less.

When a polyester or a polyester carbonate is produced using a diester compound as a monomer, an interesterification catalyst such as a titanium compound, a tin compound, a germanium compound, an antimony compound, a zirconium compound, a lead compound, an osmium compound, a zinc compound, or a manganese compound may also be used in combination or not in combination with the basic compound. The amount of the interesterification catalyst used is usually in the range of 1 µmol to 1 mmol, preferably in the range of 5 µmol to 800 µmol, more preferably in the range of 10 µmol to 500 µmol in terms of the amount of metal per 1 mol of all the dihydroxy compounds used in the reaction.

If the amount of the catalyst is too small, the polymerization speed reduces, which results in that the polymerization temperature needs to be increased to compensate for the reduction in polymerization speed in order to obtain a resin having a desired molecular weight. As a result, the hue of a resulting resin is likely to deteriorate, or there is a possibility that unreacted raw materials volatilize during polymerization so that a resulting resin cannot have a desired molecular weight due to a change in the mole ratio between the dihydroxy compound and the diester compound. On the other hand, if the amount of the polymerization catalyst used is too large, there is a possibility that an undesirable side reaction occurs, which deteriorates the hue of a resulting resin or causes coloring of the resin during molding processing.

Among Group 1 metals, sodium, potassium, and cesium may have an adverse effect on hue when the resin contains them in a large amount. These metals sometimes enter the resin not only from the catalyst used but also from the raw material or the reaction apparatus. Irrespective of the source, the total amount of compounds of these metals in the resin is usually 2 µmol or less, preferably 1 µmol or less, more preferably 0.5 µmol or less in terms of the amount of metal per 1 mol of all the dihydroxy compounds.

The resin according to the present disclosure may usually be solidified by cooling and pelletized by a rotary cutter or the like after polymerized as described above. A pelletization method is not particularly limited, and examples thereof includes: a method in which the resin is extracted in a melt state from the polymerization reactor of the final stage, solidified by cooling in the form of a strand, and pelletized; a method in which the resin is supplied in a melt state from the polymerization reactor of the final stage to a single- or twin-screw extruder, melt-extruded, then solidified by cooling, and pelletized; and a method in which the resin is extracted in a melt state from the polymerization reactor of the final stage, solidified by cooling in the form of a strand, and once pelletized, and then the resin is again supplied to a single- or twin-screw extruder, melt-extruded, then solidified by cooling, and pelletized.

The molecular weight of the thus obtained resin can be expressed by reduced viscosity. If the reduced viscosity of the resin is too low, there is a possibility that the mechanical strength of a molded article is low. Therefore, the reduced viscosity is usually 0.20 dL/g or more, preferably 0.30 dL/g or more. On the other hand, if the reduced viscosity of the resin is too large, productivity or moldability tends to reduce due to a reduction in flowability during molding. Therefore, the reduced viscosity is usually 1.20 dL/g or less, preferably 1.00 dL/g or less, more preferably 0.80 dL/g or less, particularly preferably 0.60 dL/g or less. It is to be noted that the reduced viscosity is measured using an Ubbelohde viscometer at a temperature of 20.0° C.±0.1° C. by precisely adjusting the concentration of a polycarbonate to 0.6 g/dL using methylene chloride as a solvent.

When the composition of the resin is the same, the reduced viscosity correlates with the melt viscosity of the resin. Therefore, the stirring power of a polymerization reactor, the discharge pressure of a gear pump for transferring the melt resin, or the like can usually be used as an indicator for operation control. That is, when the reading of such an operating device reaches a target value, the polymerization reaction is terminated by returning the pressure in the reactor to ordinary pressure or extracting the resin from the reactor.

The melt viscosity of the resin according to the present disclosure is preferably 700 Pa·s or more and 5000 Pa·s or less under measurement conditions of a temperature of 240° C. and a shear rate of 91.2 sec$^{-1}$. The melt viscosity of the resin is more preferably 4000 Pa·s or less, even more preferably 3000 Pa·s or less, particularly preferably 2700 Pa·s or less. The melt viscosity of the resin is more preferably 1000 Pa·s or more, even more preferably 1500 Pa·s or more, particularly preferably 2000 Pa·s or more. It is to be noted that the melt viscosity is measured using, for example, a capillary rheometer (manufactured by Toyo Seiki Seisakusho, Ltd.).

The glass transition temperature of the resin according to the present disclosure is preferably 110° C. or more and 160° C. or less. The glass transition temperature is more preferably 155° C. or less, even more preferably 150° C. or less, particularly preferably 145° C. or less. The glass transition temperature is more preferably 120° C. or more, even more preferably 130° C. or more. When the glass transition temperature is equal to or more than the above lower limit, the resin tends to have excellent heat resistance, and therefore, for example, it is possible to prevent the dimensional change of a film after molding or impairment of quality under use conditions of a retardation film. On the other hand, when the glass transition temperature is equal to or less than the above upper limit, a film is prevented from having variations in thickness or becoming brittle during molding, and therefore has improved stretchability. Further, the film has excellent transparency.

When a diester compound is used for the polycondensation reaction, there is a fear that a monohydroxy compound generated as a by-product remains in the resin and volatilizes during film formation or stretching to cause an odor, which deteriorates a working environment and contaminates a transfer roll to impair the appearance of a film. Particularly, when diphenyl carbonate (DPC) that is a useful diester carbonate is used, phenol generated as a by-product has a relatively high boiling point, and is therefore likely to remain in the resin without being sufficiently removed by the reaction under reduced pressure. Therefore, the amount of a diester carbonate-derived monohydroxy compound contained in the resin according to the present disclosure is preferably 1500 ppm by weight or less, more preferably 1000 ppm by weight or less, even more preferably 700 ppm by weight or less. In order to solve the above problem, the content of the monohydroxy compound is preferably as small as possible, but it is difficult for a melt polymerization method to reduce the amount of the monohydroxy compound remaining in the polymer to zero, and an enormous effort is required to remove it. Usually, the above problem can sufficiently be prevented by reducing the content of the monohydroxy compound to 1 ppm by weight.

In order to reduce low molecular components remaining in the resin according to the present disclosure, including the diester carbonate-derived monohydroxy compound, it is effective to perform degassing of the resin in an extruder as described above or to reduce the pressure in the latter stage of polymerization to 3 kPa or less, preferably 2 kPa or less, more preferably 1 kPa or less.

If the reaction pressure is excessively reduced when the pressure in the latter stage of polymerization is reduced, there is a case where it is difficult to control the reaction due to a rapid increase in molecular weight, and therefore it is preferred that the resin is produced by controlling the concentration of a terminal hydroxyl group or terminal ester group thereof to be excessive to bias the terminal group balance. When a polyester carbonate is synthesized using a diester compound as a monomer having the structural unit (a), the diester monomer having the structural unit (a) is relatively low in reactivity, and is therefore likely to remain without being reacted. Therefore, the concentration of terminal hydroxy group of the resin is controlled to be excessive in polymerization, which makes it possible to increase the reaction rate of the diester monomer. That is, the amount of a terminal ester group in a final polymer is preferably 1 mol/ton or more and 70 mol/ton or less. The amount of a terminal ester group in the polymer is more preferably 50 mol/ton or less, particularly preferably 30 mol/ton or less. The amount of a terminal ester group in the polymer is more preferably 5 mol/ton or more, particularly preferably 10 mol/ton or more.

If necessary, the resin according to the present disclosure may contain a heat stabilizer to prevent a reduction in molecular weight or deterioration of hue during molding or the like. Examples of such a heat stabilizer include a generally-known hindered phenol-based heat stabilizer and/or a generally-known phosphorus-based heat stabilizer.

As the hindered phenol-based compound, for example, the following compounds may be used: 2,6-di-tert-butylphenol, 2,4-di-tert-butylphenol, 2-tert-butyl-4-methoxyphenol, 2-tert-butyl-4,6-dimethylphenol, 2,6-di-tert-butyl-4-methylphenol, 2,6-di-tert-butyl-4-ethylphenol, 2,5-di-tert-butylhydroquinone, n-octadecyl-3-(3',5'-di-tert-butyl-4'-hydroxyphenyl)propionate, 2-tert-butyl-6-(3'-tert-butyl-5'-methyl-2'-hydroxybenzyl)-4-methylphenylacrylate, 2,2'-methylene-bis-(4-methyl-6-tert-butylphenol), 2,2'-methylene-bis(6-cyclohexyl-4-methylphenol), 2,2'-ethylidene-bis-(2,4-di-tert-butylphenol), tetrakis-[methylene-3-(3',5'-di-tert-butyl-4'-hydroxyphenyl)propionate]-methane, and 1,3,5-trimethyl-2,4,6-tris-(3,5-di-tert-butyl-4-hydroxybenzyl) benzene. Among others are tetrakis-[methylene-3-(3',5'-di-tert-butyl-4'-hydroxyphenyl)propionate]-methane, n-octadecyl-3-(3',5'-di-tert-butyl-4'-hydroxyphenyl)propionate, and 1,3,5-trimethyl-2,4,6-tris-(3,5-di-tert-butyl-4-hydroxybenzyl)benzene.

As the phosphorus-based compound, for example, the following phosphorus acid, phosphoric acid, phosphonous acid, phosphonic acid, and esters thereof may be used, but a phosphorus-based compound other than these compounds may also be used: triphenyl phosphite, tris(nonylphenyl) phosphite, tris(2,4-di-tert-butylphenyl) phosphite, tridecyl phosphite, trioctyl phosphite, trioctadecyl phosphite, didecylmonophenyl phosphite, dioctylmonophenyl phosphite, diisopropylmonophenyl phosphite, monobutyldiphenyl phosphite, monodecyldiphenyl phosphite, monooctyldiphenyl phosphite, bis(2,6-di-tert-butyl-4-methylphenyl) pentaerythritol diphosphite, 2,2-methylenebis(4,6-di-tert-butylphenyl)octyl phosphite, bis(nonylphenyl) pentaerythritol diphosphite, bis(2,4-di-tert-butylphenyl) pentaerythritol diphosphite, distearylpentaerythritol diphosphite, tributyl phosphate, triethyl phosphate, trimethyl phosphate, triphenyl phosphate, diphenyl monoorthoxenyl phosphate, dibutyl phosphate, dioctyl phosphate, diisopropyl phosphate, tetrakis(2,4-di-tert-butylphenyl) 4,4'-biphenylene diphosphinate, dimethyl benzenephosphate, diethyl benzenephosphonate, and dipropyl benzenephosphate. These heat stabilizers may be used singly or in combination of two or more of them.

The heat stabilizer may be added to a reaction liquid during melt polymerization, or may be added to and kneaded with the resin by using an extruder. When film formation is performed by melt extrusion, a film may be formed by adding the heat stabilizer or the like to an extruder or by using pellets or the like previously formed by adding the heat stabilizer or the like to the resin using an extruder.

The amount of the heat stabilizer added is preferably 0.0001 parts by weight or more, more preferably 0.0005 parts by weight or more, even more preferably 0.001 parts by weight or more and preferably 1 part by weight or less, more preferably 0.5 parts by weight or less, even more preferably 0.2 parts by weight or less per 100 parts by weight of the resin used in the present disclosure.

If necessary, the resin according to the present disclosure may also contain a generally-known antioxidant to prevent oxidation. As such an antioxidant, for example, the following compounds may be used, but a compound other than them may also be used: pentaerythritol tetrakis(3-mercaptopropionate), pentaerythritol tetrakis(3-laurylthiopropionate), glycerol-3-stearylthiopropionate, triethylene glycol-bis[3-(3-tert-butyl-5-methyl-4-hydroxyphenyl)propionate], 1,6-hexanediol-bis[3-(3,5-di-tert-butyl-4-hydroxyphenyl) propionate], pentaerythritol-tetrakis[3-(3,5-di-tert-butyl-4-hydroxyphenyl)propionate], octadecyl-3-(3,5-di-tert-butyl-4-hydroxyphenyl)propionate, 1,3,5-trimethyl-2,4,6-tris(3,5-di-tert-butyl-4-hydroxybenzyl)benzene, N,N-hexamethylenebis(3,5-di-tert-butyl-4-hydroxy-hydrocinnamide), diethyl 3,5-di-tert-butyl-4-hydroxy-benzylphosphonate, tris(3,5-di-tert-butyl-4-hydroxybenzyl)isocyanurate, tetrakis(2,4-di-tert-butylphenyl) 4,4'-biphenylene diphosphinate, and 3,9-bis{1,1-dimethyl-2-[β-(3-tert-butyl-4-hydroxy-5-methylphenyl)propionyloxy]ethyl}-2,4,8,10-tetraoxaspiro(5,5) undecane. These antioxidants may be used singly or in combination of two or more of them. The amount of the antioxidant added is preferably 0.0001 parts by weight or more, more preferably 0.5 parts by weight or more per 100 parts by weight of the resin.

As long as the object of the present disclosure is not impaired, the resin according to the present disclosure may contain additives other than the heat stabilizer and the antioxidant, such as a UV absorber, a release agent, an antistatic agent, a slip agent, a lubricant, a plasticizer, a compatibilizer, a nucleating agent, a flame retardant, an inorganic filler, an impact improver, a foaming agent, and a dye which are generally used.

For the purpose of improving the properties of the resin according to the present disclosure, such as mechanical properties and solvent resistance, the resin may be kneaded with a synthetic resin such as an aromatic polycarbonate, an aromatic polyester, an aliphatic polyester, a polyamide, polystyrene, a polyolefin, acryl, an amorphous polyolefin, ABS, AS, polylactic acid, or polybutylene succinate; or rubber or the like to produce a polymer alloy. That is, the resin according to the present disclosure may be used as a polymer alloy. These synthetic resins and rubber may be used singly or in combination of two or more of them. Such a synthetic resin, rubber, or the like is added to the resin as, for example, a modifier.

The timing at which the additive and the modifier are mixed and kneaded with the resin is not particularly limited. For example, the additive and the modifier are added to the resin at a time or in any order. The mixing and kneading are performed using a tumbler, a V-shaped blender, a Nauta mixer, a Banbury mixer, a kneading roll, or an extruder. Among them, an extruder, especially a twin-screw extruder is preferably used from the viewpoint of improving dispersibility.

[Examples of Use of Resin According to Present Disclosure]

The resin combines excellent optical properties, heat resistance, and moldability with high transparency, and therefore can be used for, for example, optical films, optical discs, optical prisms, and lenses. When a reverse wavelength dispersion property is imparted to the resin, the resin is particularly suitably used for retardation films. Further, when a high refractive index property is imparted to the resin, the resin is particularly suitably used for high-refractive index lenses.

[Optical Film Made of Resin According to Present Disclosure]

As a method for forming an unstretched film using the resin according to the present disclosure, for example, the following method may be used. Specifically, a casting method (solution casting method) may be used in which a solution obtained by dissolving the resin in a solvent is cast, and then the solvent is removed. It is to be noted that the phrase "is cast" means that the solution is thinly spread to have, for example, a certain thickness.

Alternatively, a melt film formation method may be used in which a film is formed by melting the resin without using a solvent. Specific examples of the melt film formation method include melt extrusion using a T die, calendering, hot pressing, co-extrusion, co-melting, multilayer extrusion, and inflation molding. The method for forming an unstretched film is not particularly limited, but is preferably a melt film formation method from the viewpoint of preventing a problem caused by a remaining solvent in a casting method. Among the melt film formation methods, melt extrusion using a T die is more preferred from the viewpoint of ease of stretching performed as a post-process.

When an unstretched film is formed by the melt film formation method, the molding temperature is preferably 270° C. or less, more preferably 265° C. or less, particularly preferably 260° C. or less. If the molding temperature is too high, there is a possibility that defects in a resulting film caused by foreign matter or generation of air bubbles increase or the film is colored. However, if the molding temperature is too low, there is a possibility that molding is difficult due to too high a melt viscosity of the resin, which makes it difficult to form an unstretched film having a uniform thickness. Therefore, the molding temperature is usually 200° C. or more, preferably 210° C. or more, more preferably 220° C. or more. The molding temperature of an unstretched film is a temperature at the time of molding in the melt film formation method or the like, and is usually the temperature of outlet of a die through which the melted resin is extruded. That is, the molding temperature is obtained by measuring the temperature of the die outlet.

If present in the film, foreign matter is recognized as a defect such as light leakage when the film is used for a polarizing plate. In order to remove foreign matter in the resin, a film is preferably formed by a method in which the resin is filtered through a polymer filter attached after the extruder and then extruded through the die. At this time, the extruder, the polymer filter, and the die need to be connected together by pipes to transfer the melted resin. In order to prevent heat deterioration in the pipes as much as possible, it is preferred that the facilities are placed so that the retention time becomes as short as possible. Further, it is preferred that the process of transport and winding of the film after extrusion is performed in a clean room and attention is paid to prevent foreign matter from being attached to the film.

The thickness of the unstretched film is determined depending on, for example, the previously-designed thickness of a retardation film after stretching or stretching conditions such as stretch ratio. If the thickness is too large, thickness variations are likely to occur, and if the thickness is too small, there is a possibility that breakage occurs during stretching. From the viewpoint of preventing breakage, the thickness of the unstretched film is usually 30 μm or more, preferably 40 μm or more, more preferably 50 μm or more. From the viewpoint of preventing thickness variations, the thickness of the unstretched film is usually 200 μm or less, preferably 160 μm or less, more preferably 120 μm or less. The thickness variations in the unstretched film cause retardation variations in a retardation film. Therefore, the thickness of a portion to be used as a retardation film is preferably a predetermined thickness ±3 μm or less, more preferably a predetermined thickness ±2 μm or less, particularly preferably a predetermined thickness ±1 μm or less.

The length of the unstretched film in the longitudinal direction (e.g., in the stretching direction) is preferably 500 m or more, more preferably 1000 m or more, particularly preferably 1500 m or more. From the viewpoint of productivity or quality, it is preferred that stretching is continuously performed when a retardation film is produced. Usually, conditions for providing a predetermined retardation are adjusted at the start of stretching, and therefore if the length of the film is too short, the amount of a product that can be obtained after the adjustment of conditions reduces.

The internal haze of the unstretched film is preferably 3% or less, more preferably 2% or less, particularly preferably 1% or less. If the internal haze of the unstretched film is larger than the above upper limit, there is a case where light scattering occurs, which becomes a cause of, for example, depolarization in the case of laminating with a polarizer. The lower limit of the internal haze is not particularly specified, but is usually 0.10% or more. The internal haze is measured using a sample obtained by attaching an adhesive-backed transparent film whose haze has previously been measured to both surfaces of the unstretched film to remove the influence of an external haze, and a value obtained by subtracting the haze value of the adhesive-backed transparent film from a measured value of the sample is defined as the value of internal haze.

The b* value of the unstretched film is preferably 3 or less. In this case, it is possible to further prevent the occurrence of coloring or the like. The b* value is more preferably 2 or less, particularly preferably 1 or less.

In the unstretched film, irrespective of the thickness thereof, the total transmittance of the film per se is preferably 85% or more, more preferably 90% or more, particularly preferably 91% or more. When the transmittance is equal to or more than the lower limit, a less-colored film is obtained. As a result, when the film is laminated to, for example, a polarizing plate, a circularly polarizing plate having a high polarization degree or transmittance is obtained. When such a circularly polarizing plate is used in an image display device, high display quality can be achieved. It is to be noted that the upper limit of the total transmittance of the film according to the present disclosure is not particularly limited, but the total transmittance is usually 99% or less.

The surface reflection of the film can be reduced also by reducing the refractive index of the resin in addition to by reducing the haze or the b*value, which makes it possible to improve total transmittance. The refractive index at a sodium d line (589 nm) of the resin used in the present disclosure is preferably 1.49 to 1.56. Further, the refractive index is more preferably 1.50 to 1.55, even more preferably 1.51 to 1.54. The resin according to the present disclosure partially contains an aromatic structure. Therefore, the refractive index of the resin is higher than an aliphatic polymer having no aromatic structure, but can be made to fall within the above range by, for example, not using an aromatic compound as a copolymerization component of the resin.

The absolute value of photoelastic coefficient of the resin according to the present disclosure is preferably $20 \times 10^{-12}$ $Pa^{-1}$ or less, more preferably $15 \times 10^{-12}$ $Pa^{-1}$ or less, particularly preferably $12 \times 10^{-12}$ $Pa^{-1}$ or less. If the photoelastic coefficient is excessively large, there is a possibility that when the retardation film is laminated to a polarizing plate, a reduction in image quality, such as a phenomenon in which the periphery of a display becomes whitely blurred, occurs. Particularly, this problem becomes remarkable when such a retardation film is used for a large display device or a flexible (specifically, bendable, rollable, foldable) display device.

It is preferred that the unstretched film does not undergo brittle fracture in a folding test described later. A film that undergoes brittle fracture is likely to be broken during film formation or stretching, which may deteriorate the production yield. In order to produce a film that does not undergo brittle fracture, it is important that the resin used in the present disclosure is designed so that the molecular weight, melt viscosity, and glass transition temperature of the resin fall within their respective preferred ranges. Further, it is also effective to copolymerize or blend a component capable of imparting flexibility to adjust film properties.

A retardation film can be obtained by orienting the unstretched film through stretching. As a stretching method, a well-known method such as longitudinal uniaxial stretching, transverse uniaxial stretching using a tenter or the like, or a combination of them, such as simultaneous biaxial stretching or successive biaxial stretching may be used. The stretching may be performed by a batch system, but is preferably performed by a continuous system from the viewpoint of productivity. Further, as compared to a batch system, a retardation film having less variations in in-plane retardation can be obtained by a continuous system.

The stretching temperature is usually in the range of (Tg−20° C.) to (Tg+30° C.), preferably in the range of (Tg−10° C.) to (Tg+20° C.), more preferably in the range of (Tg−5° C.) to (Tg+15° C.). It is to be noted that Tg is the glass transition temperature of the resin used as a raw material. The stretch ratio is determined depending on a desired retardation value, but is, in each of the longitudinal and transverse directions, preferably 1.2 times to 4 times, more preferably 1.5 times to 3.5 times, even more preferably 2 times to 3 times. If the stretch ratio is too small, an effective range in which a desired degree of orientation and a desired orientation angle are obtained is narrow. On the other hand, if the stretch ratio is too large, there is a fear that the film is broken during stretching or wrinkles occur.

The stretching rate is appropriately selected depending on the intended use. It is to be noted that the stretching rate and the strain rate have a relationship represented by the following mathematical formula. The strain rate is usually 30%/min to 2000%/min, preferably 50%/min to 1000%/min, more preferably 70%/min to 500%/min, particularly preferably 100%/min to 400%/min. If the stretching rate is excessively large, there is a possibility that breakage occurs during stretching or optical properties greatly fluctuate due to long-term use under high-temperature conditions. Further, if the stretching rate is excessively small, there is a fear that not only productivity is reduced but also desired orientation property is not achieved due to the occurrence of orientation relaxation of polymer molecular chains during stretching.

Strain rate (%/min)={stretching rate (mm/min)/ length of unstretched film (mm)}×100

After the film is stretched, if necessary, heat fixation treatment may be performed by a heating furnace, or a relaxation process may be performed by controlling the width of a tenter or adjusting the circumferential speed of a roll. The heat fixation treatment is performed usually in the temperature range of 60° C. to (Tg), preferably in the temperature range of 70° C. to (Tg−5° C.). It is to be noted that Tg is the glass transition temperature of the resin used for the unstretched film. If the heat treatment temperature is too high, there is a possibility that the orientation of molecules achieved by stretching is disturbed so that a retardation significantly reduces from its desired value. Further, when the relaxation process is provided, stress produced in the stretched film can be removed by causing a shrinkage to 95% to 100% relative to the width of the film expanded by stretching. The treatment temperature applied to the film at this time is the same as the heat fixation treatment temperature. By performing such heat fixation treatment or relaxation process as described above, it is possible to prevent the fluctuation of optical properties due to long-term use under high-temperature conditions.

The in-plane birefringence (Δn) at a wavelength of 590 nm of a retardation film using the resin according to the present disclosure is preferably 0.0030 or more, more preferably 0.0035 or more, even more preferably 0.0040 or more, particularly preferably 0.0045 or more. The retardation is proportional to the thickness (d) and birefringence (Δn) of the film, and therefore by controlling the birefringence to fall within the above-specific range, a thin retardation film can be obtained which can develop a retardation as designed and can be fitted to a thin device. In order to develop a high birefringence, the degree of orientation of polymer molecules needs to be increased by, for example, reducing the stretching temperature or increasing the stretch ratio. However, under such stretching conditions, the film is likely to be broken, and therefore it is more advantageous that the resin to be used is superior in toughness. Basically, the birefringence is preferably higher, but if the birefringence is excessively high, there is a fear that it is difficult to accurately control the retardation by stretching. Therefore, the birefringence is preferably 0.1 or less. The birefringence is more preferably 0.08 or less, particularly preferably 0.05 or less.

Depending on the designed value of a desired retardation, the thickness of a retardation film using the resin according to the present disclosure is preferably 50 μm or less. The thickness is more preferably 45 μm or less, even more preferably 40 μm or less, particularly preferably 35 μm or less. On the other hand, if the thickness is excessively small, it is difficult to handle the film so that wrinkles occur or breakage occurs during production. Therefore, the thickness of the retardation film according to the present disclosure is preferably 5 μm or more, more preferably 10 μm or more.

The value of wavelength dispersion that is the ratio of a retardation at a wavelength of 450 nm (R450) to a retardation at a wavelength of 550 nm (R550) (R450/R550) of a retardation film using the resin according to the present disclosure is preferably 0.50 or more and 1.02 or less. The value of wavelength dispersion (i.e., R450/R550) is more preferably 1.00 or less, even more preferably 0.95 or less, even more preferably 0.90 or less, particularly preferably 0.87 or less. The value of wavelength dispersion is more preferably 0.70 or more, even more preferably 0.75 or more, even more preferably 0.80 or more. When the value of wavelength dispersion is within the above range, it is possible to obtain ideal retardation properties within a wide wavelength range in a visible region. For example, a circularly polarizing plate or the like can be produced by producing a retardation film having wavelength dependency as a ¼ wavelength plate and laminating the retardation film to a polarizing plate. This makes it possible to realize a polarizing plate and a display device having low dependence of hue on wavelength.

A circularly polarizing plate is obtained by laminating the retardation film to a well-known polarizing film and cutting the laminate to a desired size. Such a circularly polarizing plate can be used for, for example, compensation of viewing angle, prevention of external light reflection, color compensation, and conversion of linearly-polarized light to circularly-polarized light in various displays (liquid crystal displays, organic EL displays, plasma displays, electron field emission displays (FEDs), surface-conduction electron-emitter displays (SEDs)). Particularly, when the circularly polarizing plate is used as a circularly polarizing plate for prevention of external light reflection in an organic EL display, clear black display can be achieved, and the reliability of quality is also excellent. Further, the circularly polarizing plate has performance capable of responding to a reduction in device thickness in the future.

As the polarizing film, a polarizing film having an absorption axis in either the width direction or the longitudinal direction may be used. Specific examples of such a polarizing film include a film obtained by adsorbing a dichroic substance such as iodine or a dichroic dye to a hydrophilic polymer film such as a polyvinyl alcohol-based film, a partially-formalized polyvinyl alcohol-based film, an ethylene/vinyl acetate copolymer-based partially-saponified film and uniaxially stretching the film and a polyene-based oriented film such as a dehydration product of polyvinyl alcohol or a dehydrochlorination product of polyvinyl chloride. Among them, a long polarizing film obtained by adsorbing a dichroic substance such as iodine to a polyvinyl alcohol-based film and uniaxially stretching the film is particularly preferred because of its high polarization dichroic ratio.

In the circularly polarizing plate, the angle formed between the slow axis of the retardation film and the width direction of the polarizing film is preferably 380 or more and 520 or less, more preferably 400 or more and 500 or less, particularly preferably 420 or more and 480 or less. By adjusting the angle to fall within such a range, it is possible to prevent an increase in external light reflection and coloring of reflected light. This further improves image display quality.

The retardation film may be laminated to the polarizing film with a pressure-sensitive adhesive being interposed between them. As the pressure-sensitive adhesive, a well-known pressure-sensitive adhesive may be used as long as the optical properties of the laminated film are not impaired.

The circularly polarizing plate has sufficient optical properties as described above, and is configured so as to suitably be used for devices required to have precision, thinness, and homogeneity. Therefore, the circularly polarizing plate can suitably be used for liquid crystal panels for use in liquid crystal displays or organic EL panels for use in organic EL displays. Particularly, an organic EL panel has a metal layer that is likely to reflect external light, and is therefore likely to cause a problem such as external light reflection or reflection of a background. In order to prevent such external light reflection or the like, it is effective to provide the circularly polarizing plate on a light-emitting surface.

EXAMPLES

Hereinbelow, the present disclosure will be described in more detail with reference to Examples and Comparative Examples, but the present disclosure is not limited to the following Examples unless departing from the spirit thereof. The properties of the resin according to the present disclosure and the properties of an optical film obtained using the same were evaluated by the following methods. It is to be noted that the property evaluation methods are not limited to the following methods, and may appropriately be selected by those skilled in the art.

Reduced Viscosity of Resin

The resin was dissolved in methylene chloride to prepare a resin solution having a concentration of 0.6 g/dL. The transit time to of the solvent and the transit time t of the solution were measured at a temperature of 20.0° C.±0.1° C. using an Ubbelohde viscosity tube manufactured by Moritomo Rika Kogyo. A relative viscosity $\eta_{rel}$ was determined by the following formula (i) using the obtained to and t values, and further a specific viscosity $\eta_{sp}$ was determined by the following formula (ii) using the obtained relative viscosity $\eta_{rel}$.

$$\eta_{rel}=t/t_0 \quad \text{(i)}$$

$$\eta_{sp}=(\eta-\eta_0)/\eta_0=\eta_{rel}-1 \quad \text{(ii)}$$

Then, the obtained specific viscosity $\eta_{sp}$ was divided by the concentration c (g/dL) to determine a reduced viscosity $\eta_{sp}/c$. A higher reduced viscosity indicates a larger molecular weight.

Melt Viscosity of Resin

Pellets of the resin were dried in a hot-air dryer at 100° C. for 6 hours or more. The dried pellets were subjected to measurement using a capillary rheometer manufactured by Toyo Seiki Seisaku-sho, Ltd. The measurement temperature was set to 240° C., and a melt viscosity was measured at a shear rate of 6.08 to 1824 sec$^{-1}$, and a value measured at a shear rate of 91.2 sec$^{-1}$ was used as the value of melt viscosity. It is to be noted that an orifice having a die diameter of 1 mmφ×10 mmL was used.

Glass Transition Temperature (Tg) of Resin

The glass transition temperature of the resin was measured using a differential scanning calorimeter DSC6220 manufactured by SII NanoTechnology Inc. The resin of about 10 mg was placed in an aluminum pan manufactured by the same company and hermetically sealed, and the temperature was raised from 30° C. to 200° C. at a temperature rise rate of 20° C./min in a nitrogen stream of 50 mL/min. The temperature was maintained for 3 minutes, and then cooled to 30° C. at a rate of 20° C./min. The temperature was maintained at 30° C. for 3 minutes, and again raised to 200° C. at a rate of 20° C./min. Based on DSC data obtained by the second temperature rise, a temperature at the intersection between a straight line created by extending the base line on the low temperature side to the high temperature side and a tangent line drawn at a point where the gradient of a curved line in a portion of a stepwise change of glass transition becomes maximum was determined as an extrapolated glass transition start temperature and defined as a glass transition temperature.

Molding of Film

About 4 g of pellets of the resin dried in a hot-air dryer at 100° C. for 6 hours or more were sandwiched between polyimide films placed above and below the sample using a spacer having a length of 14 cm, a width of 14 cm, and a height of 0.1 mm, preliminarily heated at a temperature of 200 to 230° C. for 3 minutes, pressed at a pressure of 7 MPa for 5 minutes, then taken out together with the spacer, and cooled to form a film.

Photoelastic Coefficient

A photoelastic coefficient was measured using an apparatus obtained by combining a birefringence meter including a He—Ne laser, a polarizer, a compensator, an analyzer, and a light detector and an oscillational viscoelastometer (DVE-3 manufactured by Rheology) (for more details, see Journal of the Society of Rheology Japan Vol. 19, p. 93 to 97 (1991)). A specific method is as follows. First, a film produced by the above-described method was cut to obtain a sample having a width of 5 mm and a length of 20 mm. The sample was fixed to the viscoelastometer, and the storage elastic modulus E' of the sample was measured at room temperature (specifically, at 25° C.) and a frequency of 96 Hz. While the storage elastic modulus E' was measured, laser light emitted from the He—Ne laser was allowed to pass through the polarizer, the sample, the compensator, and the analyzer in this order. Then, the laser light was picked up by the detector (photodiode), and the signal thereof was allowed to pass through a rock-in amplifier to determine, from the wave form of an angular frequency of ω or 2ω, the amplitude thereof and a retardation relative to strain, and a strain-optic coefficient O' was determined. At this time, the direction (axis) of absorption axis of the polarizer and the direction of absorption axis of the analyzer were orthogonal to each other, and an angle between each of them and the stretching direction of the sample was adjusted to π/4. The photoelastic coefficient C was determined by the following formula using the storage elastic modulus E' and the strain-optic coefficient O'.

$$C=O'/E'$$

Stretching of Film

A film piece having a length of 70 mm and a width of 100 mm was cut out from a film produced by the above-described method and subjected to free-end uniaxial stretching using a batch-type biaxial stretching machine (BIX-277-AL manufactured by Island Industry Co., Ltd) to obtain a stretched film. The stretching was performed under conditions where the set temperature of an oven was the glass transition temperature of the resin +10° C., the stretching rate was 250%/min, and the stretch ratio was two times. When successfully performed under such conditions, the stretching was repeatedly performed by gradually increasing the stretch ratio to 2.1 times, 2.2 times, or more until the film piece was broken.

Measurement of Refractive Index and Abbe's Number of Monomer

Sample solutions having sample concentrations of 5 wt % to 20 wt % were prepared using 1-methyl-2-pyrrolidone (NMP) as a solvent and used as measurement samples.

The refractive indices at wavelength of 656 nm (C line), 587 nm (d line), and 486 nm (F line) (i.e., nC, nd, and nF) of the measurement samples were measured using a Kalnew Precision Refractometer KPR-2000 manufactured by Shimadzu Device Corporation. The measurement was performed at 23° C.

The concentration and the refractive index were plotted to make a linear function graph, and the graph was extrapolated to 100% concentration to obtain a refractive index.

An Abbe's number vd was calculated by the following formula.

$$vd=(1-nd)/(nC-nF)$$

A larger Abbe's number indicates smaller dependence of the refractive index on wavelength.

Retardation, Wavelength Dispersion, Birefringence of Stretched Film

A test piece having a width of 4 cm and a length of 4 cm was cut out from the center of a stretched film obtained by the above stretching method at the maximum stretch ratio. The retardation of the test piece was measured at a wavelength of 446.3 nm, 498.0 nm, 547.9 nm, 585.9 nm, 629.6 nm, and 747.1 nm using a retardation measuring device (specifically, KOBRA-WPR manufactured by Oji Scientific Instruments), and a wavelength dispersion property was determined from the measurement results. The wavelength dispersion property was expressed by the ratio between the retardation (R450) at a wavelength of 450 nm (specifically, at a wavelength of 446.3 nm) and the retardation (R550) at a wavelength of 550 nm (specifically, at a wavelength of 547.9 nm) (R450/R550). When R450/R550 is larger than 1, wavelength dispersion is positive, and when R450/R550 is less than 1, reverse wavelength dispersion is achieved. When the stretched film is used as a ¼ wavelength plate, the ideal value of R450/R550 is 0.818 (specifically, 450/550=0.818).

A birefringence (Δn) was determined from the retardation (R590) at a wavelength of 590 nm (specifically, at a wavelength of 585.9 nm) and the thickness of the stretched film on the basis of the following formula.

$$\text{Birefringence }(\Delta n)=R590\text{ [nm]}/(\text{Film thickness [mm]}\times 10^6)$$

As the birefringence (Δn) of each of the evaluation samples, the maximum value among values obtained by repeatedly performing stretching at different stretch ratios as described above was used. A larger value of birefringence indicates a higher degree of orientation of the polymer. Further, when the value of birefringence is larger, the thickness of the film for achieving a desired retardation value can be reduced. The ideal retardation of a ¼ wavelength plate at a wavelength of 590 nm is 147.5 nm. The film thickness for achieving a retardation of ¼ wavelength when a birefringence (Δn) obtained by the above method was developed was determined by the following formula.

$$\text{Thickness for achieving retardation of ¼ wavelength }[\mu m]=(147.5\text{ [nm]}/1000)/\Delta n$$

SYNTHESIS EXAMPLES OF MONOMERS

Methods for synthesizing a monomer used for producing a resin will be described below.

Synthesis Examples of Monomers

[Synthesis Example 1] Synthesis of 11H-indano[1,2-b]quinoline (Compound 1)

[Formula 47]

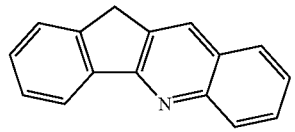

In a nitrogen atmosphere, 73.9 g (1324 mmol) of iron powder, 276 g of ethanol, 16.9 g (16.5 mmol) of TN hydrochloric acid, and 300 g of demineralized water were added to a 1-L four-necked flask, and the mixture was stirred while the inner temperature was heated to 70 to 75° C. A solution obtained by dissolving 50.0 g (331 mmol) of 2-nitrobenzaldehyde in 197 g of ethanol was added dropwise to the flask in 1 hour, the mixture was aged for 30 minutes, the inner temperature was then cooled to 50° C. or less, and 5.2 g of a 52 wt % aqueous potassium carbonate solution was added. The iron powder was filtered out using a Kiriyama funnel, and the iron powder residue separated by filtration was washed with 233 g of ethanol. The obtained filtrate was analyzed by HPLC, and as a result, 32.6 g (269 mmol, yield: 82%) of 2-aminobenzaldehyde was contained. The solution was vacuum-concentrated to distill away 233 g of ethanol, 39.4 g (298 mmol) of 1-indanone and 101.2 g of a 19 wt % potassium hydroxide-ethanol solution were added thereto, and the mixture was stirred for 1 hour under reflux conditions. The inner temperature was cooled to 50° C. or less, and 344 g of 1N hydrochloric acid was added to adjust the pH to 7 to 8. A precipitated solid was filtered out using a Kiriyama funnel and vacuum-dried at 80° C. to a constant mass. As a result, 60.8 g (yield: 79%) of 11H-indano[1,2-b]quinoline (compound 1) was obtained as a milky white solid.

[Synthesis Example 2] Synthesis of bis(11H-indeno[1,2-b]quinolin-11-yl)methane (Compound 2)

[Formula 48]

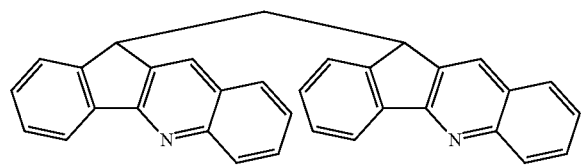

In a nitrogen atmosphere, 1.2 L of dimethylformamide, 100 g (460 mmol) of the compound 1, 1.84 g (23.01 mmol) of a 50 wt % aqueous potassium hydroxide solution, 18.7 g (230 mmol) of a 37% aqueous formalin solution were added to a 2-L flask, and the mixture was stirred for 2 hours at an inner temperature of 25° C. The reaction liquid was poured to 1 L of demineralized water, and a precipitated solid was filtered out and vacuum-dried at 40° C. to a constant mass. As a result, 45 g (101 mmol, yield: 44%) of bis(11H-indeno[1,2-b]quinolin-11-yl)methane (compound 2) was obtained.

[Synthesis Example 3] Synthesis of diethyl=3,3'-[methylenebis(11H-indeno[1,2-b]quinoline-11,11-diyl)]dipropionate (compound 3)

[Formula 49]

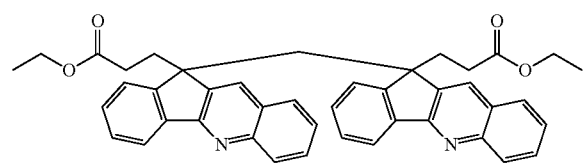

10 g (22 mmol) of bis(11H-indeno[1,2-b]quinolin-11-yl)methane (compound 2) obtained in Synthesis Example 2, 1 g (4.4 mmol) of N-benzyl-N,N,N-triethylammonium chloride, and 100 mL of tetrahydrofuran were placed in a 500-mL four-necked flask, the flask was purged with nitrogen, the inner temperature was then controlled to be 15 to 18° C., 6.0 g of a 48 wt % aqueous sodium hydroxide solution was added, 4.9 g (49 mmol) of ethyl acrylate was then added dropwise in 30 minutes, and the mixture was aged at room temperature for 3 hours. 200 mL of toluene and an aqueous saturated sodium hydrogen carbonate solution were added to perform liquid-liquid extraction, an organic layer was then vacuum-concentrated, and a residue was purified by silica gel column chromatography to obtain 5.0 g of diethyl=3,3'-[methylenebis(11H-indeno[1,2-b]quinoline-11,11-diyl)]dipropionate (compound 3). It is to be noted that the compound 3 was confirmed to be a diastereomer by subjecting part of a fraction as an eluate to NMR analysis. The compound 3 had a refractive index of 1.63 and an Abbe's number of 19. It is to be noted that the refractive index of the compound 3 was measured at a wavelength of 587 nm. The same goes for the refractive index of each of the following compounds.

Synthesis Example 4

Synthesis of diphenyl=3,3'-[methylenebis(11H-indeno[1,2-b]quinoline-11,11-diyl)]dipropionate (compound 4)

[Formula 50]

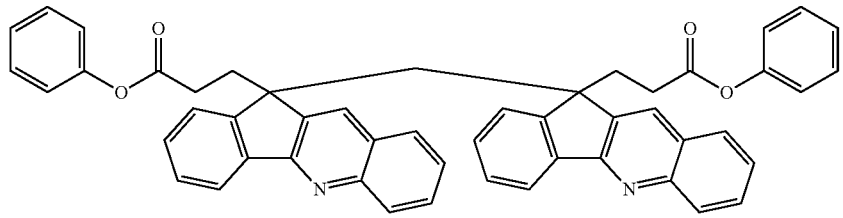

41 g (63.4 mmol) of diethyl=3,3'-[methylenebis(11H-indeno[1,2-b]quinoline-11,11-diyl)]dipropionate (compound 3) obtained in Synthesis Example 3, 67.9 g (317 mmol) of diphenyl carbonate, and 0.45 g (1.6 mmol) of tetraisopropyl orthotitanate were placed in a 500-mL separable flask, the degree of pressure reduction was adjusted to 3.0 kPa, and the mixture was stirred for 5 hours while a by-product was distilled away until the inner temperature reached 185° C. The pressure was returned to ordinary pressure by nitrogen, the inner temperature was then cooled to 90° C., and 203 g of ortho-xylene was added. The thus obtained solution was purified by silica gel column chromatography to obtain 14.8 g (yield: 31%) of diphenyl=3,3'-[methylenebis(11H-indano[1,2-b]quinoline-11,11-diyl)]dipropionate (compound 4) as a white solid. As a result of NMR analysis of the first fraction and the last fraction, the compound 4 was confirmed to be a diastereomer. The compound 4 had a refractive index of 1.64 and an Abbe's number of 18.

[Synthesis Example 5] Synthesis of 2,3-dihydro-1H-benz[e]inden-1-one (Compound 5)

[Formula 51]

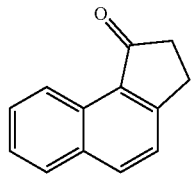

In a nitrogen atmosphere, 33 g (244 mmol) of aluminum chloride and 300 mL of anhydrous dichloromethane were added to a 1-L four-necked flask, and the mixture was stirred at room temperature. To the solution, a separately-prepared mixed solution of 25 g (195 mmol) of 3-chloropropanoyl chloride, 25 g (195 mmol) of naphthalene, and 200 mL of anhydrous dichloromethane was added dropwise in 1 hour, and the mixture was stirred at room temperature for 2 hours. The reaction liquid was vacuum-concentrated to distill away dichloromethane. As a result, 80 g of a compound 5 was obtained as a brown solid. To the compound 5, 28 g (483 mmol) of sodium chloride was added, and the mixture was stirred at 140° C. for 2 hours and then cooled to room temperature. The thus obtained reaction liquid was poured into 300 mL of iced water, the mixture was stirred for 30 minutes, and then 300 mL of water and 300 mL of dichloromethane were added to perform liquid-liquid extraction. The separated aqueous layer was subjected to extraction with 300 mL of dichloromethane twice. The organic layer combined with the dichloromethane was washed with 300 mL of saturated saline and then dried with anhydrous sodium sulfate. The sodium sulfate was filtered out, and then a filtrate was vacuum-concentrated and purified by silica gel column chromatography. As a result, 24 g (132 mmol, yield: 68%) of a compound 5 was obtained as a yellow solid.

[Synthesis Example 6] Synthesis of 7H-benz[6,7]indeno[1,2-b]quinoline (Compound 6)

[Formula 52]

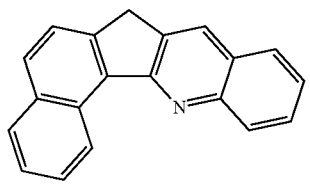

To 1.5 L of an ethanol solution containing 64 g (527 mmol) of 2-aminobenzaldehyde synthesized in the same manner as in Synthesis Example 1, 305 g (3.95 mol) of ammonium acetate and 48 g (263 mmol) of 2,3-dihydro-1H-benz[e]inden-1-one obtained in Synthesis Example 5 were added, and the mixture was stirred at 85° C. for 16 hours. 750 mL of an ethanol solution containing 32 g of 2-aminobenzaldehyde was added, and the mixture was stirred at 85° C. for 24 hours. The reaction liquid was vacuum-concentrated, and 2 L of water and 1.5 L of dichloromethane were added to a residue to perform liquid-liquid extraction. The aqueous layer was subjected to extraction with 1.5 L of dichloromethane twice. The obtained organic layer was washed with 2 L of saturated saline. The obtained organic layer was purified by silica gel column chromatography to obtain 85 g (318 mmol, yield: 40%) of a compound 6.

[Synthesis Example 7] Synthesis of diethyl=3,3'-[methylenebis(7H-benz[6,7]indeno[1,2-b]quinolone-7,7-diyl)]dipropionate (Compound 7)

[Formula 53]

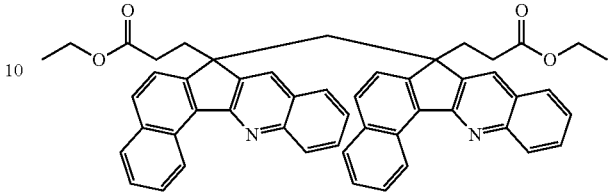

Diethyl=3,3'-[methylenebis(7H-benz[6,7]indeno[1,2-b]quinolone-7,7-diyl)]dipropionate (compound 7) was obtained in the same manner as in Synthesis Examples 2 and 3 except that the compound 6 obtained in Synthesis Example 6 was used as a raw material. The compound 7 had a refractive index of 1.67 and an Abbe's number of 14.

[Synthesis Example 8] Synthesis of diphenyl=3,3'-[methylenebis(7H-benz[6,7]indeno[1,2-b]quinoline-7,7-diyl)]dipropionate (Compound 8)

[Formula 54]

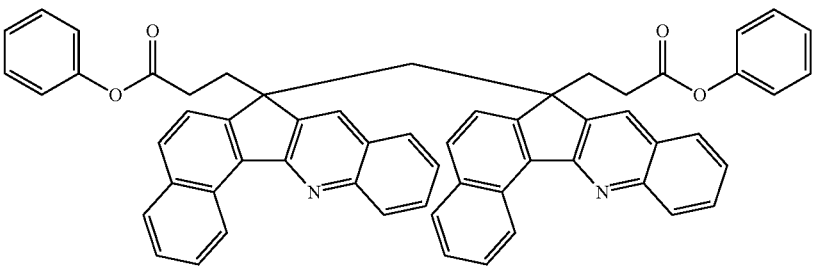

A compound 8 was obtained in the same manner as in Synthesis Example 4 except that the compound 7 was used as a raw material. The compound 8 had a refractive index of 1.68 and an Abbe's number of 15.

Synthesis Examples of Resins and Property Evaluations

Abbreviations for compounds used in Examples and Comparative Examples described below are as follows.

Bis[9-(2-phenoxycarbonylethyl)fluoren-9-yl]methane (Compound 9)

[Formula 55]

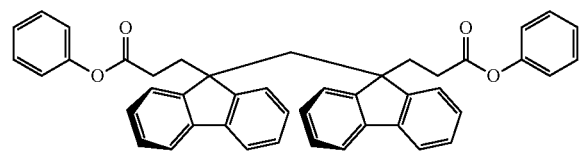

The compound 9 was synthesized by the method disclosed in JP 2015-25111 A.

DPC: Diphenyl carbonate (manufactured by Mitsubishi Chemical Corporation)
BHEPF: 9,9-bis[4-(2-hydroxyethoxy)phenyl]-fluorene (manufactured by Osaka Gas Chemicals Co., Ltd.)
BCF: 9,9-bis(4-hydroxy-3-methylphenyl)fluorene (manufactured by Osaka Gas Chemicals Co., Ltd.)
ISB: Isosorbide (manufactured by Roquette Freres under the product name of POLYSORB)
SPG: Spiroglycol (manufactured by Osaka Gas Chemicals Co., Ltd.)
CHDM: 1,4-cyclohexanedimethanol (manufactured by SK Chemicals Co., Ltd.)

Example 1

24.42 parts by weight (0.033 mol) of diphenyl=3,3'-[methylenebis(11H-indeno[1,2-b]quinoline-11,11-diyl)]dipropionate (compound 4), 23.76 parts by weight (0.163 mol) of ISB, 50.33 parts by weight (0.165 mol) of SPG, 63.21 parts by weight (0.295 mol) of DPC, and $1.73 \times 10^{-3}$ parts by weight ($9.84 \times 10^{-6}$ mol) of calcium acetate monohydrate as a catalyst were placed in a reaction container, and the inside of a reactor was purged with nitrogen under reduced pressure. The raw materials were dissolved by stirring in a nitrogen atmosphere at 150° C. for about 10 minutes. In the first-stage step of the reaction, the pressure was adjusted to 53.3 kPa, and then the temperature was increased to 220° C. in 30 minutes. After 30 minutes from the time when the temperature reached 220° C., the pressure was reduced from 53 kPa to 13.3 kPa in 60 minutes. Generated phenol was discharged to the outside of the reaction system. Then, in the second-stage step of the reaction, the temperature of a heating medium was increased to 245° C. in 15 minutes while the pressure was maintained at 13.3 kPa, and then the pressure was reduced to 0.10 kPa or less in 30 minutes. After the stirring torque reached a predetermined value, the pressure was returned to ordinary pressure by nitrogen to terminate the reaction, generated polyester carbonate was extruded into water, and the strand was cut to obtain pellets. The obtained polyester carbonate pellets were used to perform the various evaluations described above. The evaluation results are shown in Table 1.

Example 2

Example 2 was the same as Example 1 except that 25.49 parts by weight (0.034 mol) of diphenyl=3,3'-[methylenebis(11H-indeno[1,2-b]quinoline-11,11-diyl)]dipropionate (compound 4), 23.12 parts by weight (0.158 mol) of ISB, 50.33 parts by weight (0.165 mol) of SPG, 61.96 parts by weight (0.289 mol) of DPC, and $1.71 \times 10^{-3}$ parts by weight ($9.71 \times 10^{-6}$ mol) of calcium acetate monohydrate as a catalyst were used.

Example 3

Example 3 was the same as Example 1 except that 21.49 parts by weight (0.029 mol) of diphenyl=3,3'-[methylenebis(11H-indeno[1,2-b]quinoline-11,11-diyl)]dipropionate (compound 4), 25.54 parts by weight (0.175 mol) of ISB, 50.33 parts by weight (0.165 mol) of SPG, 66.66 parts by weight (0.311 mol) of DPC, and $1.80 \times 10^{-3}$ parts by weight ($1.02 \times 10^{-5}$ mol) of calcium acetate monohydrate as a catalyst were used.

Example 4

Example 4 was the same as Example 1 except that 26.02 parts by weight (0.035 mol) of diphenyl=3,3'-[methylenebis(11H-indeno[1,2-b]quinoline-11,11-diyl)]dipropionate (compound 4), 41.35 parts by weight (0.283 mol) of ISB, 30.20 parts by weight (0.099 mol) of SPG, 74.36 parts by weight (0.347 mol) of DPC, and $1.35 \times 10^{-3}$ parts by weight ($7.64 \times 10^{-6}$ mol) of calcium acetate monohydrate as a catalyst were used.

Example 5

Example 5 was the same as Example 1 except that 30.03 parts by weight (0.040 mol) of diphenyl=3,3'-[methylenebis(11H-indeno[1,2-b]quinoline-11,11-diyl)]dipropionate (compound 4), 46.43 parts by weight (0.318 mol) of ISB, 20.28 parts by weight (0.141 mol) of CHDM, 89.53 parts by weight (0.418 mol) of DPC, and $1.21 \times 10^{-3}$ parts by weight ($6.88 \times 10^{-6}$ mol) of calcium acetate monohydrate as a catalyst were used.

Example 6

Example 6 was the same as Example 1 except that 18.10 parts by weight (0.021 mol) of diphenyl=3,3'-[methylenebis(7H-benz[6,7]indeno[1,2-b]quinoline-7,7-diyl)]dipropionate (compound 8), 27.06 parts by weight (0.185 mol) of ISB, 50.33 parts by weight (0.165 mol) of SPG, 70.49 parts by weight (0.329 mol) of DPC, and $1.85 \times 10^{-3}$ parts by weight ($1.05 \times 10^{-5}$ mol) of calcium acetate monohydrate as a catalyst were used.

Comparative Example 1

Comparative Example 1 was the same as Example 1 except that 65.60 parts by weight (0.150 mol) of BHEPF, 25.90 parts by weight (0.177 mol) of ISB, 70.02 parts by weight (0.327 mol) of DPC, and $4.61 \times 10^{-4}$ parts by weight ($2.61 \times 10^{-6}$ mol) of calcium acetate monohydrate as a catalyst were used.

Comparative Example 2

Comparative Example 2 was the same as Example 1 except that 38.90 parts by weight (0.103 mol) of BCF, 53.83 parts by weight (0.177 mol) of SPG, 59.90 parts by weight (0.280 mol) of DPC, and $4.93 \times 10^{-3}$ parts by weight ($2.80 \times 10^{-5}$ mol) of calcium acetate monohydrate as a catalyst were used, and the final reaction temperature was changed to 260° C.

Comparative Example 3

Comparative Example 3 was the same as Example 1 except that 30.31 parts by weight (0.047 mol) of bis[9-(2-phenoxycarbonylethyl)fluoren-9-yl)]methane (compound 9), 39.94 parts by weight (0.273 mol) of ISB, 30.20 parts by weight (0.099 mol) of SPG, 69.67 parts by weight (0.325 mol) of DPC, and $7.88 \times 10^{-4}$ parts by weight ($4.47 \times 10^{-6}$ mol) of calcium acetate monohydrate as a catalyst were used.

Comparative Example 4

Comparative Example 4 was the same as Example 1 except that 31.58 parts by weight (0.049 mol) of bis[9-(2- phenoxycarbonylethyl)fluoren-9-yl)]methane (compound 9), 39.22 parts by weight (0.268 mol) of ISB, 30.20 parts by weight (0.099 mol) of SPG, 68.19 parts by weight (0.318 mol) of DPC, and $7.77 \times 10^{-4}$ parts by weight ($4.41 \times 10^{-6}$ mol) of calcium acetate monohydrate as a catalyst were used.

develop a very high birefringence (Δn590 nm), and therefore can have a small thickness when used as ¼ wavelength plates. Particularly, the films of Examples 1 to 4 and Example 6 have a sufficiently low photoelastic coefficient, and therefore have excellent performance and reliability when used as retardation films. Further, the resins of

TABLE 1

| | | | Example 1 | Example 2 | Example 3 | Example 4 | Example 5 |
|---|---|---|---|---|---|---|---|
| Resin Composition (The content of the structural unit derived from each monomer) | Compound 4 | mol % | 5.0 | 5.3 | 4.3 | 4.6 | 4.4 |
| | Compound 8 | mol % | | | | | |
| | Compound 9 | mol % | | | | | |
| | DPC | mol % | 45.0 | 44.7 | 45.7 | 45.4 | 45.6 |
| | BHEPF | mol % | | | | | |
| | BCF | mol % | | | | | |
| | ISB | mol % | 24.8 | 24.4 | 25.7 | 37.0 | 34.7 |
| | SPG | mol % | 25.2 | 25.6 | 24.3 | 13.0 | |
| | CHDM | mol % | | | | | 15.3 |
| | Compound 4 | wt % | 18.3 | 19.1 | 16.1 | 19.5 | 22.5 |
| | Compound 8 | wt % | | | | | |
| | Compound 9 | wt % | | | | | |
| | DPC | wt % | 8.3 | 8.1 | 8.7 | 9.7 | 11.7 |
| | BHEPF | wt % | | | | | |
| | BCF | wt % | | | | | |
| | ISB | wt % | 23.4 | 22.8 | 25.2 | 40.8 | 45.5 |
| | SPG | wt % | 50.0 | 50.0 | 50.0 | 30.0 | |
| | CHDM | wt % | | | | | 20.0 |
| Evaluation of Physical Properties | Reduced viscosity | dL/g | 0.49 | 0.48 | 0.50 | 0.43 | 0.43 |
| | Melt viscosity | Pa · s | 2250 | 2310 | 2390 | 2930 | 2610 |
| | Glass transition temperature | ° C. | 134 | 134 | 133 | 147 | 135 |
| | Photoelastic coefficient | $\times 10^{-12} Pa^{-1}$ | 11 | 11 | 10 | 13 | 18 |
| | R450/R550 | — | 0.85 | 0.82 | 0.90 | 0.85 | 0.85 |
| | Δ n 590 nm | — | 0.0050 | 0.0041 | 0.0069 | 0.0048 | 0.0050 |
| | λ/4 film thickness | μm | 29 | 36 | 21 | 31 | 29 |

| | | | Example 6 | Comparative Example 1 | Comparative Example 2 | Comparative Example 3 | Comparative Example 4 |
|---|---|---|---|---|---|---|---|
| Resin Composition (The content of the structural unit derived from each monomer) | Compound 4 | mol % | | | | | |
| | Compound 8 | mol % | 3.1 | | | | |
| | Compound 9 | mol % | | | | 6.3 | 6.7 |
| | DPC | mol % | 46.9 | 50.0 | 50.0 | 43.7 | 43.3 |
| | BHEPF | mol % | | | 22.9 | | |
| | BCF | mol % | | | 18.4 | | |
| | ISB | mol % | 26.4 | 27.1 | | 36.7 | 36.5 |
| | SPG | mol % | 23.6 | | 31.6 | 13.3 | 13.5 |
| | CHDM | mol % | | | | | |
| | Compound 4 | wt % | | | | | |
| | Compound 8 | wt % | 14.1 | | | | |
| | Compound 9 | wt % | | | | 21.5 | 22.4 |
| | DPC | wt % | 9.2 | 9.2 | | 7.8 | 9.1 | 8.9 |
| | BHEPF | wt % | | | 65.3 | | |
| | BCF | wt % | | | 38.7 | | |
| | ISB | wt % | 26.7 | 25.5 | | 39.4 | 38.7 |
| | SPG | wt % | 50.0 | | 53.5 | 30.0 | 30.0 |
| | CHDM | wt % | | | | | |
| Evaluation of Physical Properties | Reduced viscosity | dL/g | 0.48 | 0.35 | 0.49 | 0.47 | 0.46 |
| | Melt viscosity | Pa · s | 2450 | 2920 | 3750 | 3780 | 3750 |
| | Glass transition temperature | ° C. | 134 | 150 | 138 | 140 | 140 |
| | Photoelastic coefficient | $\times 10^{-12} Pa^{-1}$ | 12 | 28 | 19 | 9 | 10 |
| | R450/R550 | | 0.84 | 0.85 | 0.86 | 0.86 | 0.82 |
| | Δ n 590 nm | | 0.0049 | 0.0024 | 0.0026 | 0.0037 | 0.0030 |
| | λ/4 film thickness | μm | 30 | 61 | 57 | 40 | 49 |

As shown in Table 1, all the films of Examples 1 to 6 have a reverse wavelength dispersion property and further Example 1 to 6 have a sufficiently high glass transition temperature, and are therefore excellent in heat resistance.

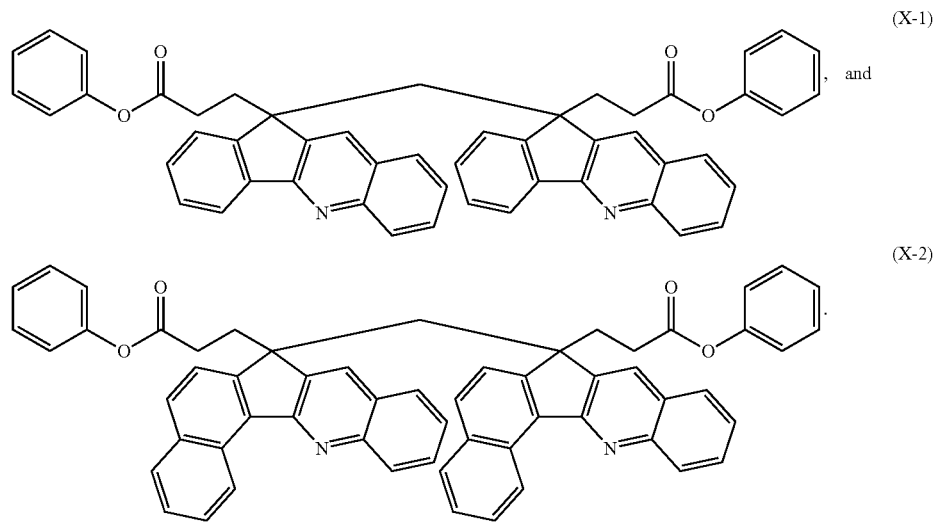

The invention claimed is:

1. A thermoplastic resin comprising a structural unit of formula (1):

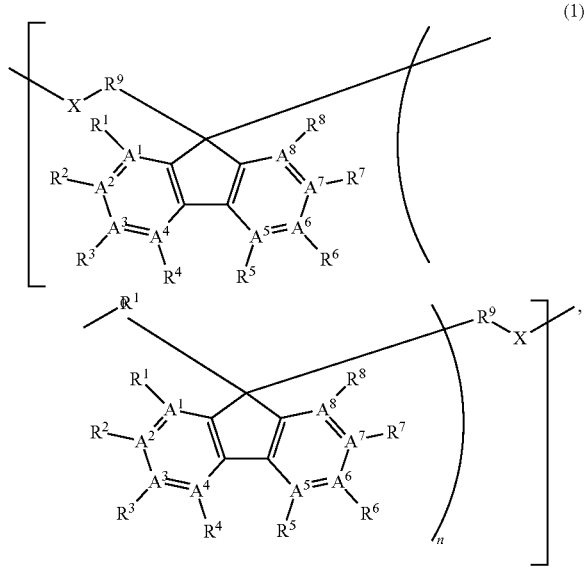

wherein $A^1$ to $A^8$ are each independently =CH— or =N—, and at least one of $A^1$ to $A^8$ is =N—,
$R^1$ to $R^8$ are each independently a hydrogen atom, an optionally substituted alkyl group having 1 to 10 carbon atoms, an optionally substituted aryl group having 6 to 11 carbon atoms, an optionally substituted heteroaryl group having 3 to 10 carbon atoms, an optionally substituted acyl group having 1 to 10 carbon atoms, an optionally substituted alkoxy group having 1 to 10 carbon atoms, an optionally substituted aryloxy group having 6 to 11 carbon atoms, an optionally substituted amino group, an optionally substituted vinyl group having 2 to 10 carbon atoms, an optionally substituted ethynyl group having 2 to 10 carbon atoms, a silicon atom having a substituent, a sulfur atom having a substituent, a halogen atom, a nitro group or a cyano group, wherein at least two adjacent groups out of $R^1$ to $R^8$ are optionally bonded to each other to form a ring, $R^9$ and $R^{10}$ are each independently a direct bond or an optionally substituted alkylene group having 1 to 20 carbon atoms, X is an oxygen atom, a carbonyl group, or an optionally substituted amino group, and n is an integer of 1 to 5.

2. The thermoplastic resin of claim 1, comprising the structural unit of formula (1) in an amount in a range of from 1 to 70 wt %.

3. The thermoplastic resin of claim 1, having an absolute value of a photoelastic coefficient of $20 \times 10^{-12}$ $Pa^{-1}$ or less.

4. The thermoplastic resin of claim 1, having a glass transition temperature in a range of from 110 to 160° C.

5. The thermoplastic resin of claim 1, comprising at least one selected from the group consisting of a polycarbonate, a polyester, and a polyester carbonate.

6. The thermoplastic resin of claim 1, further comprising at least one of a structural unit of formula (10) and a structural unit of formula (11):

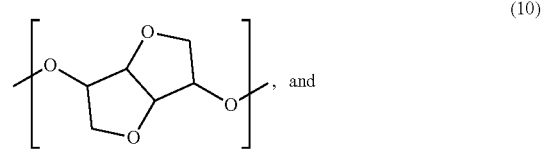

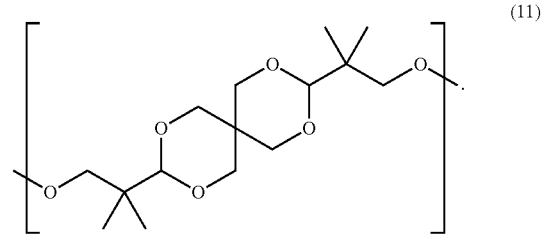

7. The thermoplastic resin of claim 1, wherein the structural unit of formula (1) comprises at least one selected from the group consisting of formula (V-1), formula (V-2), and formula (V-3):

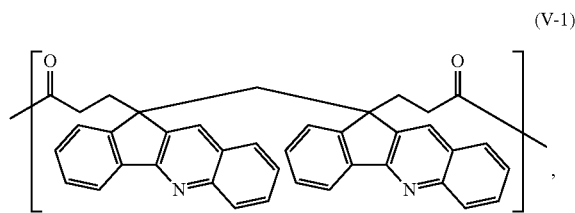

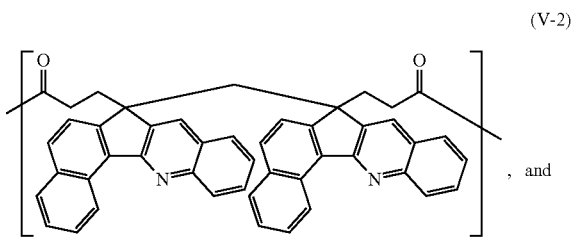

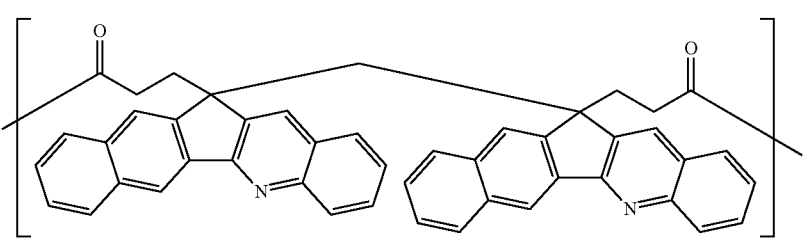

8. A transparent film, comprising the resin of claim 1.

9. A retardation film, comprising the transparent film of claim 8, stretched in at least one direction.

10. The retardation film of claim 9, wherein an R450/R550 ratio of a retardation at a wavelength of 450 nm (R450) and a retardation at a wavelength of 550 nm (R550) satisfies formula (I):

$$0.50 \leq R450/R550 \leq 1.02 \tag{I}$$

11. A circularly polarizing plate, comprising the retardation film of claim 9.

12. A diol compound of formula (7):

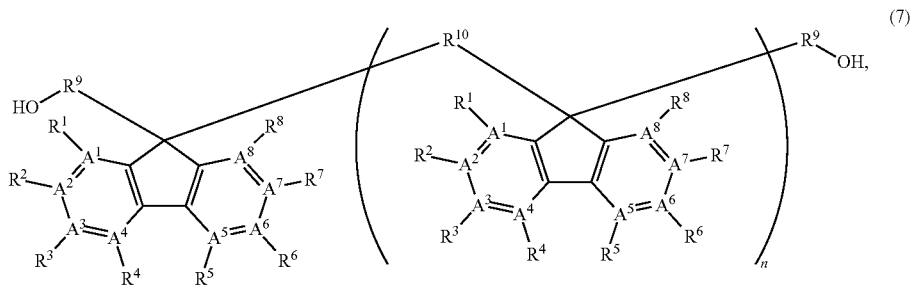

wherein $A^1$ to $A^8$ are each independently =CH— or =N—, and at least one of $A^1$ to $A^8$ is =N—, $R^1$ to $R^8$ are each independently a hydrogen atom, an optionally substituted alkyl group having 1 to 10 carbon atoms, an optionally substituted aryl group having 6 to 11 carbon atoms, an optionally substituted heteroaryl group having 3 to 10 carbon atoms, an optionally substituted acyl group having 1 to 10 carbon atoms, an optionally substituted alkoxy group having 1 to 10 carbon atoms, an optionally substituted aryloxy group having 6 to 11 carbon atoms, an optionally substituted amino group, an optionally substituted vinyl group having 2 to 10 carbon atoms, an optionally substituted ethynyl group having 2 to 10 carbon atoms, a silicon atom having a substituent, a sulfur atom having a substituent, a halogen atom, a nitro group or a cyano group, wherein at least two adjacent groups out of $R^1$ to $R^8$ are optionally bonded to each other to form a ring, $R^9$ and $R^{10}$ are each independently a direct bond or an optionally substituted alkylene group having 1 to 20 carbon atoms, and n is an integer of 1 to 5.

13. The diol compound of claim 12, wherein the formula (7) comprises at least one of formula (W-1) and formula (W-2):

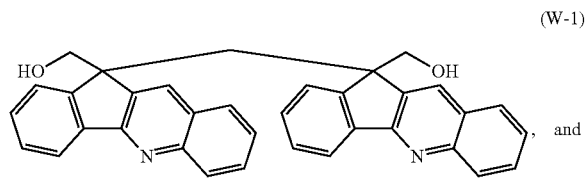

-continued

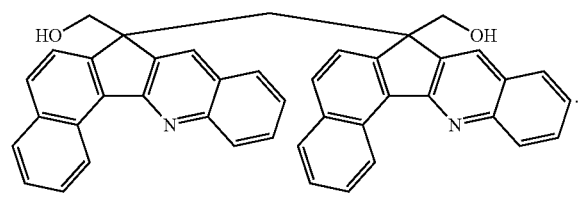

14. A diester compound of formula (8):

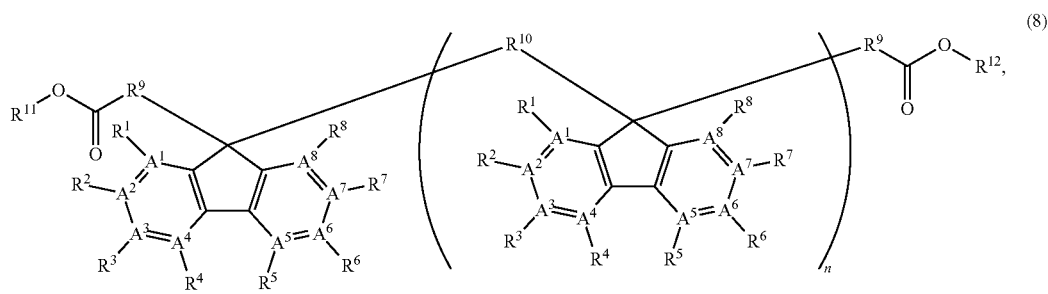

wherein $A^1$ to $A^8$ are each independently =CH— or =N—, and at least one of $A^1$ to $A^8$ is =N—, $R^1$ to $R^8$ are each independently a hydrogen atom, an optionally substituted alkyl group having 1 to 10 carbon atoms, an optionally substituted aryl group having 6 to 11 carbon atoms, an optionally substituted heteroaryl group having 3 to 10 carbon atoms, an optionally substituted acyl group having 1 to 10 carbon atoms, an optionally substituted alkoxy group having 1 to 10 carbon atoms, an optionally substituted aryloxy group having 6 to 11 carbon atoms, an optionally substituted amino group, an optionally substituted vinyl group having 2 to 10 carbon atoms, an optionally substituted ethynyl group having 2 to 10 carbon atoms, a silicon atom having a substituent, a sulfur atom having a substituent, a halogen atom, a nitro group or a cyano group, wherein at least two adjacent groups out of $R^1$ to $R^8$ are optionally bonded to each other to form a ring, $R^9$ and $R^{10}$ are each independently a direct bond or an optionally substituted alkylene group having 1 to 20 carbon atoms, $R^{11}$ and $R^{12}$ are each a hydrogen atom, an optionally substituted aryl group having 6 to 11 carbon atoms, an optionally substituted heteroaryl group having 3 to 10 carbon atoms, or an optionally substituted alkyl group having 1 to 10 carbon atoms, wherein $R^{11}$ and $R^{12}$ are same or different from each other, and and n is an integer of 1 to 5.

15. The diester compound of claim 14, wherein the formula (8) comprises at least one of formula (X-1) and formula (X-2):